United States Patent
Feldstein

(10) Patent No.: US 11,021,704 B2
(45) Date of Patent: *Jun. 1, 2021

(54) METHODS FOR RNA PROMOTER IDENTIFICATION

(71) Applicant: THE REGENTS OF THE UNIVERSITY OF CALIFORNIA, Oakland, CA (US)

(72) Inventor: Paul A. Feldstein, San Francisco, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/508,518

(22) Filed: Jul. 11, 2019

(65) Prior Publication Data

US 2020/0063124 A1    Feb. 27, 2020

Related U.S. Application Data

(62) Division of application No. 15/737,303, filed as application No. PCT/US2016/038802 on Jun. 22, 2016, now Pat. No. 10,392,615.

(60) Provisional application No. 62/185,060, filed on Jun. 26, 2015.

(51) Int. Cl.
| | | |
|---|---|---|
| *C12N 15/10* | (2006.01) | |
| *C12N 15/11* | (2006.01) | |
| *C12N 15/82* | (2006.01) | |
| *C12Q 1/6876* | (2018.01) | |

(52) U.S. Cl.
CPC ........ *C12N 15/1093* (2013.01); *C12N 15/111* (2013.01); *C12N 15/8205* (2013.01); *C12Q 1/6876* (2013.01); *C12N 2310/12* (2013.01); *C12N 2310/121* (2013.01); *C12N 2320/10* (2013.01); *C12N 2330/51* (2013.01)

(58) Field of Classification Search
None
See application file for complete search history.

(56) References Cited

U.S. PATENT DOCUMENTS

| 6,210,931 | B1 | 4/2001 | Feldstein |
| 10,738,302 | B2 * | 8/2020 | Feldstein et al. |
| 2003/0105043 | A1 | 6/2003 | Ho |
| 2004/0126388 | A1 | 7/2004 | King |
| 2006/0024788 | A1 | 2/2006 | Renner |
| 2008/0207539 | A1 | 8/2008 | Arbuthnot |
| 2010/0151502 | A1 | 6/2010 | Hauer |
| 2012/0174263 | A1 | 7/2012 | Saunders |

FOREIGN PATENT DOCUMENTS

| WO | 2016209989 A1 | 12/2016 |
| WO | 2016210321 A2 | 12/2016 |

OTHER PUBLICATIONS

ISA/US, Written Opinion of the International Searching Authority dated Nov. 17, 2016, related PCT international application No. PCT/US2016/038802, pp. 1-5.
ISA/US, International Search Report dated Nov. 17, 2016, related PCT international application No. PCT/US2016/038802, pp. 1-5.
ISA/US, International Preliminary Report on Patentability dated Dec. 26, 2017, related PCT international application No. PCT/US2016/038802, pp. 1-6.
Genbank KF853603, Feb. 3, 2014 (Feb. 3, 2014) [retrieved on Sep. 17, 2016 from http://www.ncbi.nlm.nih.gov/nuccore/576890587/] polynucleotide sequence of CMV Vector pNL3.2.
Genbank M14879, May 13, 2002 (May 13, 2002) [retrieved on Sep. 17, 2016 from http://www.ncbi.nlm.nih.gov/nuccore/335271/] polynucleotide sequence of satellite tobacco ringspot virus RNA.
Chay, Catherine A. et al., "Formation of Circular Satellite Tobacco Ringspot Virus RNA in Protoplasts Transiently Expressing the Linear RNA", Virology 239, 413-425 (1997).

* cited by examiner

*Primary Examiner* — Brian Whiteman
(74) *Attorney, Agent, or Firm* — O'Banion & Ritchey LLP; John P. O'Banion

(57) ABSTRACT

Provided are constructs and methods for RNA promoter identification.

20 Claims, 44 Drawing Sheets

Specification includes a Sequence Listing.

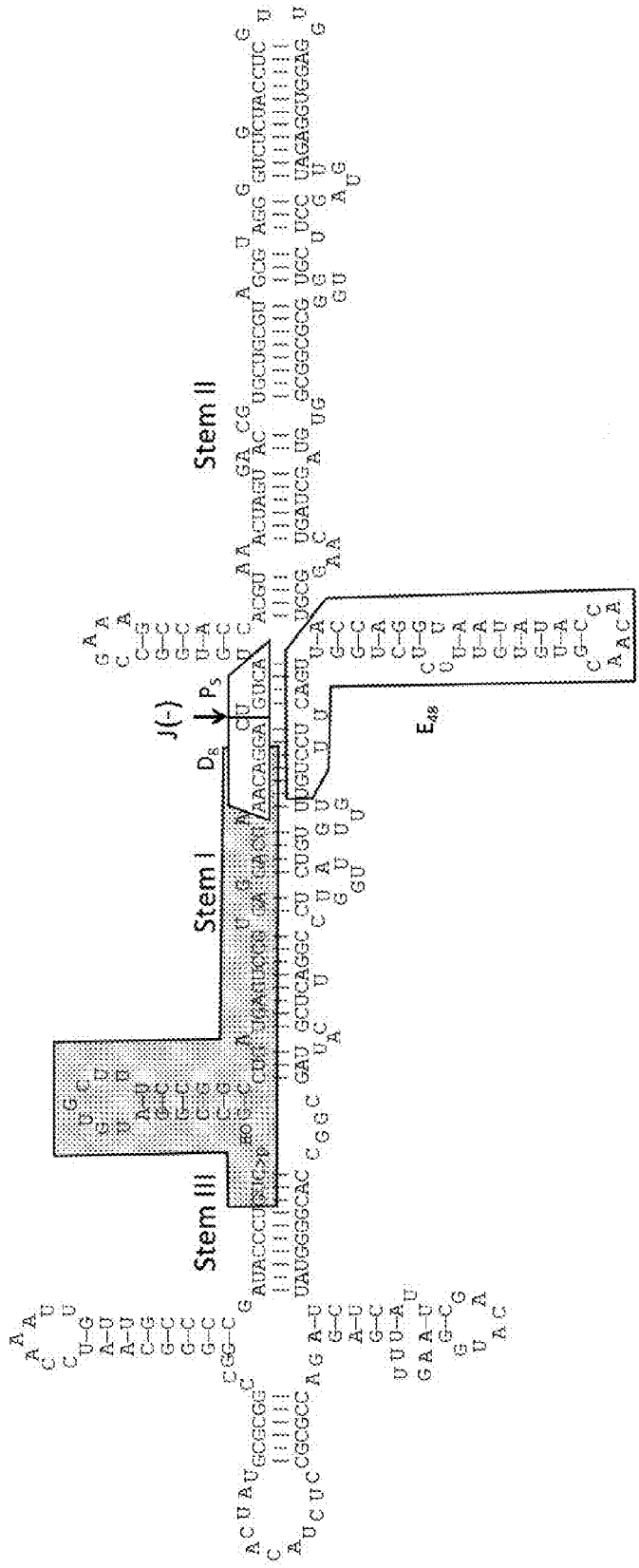
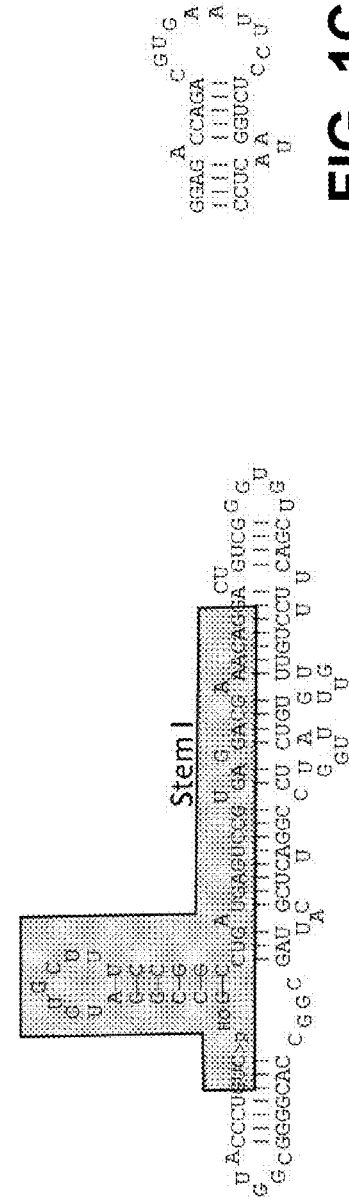
FIG. 1A
FIG. 1B
FIG. 1C

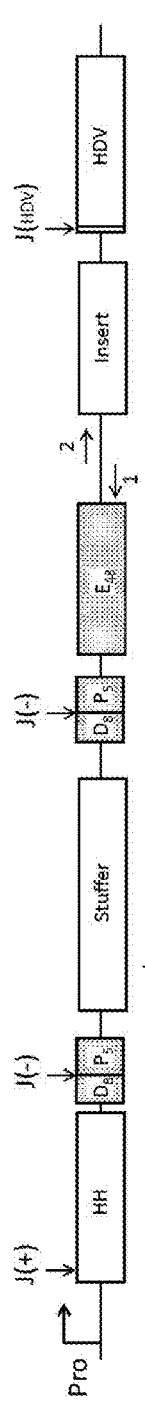
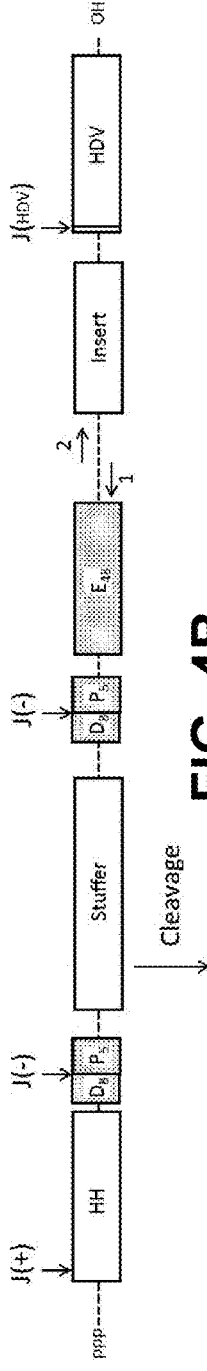
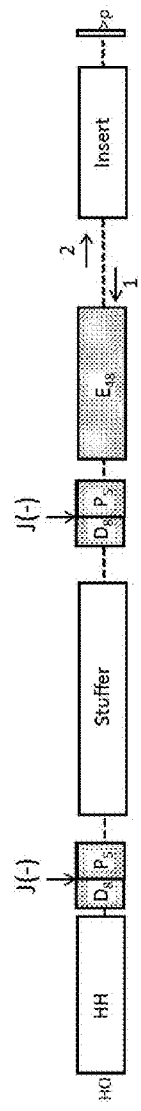
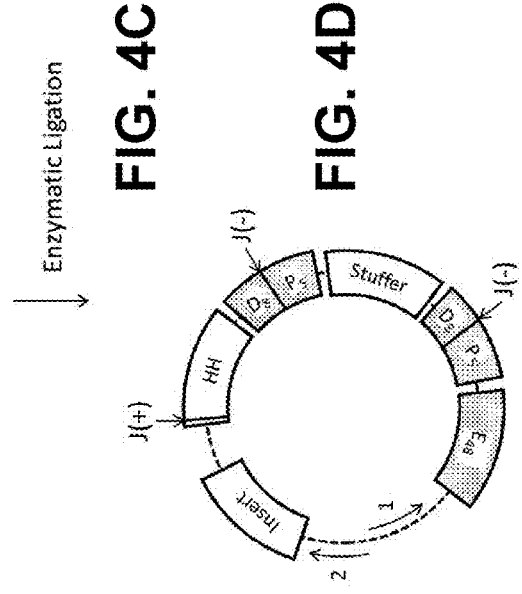
FIG. 4A
FIG. 4B
FIG. 4C
FIG. 4D

```
    *    10        20        30        40        50        60        70        80        90       100
    *    *         *         *         *         *         *         *         *         *         *
  1 ATACCCTGTCACCGGATGTGCTTTCCGGTCTGATGAGTCCGTGAGGACGAAACAGGACTGTCAGGTGGCCGAAAGCCACCACGTAAACTAGTGGATCCAA 100
    >>>>>>>>>>>>>>>>>>>>>>>>>>>>>>>>>>>>>>>>>>>>>>>>>>>>>>>>>>>>>>>>>
        Hammerhead ribozyme region                                                  Stuffer insertion site
                                                     >>>>>>>>                                       >>
                                                     D8 complement                          2nd D8 complement
                                                              >>>>>
                                                              P5 complement 110       120       130       140       150       160       170       180       190       200
    *    *         *         *         *         *         *         *         *         *         *
101 CAGGACTGTCAGCTAGTCAAGGCCGTACCAGGTAATATACCACAACGTGTCTTTCTCTGTTTGACTTCTCTGTTTGTGTGTCATTGGTTCCCGGATCTCG 200
                 >>>>>>>>>>>>>>>>>>>>>>>>>>>>>>>>>>>>>>>>>>>>>>>>>>>>>>>>>>>>>>>>>>>>>>>>>>>>
                            Hairpin catalytic core complement
    >>>>>
    2nd D8 complement
         >>>>>
         2nd P5 complement
```

*Fig. 8A*

201 CATTAGCGGGCGACGGGGTATCCTGCAGGAAGCTTGGATCCGTCGACGGCGGCCGCGATCGTCGACTGTAGAACTCTGAACCCTTGGCACCCGAGAATTCC 300
                                    >>>>>>>>>>>>>>>>>>>>>>>>>>>>>>>>>>>>>>>>>>>>>>>>>>>>>>>>>>>>>>>>>>>>>>>>>
                                    Multiple cloning site
                                                                                              >>>>>>>>>>>>>>>>>>>>
                                                                                              RT primer 1 complement 301 AGAATTCGGCGCGCCATACCCTGTCGGTCGGCATGGCATCTCCACCTCTCGCTCCTGCGACCTGGCATCCGACCTGCCGGTCCGACGTCCACTCGGATGG 400
    >>>>>>>>>>>>>>>>>>>>>>>    >>>>>>>>>>>>>>>>>>>>>>>>>>>>>>>>>>>>>>>>>>>>>>>>>>>>>>>>>>>>>>>>>>>>>>>>>>>>>>>>>>>>
    Multiple cloning site      HDV negative strand ribozyme
    >
    RT primer 1 complement
                                          >>>>>>>>>>>>>>>>>>>>>>>>>>>>>>>>>>>
                                          Primer 2 complement 401 CTAAGGGAGAGCC 413
    >>>>>>>>>>>>>
    HDV negative strand ribozyme

*Fig. 8B*

```
                  10         20         30         40         50         60         70         80         90        100
                   *          *          *          *          *          *          *          *          *          *
  1 AGATCTAATAGCACTCACTATAGGGGATCTATACCCTGTCACCGGATGTGCTTTCCGGTCTGATGAGTCCGTGAGGACGAAACAGGACTGTCAGGTGGCC 100
    >>>>>>>>>>>>>>>>                    >>>>>>>>>>>>>>>>>>>>>>>>>>>>>>>>>>>>>>>>>>>>>>>>>>>>>>>>>>>>>>>>
    T7 RNA promoter                      Hammerhead ribozyme region                          >>>>>>>
                                                                                             D8 complement
                                                                                                    >>>>>
                                                                                                    P5 complement 110        120        130        140        150        160        170        180        190        200
                   *          *          *          *          *          *          *          *          *          *
101 GAAAGCCACCACGTAAACTAGTGGATCCAACAGGACTGTCAGCTAGTCAAGGCGTACCAGGTAATATACCAACGTGTTTCTCTGGTTGACTTCTCT 200
                                   >>>>>>                                        >>>>>>>>>>>>>>>>>>>>>>>>>>>>>>>>>>>>>>>>>>>>>>>
                                    Stuffer insertion site                        Hairpin catalytic core complement
                              >>>>>>>
                              2nd D8 complement
                                   >>>>>
                                   2nd P5 complement 210        220        230        240        250        260        270        280        290        300
                   *          *          *          *          *          *          *          *          *          *
201 GTTTGTTGTGTGTCATTGGTTCCCGGGATCTCGCATTAGCGGCCGACGGGGTATCCTGCAGGAAGCTTGGATCCGTCGACCGGCCGATCGTCGACTGTAG 300
    >>                                                            >>>>>>>>>>>>>>>>>>>>>>>>>>>>>>>>>>>>>>>>>>>
    Hairpin catalytic core complement                              Multiple cloning site
                                                                                                  >>>>>>>>>>>>>>>
                                                                                                  Primer 2 complement
```

```
       710        720        730        740        750        760        770        780        790        800
         *          *          *          *          *          *          *          *          *          *
701 CGCTCCAAGCTGGCTGTGTGCACGAACCCCCGTTCAGCGACCCGCTGCGCCTTATCCGGTAACTATGCTCTTGAGTCCAACCGTAAGACACGACT 800
    vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
    rep (pMB1)

810        820        830        840        850        860        870        880        890        900
         *          *          *          *          *          *          *          *          *          *
801 TATCGCCACTGGCAGCAGCCACTGGTAACAGGATTAGCAGAGCGAGGTATGTAGGCGGTGCTACAGAGTTCTTGAAGTGGTGGCCTAACTACGGCTACAC 900
    vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
    rep (pMB1)

910        920        930        940        950        960        970        980        990       1000
         *          *          *          *          *          *          *          *          *          *
901 TAGAAGAACAGTATTTGGTATCTGCGCTCTGCTGAAGCCAGTTACCTTCGGAAAAAGAGTTGGTAGCTCTTGATCCGGCAAACAAACCACCGCTGGTAGC 1000
    vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
    rep (pMB1)

1010       1020       1030       1040       1050       1060       1070       1080       1090       1100
         *          *          *          *          *          *          *          *          *          *
1001 GGTGGTTTTTTTGTTTGCAAGCAGCAGATTACGCGCAGAAAAAAGGATCTCAAGAAGATCCTTTGATCTTTTCTACGGGTCTGACGCTCAGTGGAACG 1100
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv 1110       1120       1130       1140       1150       1160       1170       1180       1190       1200
         *          *          *          *          *          *          *          *          *          *
1101 AAAACTCACGTTAAGGGATTTTGGTCATGAGATTATCAAAAAGGATCTTCACCTAGATCCTTTTAAATTAAAAATGAAGTTTTAAATCAATCTAAAGTAT 1200
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv 1210       1220       1230       1240       1250       1260       1270       1280       1290       1300
         *          *          *          *          *          *          *          *          *          *
1201 ATATGAGTAAACTTGGTCTGACAGTTACCAATGCTTAATCAGTGAGGCACCTATCTCAGCGATCTGTCTATTTCGTTCATCCATAGTTGCCTGACTCCCC 1300
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
     ampR
```

*Fig. 10C*

```
            1310      1320      1330      1340      1350      1360      1370      1380      1390      1400
              *         *         *         *         *         *         *         *         *         *
1301  GTCGTGTAGATAACTACGATACGGGAGGGCTTACCATCTGGCCCCAGTCTGCAATGATACCGGCGAGAACCCACGGCTCACCGGCTCCAGATTTATCAGCAA
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      ampR 1410      1420      1430      1440      1450      1460      1470      1480      1490      1500
              *         *         *         *         *         *         *         *         *         *
1401  TAAACCAGCCAGCCGGAAGGGCCGAGCGCAGAAGTGGTCCTGCAACTTTATCCGCTCCATCCAGTCTATTAATTGTTGCCGGGAAGCTAGAGTAAGTAG
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      ampR 1510      1520      1530      1540      1550      1560      1570      1580      1590      1600
              *         *         *         *         *         *         *         *         *         *
1501  TTCGCCAGTTAATAGTTTGCGCAACGTTGTTGCCATTGCTACAGGCATCGTGGTGTCACGCTCGTCGTTTGGTATGGCTTCATTCAGCTCCGGTTCCCAA
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      ampR 1610      1620      1630      1640      1650      1660      1670      1680      1690      1700
              *         *         *         *         *         *         *         *         *         *
1601  CGATCAAGGCGAGTTACATGATCCCCATGTTGTGCAAAAAAGCGGTTAGCTCCTTCGGTCCTCCCGATCGTTGTCAGAAGTAAGTTGGCCGCAGTGTTAT
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      ampR 1710      1720      1730      1740      1750      1760      1770      1780      1790      1800
              *         *         *         *         *         *         *         *         *         *
1701  CACTCCATGGTTATGCAGCACTGCATAATTCTCTTACTGTCATGCCATCCGTAAGATGCTTTTCTGTGACTGGTGAGTACTCAACCAAGTCATTCTGAGA
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      ampR
```

*Fig. 10D*

```
         1810      1820      1830      1840      1850      1860      1870      1880      1890      1900
           *         *         *         *         *         *         *         *         *         *
1801 ATAGTGTATGCGGCGACCGAGTTGCTCTTGCCCGGCGTCAATACGGGATAATACCGCGCCACATAGCAGAACTTTAAAAGTGCTCTCATCATTGGAAAACGT 1900
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 1910      1920      1930      1940      1950      1960      1970      1980      1990      2000
           *         *         *         *         *         *         *         *         *         *
1901 TCTTCGGGGCGAAAACTCTCAAGGATCTTACCGCTGTTGAGATCCAGTTCGATGTAACCCACTCGTGCACCCAACTGATCTTCAGCATCTTTTACTTTCA 2000
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 2010      2020      2030      2040      2050      2060      2070      2080      2090      2100
           *         *         *         *         *         *         *         *         *         *
2001 CCAGGCGTTTCTGGGTGAGCAAAAACAGGAAGGCAAAATGCCGCAAAAAAGGGAATAAGGGCGACACGGAAATGTTGAATACTCATATACTCTTCCTTTTTCA 2100
     <<<<<<<<<<<<<<<<<<<<<<<<<<<<<<<<<<<<<<<<<<<<<<<<<<<<<<<<<<<<<<<<<<<<<<<<<<<<<<<<<<< >>>>>>>>>>>
     ampR                                                                                  seq1
                                                                                 <<<<<<<<<<<<<<<<<
                                                                                 ampr promoter 2110      2120      2130      2140      2150      2160      2170      2180      2190
           *         *         *         *         *         *         *         *         *
2101 ATATTATTGAAGCATTTATCAGGGTTATTGTCTCATGAGCGGATACATATTTGAAATGTATTTAGAAAAATAAACAAATAGGGGTTCCGCG 2190
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampr promoter
     >>>>>>>>>>>>>>
     seq1
```

*Fig. 10E*

```
             10         20         30         40         50         60         70         80         90        100
              *          *          *          *          *          *          *          *          *          *
  1  CCTGTGTTGGCATGCACATACAAATGGACGAACGGATAAACCTTTTCACGCCCTTTAAATATCCGATTATTCTTAATAAACGCTCTTTTTCTCTTAGGTT 100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Right border 110        120        130        140        150        160        170        180        190        200
              *          *          *          *          *          *          *          *          *          *
101  TACCCGCCAATATATCCTGTCAAACACTGATAGTTTGTGAACCATCACCCAAATCAAGTTTTTTGGGGTCGAGGTGCCGTAAAGCACTAAATCGAACCC 200
     >>>>>>>>>>>>>>>>>>>>>>>>>>>>>>>>>>>>>>>>>>>>>>>>>>>>>>>
     Right border 210        220        230        240        250        260        270        280        290        300
              *          *          *          *          *          *          *          *          *          *
201  TAAAGGGAGCCCCGATTTAGAGCTTGACGGGGAAAGCCGGCGAACGTGGCGAGAAAGGAAGAAAGCGAAAGGAGCGGCGCCATTCAGGCTGCG 300

310        320        330        340        350        360        370        380        390        400
              *          *          *          *          *          *          *          *          *          *
301  CAACTGTTGGGAAGGGCGATCGGTGCGGGCCCTCTTCGCTATTACGCCAGCTGGCGAAAGGGGATGTGCTGCAAGGCGATTAAGTTGGGTAACGCCAGGG 400

410        420        430        440        450        460        470        480        490        500
              *          *          *          *          *          *          *          *          *          *
401  TTTTCCCAGTCACGACGTTGTAAAACGACGGCCAGTGAATTGTTAATTAAGAATTCGAGCTCCACCGCGGAAACCCTCCTCGGATTCCATTGCCCAGCTAT 500
                                                                            >>>>>>>>>>>>>>>>>>>>>>>>>>>>>>
                                                                                            CaMV 35S promoter 510        520        530        540        550        560        570        580        590        600
              *          *          *          *          *          *          *          *          *          *
501  CTGTCACTTTATTGAGAAGATAGTGGAAAAGGAAGGTGGCTCCTACAAATGCCATCATTGCCGATAAAGGAAAGGCCATCGTTGAAGATGCCTCTGCCGAC 600
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S promoter
```

*Fig. 12A*

```
        610         620         630         640         650         660         670         680         690         700
  *         *         *         *         *         *         *         *         *         *
601 AGTGGTCCAAAGATGGACCCCCACCGAGGAGCATGTGGAAAAAGAAGACGTTCCAACCACGTCTTCAAAGCAAGTGGATTGATGTGATATCTCCA 700
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CaMV 35S promoter 710         720         730         740         750         760         770         780         790         800
  *         *         *         *         *         *         *         *         *         *
701 CTGACGTAAGGGATGACGCACAATCCCACTATCCTTCGCAAGACCCCTTCCTCTATATAAGGAAGTTCATTTCATTTGGAGAGGGTATACCCTGTCACCGG 800
    >>>>>>>>>>>>>>>>>>>>>>>>>>>>>>>>>>>>>>>>>>>>>>>>>>>>>>>>>>>>>>>>>>>>>>>>>>>>>>>>>>>>>> >>>>>>>
                                                                                          Hammerhead ribozyme region
    >>>>>>>>>>>>>>>>>>>>>>>>>>>>>>>>>>>>>>>>>>>>>>>>>>>>>>>>>>>>>>>>>>>>>>>>>>>>>>>>>>>>>>
    CaMV 35S promoter 810         820         830         840         850         860         870         880         890         900
  *         *         *         *         *         *         *         *         *         *
801 ATGTGCTTTCCGGTCTGATGAGTCCGTGAGGACGAAACAGGACTGTCAGGTGGCCGAAAGCCACCACGTAAACTAGTGGATCCAACAGGACTGTCAGCTA 900
    >>>>>>>>>>>>>>>>>>>>>>>>>>>>>>>
    Hammerhead ribozyme region
                                   >>>>>>>                  >>>>>>                        >>>>>>>
                                   D8 complement           Stuffer insertion site         2nd D8 complement
                                          >>>>>                                                  >>>>>
                                          P5 complement                                          2nd P5 complement 910         920         930         940         950         960         970         980         990        1000
  *         *         *         *         *         *         *         *         *         *
901 GTCAAGGCGTACCAGGTAATATACCACAACGTGTGTTTCCTGTTGACTTCTCTGTTTGTGTCATTGGTTCCCGGATCTCGCATTAGCGGCGACGG 1000
    >>>>>>>>>>>>>>>>>>>>>>>>>>>>>>>>>>>>>>>>>>>>>>>>>
    Hairpin catalytic core complement
```

Fig. 12B

```
     1010      1020      1030      1040      1050      1060      1070      1080      1090      1100
       *         *         *         *         *         *         *         *         *         *
1001 GGTATCCTGCAGGAAGCTTGGATCCGTCGACGCGGCCGCCGATCGTCGGACTGTCTAGAACTCTGAACCCTTGGCACCCGAGAATTCGGCGCGCC 1100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Multiple cloning site                             Primer 2 complement
                                                                               >>>>>>>>>>>>>>>>>>>
                                                                               RT primer 1 complement
     1110      1120      1130      1140      1150      1160      1170      1180      1190      1200
       *         *         *         *         *         *         *         *         *         *
1101 ATACCCGTGTCGGGCATGGCATGGCATCTCCACCTCTCCTCGCGGTCCGACCTGGGCATCCGAAGGAGGACAGACGTCCACTCGGATGGCTAAGGGAGAGCCAT 1200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     HDV negative strand ribozyme                                                       >
                                                                                        CaMV 35S terminator
     1210      1220      1230      1240      1250      1260      1270      1280      1290      1300
       *         *         *         *         *         *         *         *         *         *
1201 CGAATTCGCTGAAATCACCAGTCTCTCTACAAATCTATCTCTCTCTATTTTCTCCATAAATAATGTGTGAGTAGTTTCCGATAAGGGAAATTAGGGT 1300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator
     1310      1320      1330      1340      1350      1360      1370      1380      1390      1400
       *         *         *         *         *         *         *         *         *         *
1301 TCTTATAGGGTTTCGCTCATGTGTTGAGCATATAAGAAACCCTTAGTAGTATTTGTAAAATACTTCTATCAATAAAATTTCTAATTCCTAAAA 1400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator
```

*Fig. 12C*

```
     1410      1420      1430      1440      1450      1460      1470      1480      1490      1500
       *         *         *         *         *         *         *         *         *         *
1401 CCAAAAATCCAGTACTAAAAATCCAGATCTCCTAAAGTCCCTATAGATCTTTGTCGTGAATATAAACCAGAGACGACTAAACCTGGAGCCCAGACGC 1500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator 1510      1520      1530      1540      1550      1560      1570      1580      1590      1600
       *         *         *         *         *         *         *         *         *         *
1501 CGTTCGAAGCTAGAAGTACCGCTTAGGCAGGAGGGCCGTTAGGGAAAAGATGCTAAGGCAGGGTTGGTTACGTTGACTCCCCGTAGGTTTGGTTTAAATA 1600
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator 1610      1620      1630      1640      1650      1660      1670      1680      1690      1700
       *         *         *         *         *         *         *         *         *         *
1601 TGATGAAGTGGACGGAAGGAGGAAGGAGGAAGACAAGGAAGGAAGAAGGTTGCAGGCCCTGTGCAAGGTAAGAAGATGGAAATTTGATAGAGGTACGCTACTAT 1700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator 1710      1720      1730      1740      1750      1760      1770      1780      1790      1800
       *         *         *         *         *         *         *         *         *         *
1701 ACTTATACTATACGCTAAGGGAATGCTTGTATTTATACCCTATACCCCCTAATAAACCCTTATCAATTTAAGAAATAATCCGCATAAGCCCCCGCTTAAA 1800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator 1810      1820      1830      1840      1850      1860      1870      1880      1890      1900
       *         *         *         *         *         *         *         *         *         *
1801 AATTGGTATCAGAGCCATGAATAAGGTCTATGACCAAAACCTCAAGAGGATAAACCTCACCAAAAATACGAAAAGAGTTCTTAACTCTAAAGATAAAAGATGG 1900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CaMV 35S terminator
```

*Fig. 12D*

```
     1910      1920      1930      1940      1950      1960      1970      1980      1990      2000
       *         *         *         *         *         *         *         *         *         *
1901 CGCGTGGCCGGCCTACAGTATGAGCGGAGAATTAAGGGAGTCACGTTATGACCCCGCGATGACGGGACAAGCCGTTTACGTTTGGAACTGACAGA 2010      2020      2030      2040      2050      2060      2070      2080      2090      2100
       *         *         *         *         *         *         *         *         *         *
2001 ACCGCAACGTTGAAGGAGCCACTCAGCGCCGCGGGTTTCTGGAGTTTAATGAGCTAAGCACATACGTCAGAAACCATTATTGCGCGTTCAAAAGTCGCCTAA 2110      2120      2130      2140      2150      2160      2170      2180      2190      2200
       *         *         *         *         *         *         *         *         *         *
2101 GGTCACTATCAGCTAGCAAATATTTCTTGTCAAAAATGCTCCACTGACGTTCCATAAATTCCCCTCGGTATCCAATTAGAGTCTCATATTCACTTCTCAAT 2210      2220      2230      2240      2250      2260      2270      2280      2290      2300
       *         *         *         *         *         *         *         *         *         *
2201 CCAAATAATCTGCACCGGATCTGTTTCGCATGATTGAACAAGATGGATTGCACGCAGGTTCTCCGGCCGCTTGGGTGGAGAGGCTATTCGGCTAT
                                              >>>>>>>>>>>>>>>>>>>>>>>>>>>>>>>>>>>>>>>>>>>>>>>>>>>>
                                              neomycin phosphotransferase II 2310      2320      2330      2340      2350      2360      2370      2380      2390      2400
       *         *         *         *         *         *         *         *         *         *
2301 GACTGGGCACAACAGACAATCGGCTGCTCTGATGCCGCCGTGTTCCGGCTGTCAGCGCAGGGGCGCCCGGTTCTTTTTGTCAAGACCGACCTGTCCGGTG
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     neomycin phosphotransferase II 2410      2420      2430      2440      2450      2460      2470      2480      2490      2500
       *         *         *         *         *         *         *         *         *         *
2401 CCCTGAATGAACTGCAGGACGAGGCAGCGCGGCTATCGTGGCTGGCCACGACGGGCGTTCCTTGCGCAGCTGTGCTCGACGTTGTCACTGAAGCGGGAAG
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     neomycin phosphotransferase II
```

*Fig. 12E*

```
          2510       2520       2530       2540       2550       2560       2570       2580       2590       2600
            *          *          *          *          *          *          *          *          *          *
2501 GGACTGGCTGCTATTGGGCTGAAGTGCCGGGGCAGGATCTCCTGTCATCTCACCTTGCTCCTGCCGAGAAAGTATCCATCATGGCTGATGCAATGCGGGCGG
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     neomycin phosphotransferase II 2610       2620       2630       2640       2650       2660       2670       2680       2690       2700
            *          *          *          *          *          *          *          *          *          *
2601 CTGCATACGCTTGATCCGGCTACCTGCCCATTCGACCACCAAGCGAAACATGCGAGCGAGCACGTACTCGGATGGAAGCCGGTCTTGTCGATCAGG
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     neomycin phosphotransferase II 2710       2720       2730       2740       2750       2760       2770       2780       2790       2800
            *          *          *          *          *          *          *          *          *          *
2701 ATGATCTGGACGAAGAGCATCAGGGGCTCGCGCCAGCCGAACTGTTCGCCAGGCTCAAGGCGCGCATGCCCGACGGCGATGATCTCGTCGTGACCCATGG
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     neomycin phosphotransferase II 2810       2820       2830       2840       2850       2860       2870       2880       2890       2900
            *          *          *          *          *          *          *          *          *          *
2801 CGATGCCTGCTTGCCGAATATCATGGTGGAAAATGGCCGCTTTTCTGGATTCATCGACTGTGGCCGGCTGTGGCGGACCGCTATCAGGACATAGCG
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     neomycin phosphotransferase II 2910       2920       2930       2940       2950       2960       2970       2980       2990       3000
            *          *          *          *          *          *          *          *          *          *
2901 TTGGGCTACCCGTGATATTGCTGAAGAGCTTGGCGGCGAATGGGCTGACCGCTTCCTCGTGCTTTACGGTATCGCCGCTCCCGATTCGCAGGCGCATCGCCT
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     neomycin phosphotransferase II
```

*Fig. 12F*

```
            3010       3020       3030       3040       3050       3060       3070       3080       3090       3100
              *          *          *          *          *          *          *          *          *          *
3001  TCTATGCCTTCTTGACGAGTTCTTCTGAGCGGGACTCTGGGGTTCGAAATGACCGACCAAGGCGACGCCCAACCTGCCATCACGAGATTCGATTCCACC
      >>>>>>>>>>>>>>>>>>>>>>>>>>>>
      neomycin phosphotransferase II 3110       3120       3130       3140       3150       3160       3170       3180       3190       3200
              *          *          *          *          *          *          *          *          *          *
3101  GCCGCCTTCTATGAAAGGTTGGGCTTCGGAATCGTTTTCCGGGACGCCTGGATGATCCTCCAGCGCGGGGATCTCATGCTGGAGTTCTTCGCCCACG 3210       3220       3230       3240       3250       3260       3270       3280       3290       3300
              *          *          *          *          *          *          *          *          *          *
3201  GGATCTCTGCGGAACAGGCGGTCGGCGGTCGAAGGTGCCGATATCATTACGACAGCAAGCACAACGCCGACGATCCTGAGCGACAATATGATCGGCGGC 3310       3320       3330       3340       3350       3360       3370       3380       3390       3400
              *          *          *          *          *          *          *          *          *          *
3301  GTCCACATCAACGGCGTCGGCGGCGACTGCCCAGCAAGACCGAGATGCACCGCGATATCTTGCTGCGTTCGGATATTTTCGTGGAGTTCCCGCCACAGA 3410       3420       3430       3440       3450       3460       3470       3480       3490       3500
              *          *          *          *          *          *          *          *          *          *
3401  CCCGGATGATCCCCGATCGTTCAAACATTTGGCAATAAAGTTTCTTAAGATTGAATCCTGTTGCCGGTCTTGCGATGATTATCATATAATTTCTGTTGAA 3510       3520       3530       3540       3550       3560       3570       3580       3590       3600
              *          *          *          *          *          *          *          *          *          *
3501  TTACGTTAAGCATGTAATAATTAACATGTAATGCATGACGTTATTTATGAGAGGATGGGGTTTTTATGATTAGAGTCCCGCAATTATACATTTAATACGCGATA 3610       3620       3630       3640       3650       3660       3670       3680       3690       3700
              *          *          *          *          *          *          *          *          *          *
3601  GAAAACAAAATATAGCGCGCAAACTAGGATAAATTATCGCGCGCGGTGTCATCTATGTTACTAGATCGGACTGTAGGCCGGCCCTCACTGGTGAAAAGA
```

*Fig. 12G*

```
            3710       3720       3730       3740       3750       3760       3770       3780       3790       3800
              *          *          *          *          *          *          *          *          *          *
3701 AAAACCACCCCAGTACATTAAAAACGTCCGCAATGTGTTATTAAGTGTCTAAGCGTCAATTGTTACACCACAATATCCTGCCACCAGCCAA
     <<<<<<<<<<<<<<<<<<<<<<<<<<<
     Left border 3810       3820       3830       3840       3850       3860       3870       3880       3890       3900
              *          *          *          *          *          *          *          *          *          *
3801 CAGGTCCCCGACCGGCAGCTCGGCACAAAATCACCACTCGATACAGGCAGCCCATCAGTCCGGGACGGCGTCAGCGGAGAGCCGTTGTAAGGCGGCAGA
     <<<<<<<<<<<<<<<<<<<<<<<<<<<<<<<<<<<<<<<<<<<<<<<<<<<<<<

3910       3920       3930       3940       3950       3960       3970       3980       3990       4000
              *          *          *          *          *          *          *          *          *          *
3901 CTTTGCTCATGTTACCGATGCTATTCGGAAGAACGGCAACTAAGCTGCCGGGTTTGAAACACGGATGATCTCGCGGAGGGTAGCATGTTGATTGTAACGA 4010       4020       4030       4040       4050       4060       4070       4080       4090       4100
              *          *          *          *          *          *          *          *          *          *
4001 TGACAGAGCGTTGCTGCCTGTGATCAAATATCATTCCCTGCAGAGATCCGAATTATCAGCCTTTCATTTCTGCTTAACCGTGACAGAGTAGA 4110       4120       4130       4140       4150       4160       4170       4180       4190       4200
              *          *          *          *          *          *          *          *          *          *
4101 CAGGCTGTCTCGCGGCCCGAGGGCGCAGCCCGAGGAGGCCCGTTAGCGGGCCCCGTTAGCGGGGATGGGAGGGTTCGAGAAGGGGGCACCCCCTTCGGC
                                                                                     <<<<<<<<<<<<<<<<<<<<
                                                                                     OriV from pRK2

4210       4220       4230       4240       4250       4260       4270       4280       4290       4300
              *          *          *          *          *          *          *          *          *          *
4201 GTGCGCGGTCACGCGCACAGGGCGCAGCCCCTGGTTAAAAAATATTGGTTTAAAAACAAGGTTTATAAATATTGGTTTAAAAAGCAGGTTAGCGGTGGCCGAAAA
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     OriV from pRK2
```

*Fig. 12H*

```
             4310       4320       4330       4340       4350       4360       4370       4380       4390       4400
                *          *          *          *          *          *          *          *          *          *
4301 ACGGGGGGAAACCCTTGCAAATGCTGGATTTTCTGCCTGTGACAGCCCCTCAAATGTCAATAGTGCGCCCTCATCTGTCAGCACTCTGCCCCTCAAG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     OriV from pRK2

4410       4420       4430       4440       4450       4460       4470       4480       4490       4500
                *          *          *          *          *          *          *          *          *          *
4401 TGTCAAGGATCGGCGCCCCTCATCTGTCAGTAGTCGCGCCCCTCAAGTGTCAATACCGCAGGGCACTTATCCCCAGGCTTGTCCACATCATCTGTGGGAAA
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     OriV from pRK2

4510       4520       4530       4540       4550       4560       4570       4580       4590       4600
                *          *          *          *          *          *          *          *          *          *
4501 CTCGCGTAAAATCAGGCGTTTTCGCCGATTTGCGAGGCTGGCCAGCTCCACGTCGCCGGCCGAAATCGAGCCTGCCCCTCATCTGTCAACGCCGCCGG
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     OriV from pRK2

4610       4620       4630       4640       4650       4660       4670       4680       4690       4700
                *          *          *          *          *          *          *          *          *          *
4601 GTGAGTCGGCGCCCCTCAAGTGTCAACGTCCGCCCCTCATCTGTCAGTGAGGGCCAAGTTTTCCGCGAGGTATCCACAACGCCGGCGGCCGGGTGTCTCGC
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     OriV from pRK2

4710       4720       4730       4740       4750       4760       4770       4780       4790       4800
                *          *          *          *          *          *          *          *          *          *
4701 ACACGGCTTCGACGGGCGTTTCTGCGGCGTTTGCAGGGCCATAGACGGGCCAGCCCGAGGGCAACAGCCCCGGTGAGCGTGAGCGTCGGAAAGGCGCTC
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     OriV from pRK2
```

*Fig. 12I*

```
             4810       4820       4830       4840       4850       4860       4870       4880       4890       4900
               *          *          *          *          *          *          *          *          *          *
4801  GGTCTTGCCTTGCTCGTCGGTGATGTACACTAGTCGCTGGCTGCTGAACTGACCCCAGCCGGAACTGACCCCACAAGGCCCTAGCGTTTGCAATGCACCAGGT 4900
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
                                                                                     trfA 4910       4920       4930       4940       4950       4960       4970       4980       4990       5000
               *          *          *          *          *          *          *          *          *          *
4901  CATCATTGACCCAGGCGTGTTCCACCAGGCCGTGCCTGCCTCGCAACTCTTCGCCAGGCTTCGCGCCGACCTGCTCGCGCCACTTCTTCACGCGGTGGAATCCGA 5000
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA 5010       5020       5030       5040       5050       5060       5070       5080       5090       5100
               *          *          *          *          *          *          *          *          *          *
5001  TCCGCACATGAGGCGGAAGGTTTCCAGCTTGAGCGGGTACGGGTCCCGGTGCGAGCTGAAATAGTCGAACATCCGTCGGGCCGTCGGCGACAGCTTGCGG 5100
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA 5110       5120       5130       5140       5150       5160       5170       5180       5190       5200
               *          *          *          *          *          *          *          *          *          *
5101  TACTTCTCCCATATGAATTTCGTGTAGTGGTCGCCAGCAAACAGCACGATTTCCTCGTCGATCAGGACCTGGCAACGGGACGTTTTCTTGCCACGGT 5200
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA 5210       5220       5230       5240       5250       5260       5270       5280       5290       5300
               *          *          *          *          *          *          *          *          *          *
5201  CCAGGACGCGGAAGCGGTGCAGCAGGCGATTCCAGGTGCCCAACGCGGTCGGACCGTGAAGCCCATCGCCGTCCTGTAGGCGCGACAGGCATTC 5300
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA
```

*Fig. 12J*

```
              5310        5320        5330        5340        5350        5360        5370        5380        5390        5400
                *           *           *           *           *           *           *           *           *           *
5301  CTCGGCCTTCGTGTAATACCGGCCATTGATCGACCAGCCAGTCCTGGCAAAGCTCGTAGAACGTGAAGGTGATCGGCTAGCGCCGATAGGGGTGCGCTTC
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA 5410        5420        5430        5440        5450        5460        5470        5480        5490        5500
                *           *           *           *           *           *           *           *           *           *
5401  GCGTACTCCAACACCTGCTGCCACACCAGTTCGTCATCGTCGGCCCGCAGCTCGACGTGTAGTGATCTTCACGTGTTGACGTGGAAAAATGA
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA 5510        5520        5530        5540        5550        5560        5570        5580        5590        5600
                *           *           *           *           *           *           *           *           *           *
5501  CCTTGTTTGCAGGCGCCTCGCGCGGGGATTTTCTTGTTGCGCGTGTTGCGGTGTGAACAGGGCAGAGAGCGGCCGTGTCGTTTGGCATCGCTCGTGTCCGGCCA
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA 5610        5620        5630        5640        5650        5660        5670        5680        5690        5700
                *           *           *           *           *           *           *           *           *           *
5601  CGGGCAATATCGAACAAGGAAAGCTGCATTCCCTTGATCTGCTGCTTCGTGTGTTTCAGCAACGCGGCCTGCTTGGCCTGACCTGTTTTGCCAGG
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA 5710        5720        5730        5740        5750        5760        5770        5780        5790        5800
                *           *           *           *           *           *           *           *           *           *
5701  TCCTTCGCCGGCGGGTTTTTCGCTTCTTGGTCGTCATAGTTCCTCGCCGTGTCATCGACTTCGCCAAACCTGCCGCCTCCCTGTTCGAGACGACGCG
      vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
      trfA
```

Fig. 12K

```
                 5810        5820        5830        5840        5850        5860        5870        5880        5890        5900
                   *           *           *           *           *           *           *           *           *           *
5801    AACGCTCCACGGCGGGCCGATGGGCCGGGCAGGGGAGCCAGTTGCACGCTGTCGCGCTCGATCTTGGCCTGTAGCTTGCTGGACCATCGAGCCGAC
        vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
        trfA 5910        5920        5930        5940        5950        5960        5970        5980        5990        6000
                   *           *           *           *           *           *           *           *           *           *
5901    GGACTGGAAGGTTTCGCGGGGCGCACGCATGACGGTGCGGCTTGCGATGGTTTCGGCATCCTCGGCGGAAAAACCCGCGTCGATCAGTTCTTGCCTGTAT
        vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
        trfA 6010        6020        6030        6040        6050        6060        6070        6080        6090        6100
                   *           *           *           *           *           *           *           *           *           *
6001    GCCTTCCGGTCAAACGTCCGATTCATTCACCCCTCCTTGCGGGATTGCCCCGACTCACGCCCCGGGGCAATGTGCCCTTATTCCTGATTTGACCCGCCTGGTG
        vvvvvvvvvvvvvvvvvvv
        trfA 6110        6120        6130        6140        6150        6160        6170        6180        6190        6200
                   *           *           *           *           *           *           *           *           *           *
6101    GCCTTTCCGGTGTCCAGATAATCCACCTTATCGGCAATGAAGTCGGTCCCGTAGACCGTCCTTCTCGTACTTGGTATTCCGAATCTTGCCCTGCAC
        vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv 6210        6220        6230        6240        6250        6260        6270        6280        6290        6300
                   *           *           *           *           *           *           *           *           *           *
6201    GAATACCAGCGACCCCTTGCCCCAAATACTTGCCGTGGGCCTCGGCCTGAGAGCCAAAACACTTGATGCGGAAGAAGTCGGTGCGCTCCTGCTTGTCGCCG
        vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv 6310        6320        6330        6340        6350        6360        6370        6380        6390        6400
                   *           *           *           *           *           *           *           *           *           *
6301    GCATCGTTGCGCCACATCTAGGTACTAAAACAATTCATCCAGTAAAATATAATATTTTATTTTCTCCCAATCAGGCTTGATCCCCAGTAAGTCAAAAAAT
        vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
                              neomycin phosphotransferase III
```

*Fig. 12L*

```
        6410      6420      6430      6440      6450      6460      6470      6480      6490      6500
         *         *         *         *         *         *         *         *         *         *
6401 AGCTCGACATACTGTTCTTCCCGATATCCTCCCTGATCGACGGAAGGCAATGTCATACCACTTGTCCGCTTCTGCCCTGCCGCTTCTCCCAAGATCAA
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
     neomycin phosphotransferase III 6510      6520      6530      6540      6550      6560      6570      6580      6590      6600
         *         *         *         *         *         *         *         *         *         *
6501 TAAAGCCACTTACTTTGCCATCTTTCACAAAGATGTTGCTGTCTCCCAGGTCGCCGTGGGAAAAGACAAGTTCCTCTTCGGGCTTTTCCGTCTTTAAAAA
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
     neomycin phosphotransferase III 6610      6620      6630      6640      6650      6660      6670      6680      6690      6700
         *         *         *         *         *         *         *         *         *         *
6601 ATCATACAGCTCGCGCGGATCTTTAAATGGAGTGTCTTCTTCCCAGTTTTTCGCAATCCACATCGGCCAGATCGTTATTCAGTAAGTAATCCAATTCGGCT
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
     neomycin phosphotransferase III 6710      6720      6730      6740      6750      6760      6770      6780      6790      6800
         *         *         *         *         *         *         *         *         *         *
6701 AAGCGGCTGTCTAAGCTATTCGTATAGGGACAATCCGATATGTCGATGGAGTGAAAGAGCCTGATGCACTCCGCATACAGCTCGATAATCTTTTCAGGGC
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
     neomycin phosphotransferase III 6810      6820      6830      6840      6850      6860      6870      6880      6890      6900
         *         *         *         *         *         *         *         *         *         *
6801 TTTGTTCATCTTTCATACTCTTCCGAGCAAAGGACGCCATGGCCTCACTCATGAGCAGATTGCTCCAGCCATCATGCCGTTCAAAGTGCAGGACCTTTGG
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
     neomycin phosphotransferase III
```

*Fig. 12M*

```
      6910      6920      6930      6940      6950      6960      6970      6980      6990      7000
        *         *         *         *         *         *         *         *         *         *
6901 AACAGGGCAGCTTCTTCCACCAGCCATAGCATCATGTCCTTTCCCGTTCCTTTCCACATCATAGTGGTCCCTTTATACCGGCTGTCCGTCATTTTTAAATATAGG
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
     neomycin phosphotransferase III 7010      7020      7030      7040      7050      7060      7070      7080      7090      7100
        *         *         *         *         *         *         *         *         *         *
7001 TTTTCATTTTCTCCCACCAGCTTATATACCTTAGCAGGAGACATTCCTTCCGTATCTTTTTAGCAGCGGTATTTTTCGATCAGTTTTTTTCAATTCCGGTG
     vvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvvv
     neomycin phosphotransferase III 7110      7120      7130      7140      7150      7160      7170      7180      7190      7200
        *         *         *         *         *         *         *         *         *         *
7101 ATATTCTCATTTTAGCCATTTATTATTTCCTTCTCTTTTCTACAGTATTTAAAGATACCCCAAGAAGCTAATTATAACAAGACGAACTCCAATTCACTG
     vvvvvvvvvvvvvv
     neomycin phosphotransferase III 7210      7220      7230      7240      7250      7260      7270      7280      7290      7300
        *         *         *         *         *         *         *         *         *         *
7201 TTCCTTGCATTCTAAAACCTTAAATACCAGAAAAACAGCTTTTTCAAAGTTGTTTTCAAAGTTGGCGTATAACATAGTATCGACGGAGCCGATTTTGAAAC 7310      7320      7330      7340      7350      7360      7370      7380      7390      7400
        *         *         *         *         *         *         *         *         *         *
7301 CACAATTATGGGTGATGCTGCCAACTTACTGATTTAGTGTATGATGGTGTGTTTTTGAGGTGCTCCAGTGGCTTCTGTTTCTTATCAGCTGTCCCTCCTGTTC 7410      7420      7430      7440      7450      7460      7470      7480      7490      7500
        *         *         *         *         *         *         *         *         *         *
7401 AGCTACTGACGGGGTGGTGCGTAACGGCAAAAGCACCGCCGGACATCAGCGCTATCTCTGCTCTCACTGCCGTAAACATGGCAACTGCAGTTCACTTAC 7510      7520      7530      7540      7550      7560      7570      7580      7590      7600
        *         *         *         *         *         *         *         *         *         *
7501 ACCGCTTCTCAACCCGGTACGCACCAGAAATCATTGATAATGGCAATGAATGGCGTTGGATGCCGGGCAACAGCCCGCATTATGGGCGTTGGCCTCAACA
```

*Fig. 12N*

```
7610       7620       7630       7640       7650       7660       7670       7680       7690       7700
   *          *          *          *          *          *          *          *          *          *
7601 CGATTTTACGTCACTTAAAAACTCAGGCCGCAGTCGGTAACTATGCGGTGTGAAATACCGCACAGATGCGTAAGGAGAAAATACCGCATCAGGCGCTCT 7700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                                            ColE1 ori from pBR322

7710       7720       7730       7740       7750       7760       7770       7780       7790       7800
          *          *          *          *          *          *          *          *          *          *
7701 TCCGGTTCCTCGCTCACTGACTCGCTGCGCTCGGTCGTTCGGCTGCGGCGAGCGGTATCAGCTCACTCAAAGGCGGTAATACGGTTATCCACAGAATCAG 7800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322

7810       7820       7830       7840       7850       7860       7870       7880       7890       7900
          *          *          *          *          *          *          *          *          *          *
7801 GGGATAACGCAGGAAAGAACATGTGAGCAAAAGGCCAGCAAAAGGCCAGGAACCGTAAAAAGGCCGCGTTGCTGGCGTTTTTCCATAGGCTCCGCCCCC 7900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322

7910       7920       7930       7940       7950       7960       7970       7980       7990       8000
          *          *          *          *          *          *          *          *          *          *
7901 TGACGAGCATCACAAAAATCGACGCTCAAGTCAGAGGTGGCGAAACCCGACAGGACTATAAAGATACCAGGCGTTTCCCCCTGGAAGCTCCCTCGTGCGC 8000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322

8010       8020       8030       8040       8050       8060       8070       8080       8090       8100
          *          *          *          *          *          *          *          *          *          *
8001 TCTCCTGTTCCGACCCTGCCGCTTACCGGATACCTGTCCGCCTTTCTCCCTTCGGGAAGCGTGGCGCTTTCTCATAGCTCACGCTGTAGGTATCTCAGTT 8100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322
```

*Fig. 12O*

```
         8110      8120      8130      8140      8150      8160      8170      8180      8190      8200
           *         *         *         *         *         *         *         *         *         *
8101 CGGTGTAGGTCGTTCGCTCCAAGCTGGGCTGTGTGCACGAACCCCCGTTCAGCCCGACCGCTGCGCCTTATCCGGTAACTATCGTCTTGAGTCCAACCC 8200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 ori from pBR322

8210      8220      8230      8240      8250      8260      8270      8280      8290      8300
           *         *         *         *         *         *         *         *         *         *
8201 GGTAAGACACGACTTATCGCCACTGGCAGCAGCCACTGGTAACAGGATTAGCAGAGCGAGGTATGTAGGCGGTGCTACAGAGTTCTTGAAGTGGTGGCC 8300
     >>>>>>>>>>>>>>>>>>>>>>>>>>>>>>>>>>>>>>>>>>
     ColE1 ori from pBR322

8310
           *
8301 AGATCTGGGGAAC 8313
```

Fig. 12P

```
     *         *         *         *         *         *         *         *         *         *
  1 GGCCTAACTGGCCTCAATATTGGCCATTAGCCATATTATTCATTGGTTATATAGCATAAATCAATATTGGCTATTGGCCATTGCATACGTTGTATCTATA 100
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                      CMV promoter

*         *         *         *         *         *         *         *         *         *
101 TCATAATATGTACATTTATATTGGCTCATGTCCAATATGACCGCCATGTTGGCATTGATTATTGACTAGTTATTAATAGTAATCAATTACGGGGTCATTA 200
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CMV promoter

*         *         *         *         *         *         *         *         *         *
201 GTTCATAGCCCATATATGGAGTTCCGCGTTACATAACTTACGGTAAATGGCCCGCCTGGCTGACCGCCCAACGACCCCCGCCCATTGACGTCAATAATGA 300
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CMV promoter

*         *         *         *         *         *         *         *         *         *
301 CGTATGTTCCCATAGTAACGCCAATAGGGACTTTCCATTGACGTCAATGGGTGGAGTATTTACGGTAAACTGCCCACTTGGCAGTACATCAAGTGTATCA 400
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CMV promoter

*         *         *         *         *         *         *         *         *         *
401 TATGCCAAGTCCGCCCCCTATTGACGTCAATGACGGTAAATGGCCCGCCTGGCATTATGCCCAGTACATGACCTTACGGGACTTTCCTACTTGGCAGTAC 500
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CMV promoter
```

Fig. 14A

```
       510        520        530        540        550        560        570        580        590        600
         *          *          *          *          *          *          *          *          *          *
501 ATCTACGTATTAGTCATCGCTATTACCATGGTGATGCGGTTTTGGCAGTACACCAATGGGCGGTGGATAGCGGTTTGACTCACGGGGATTTCCAAGTCTCC 600
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CMV promoter 610        620        630        640        650        660        670        680        690        700
         *          *          *          *          *          *          *          *          *          *
601 ACCCCATTGACGTCAATGGGAGTTTGTTTTGGCACCAAAATCAACGGGACTTTCCAAAATGTCGTAATAACCCCGCCCCGTTGACGCAAATGGGCGGTAG 700
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    CMV promoter 710        720        730        740        750        760        770        780        790        800
         *          *          *          *          *          *          *          *          *          *
701 GCGTGTACGGTGGGAGGTCTATATAAGCAGAGCTCGTTTAGTGAACCGTCAGATCACTAGAAGCTTTATTGCGGTAGTTTATCACAGTTAAATTGCTAAC 800
    >>>>>>>>>>>>>>>>>>>>>>>>>>>>>>>>>>>>>>>>>>>>>>>>>>>>>>>>>>>>>>>>>>>>>>>>>>>>>>>>>
    CMV promoter 810        820        830        840        850        860        870        880        890        900
         *          *          *          *          *          *          *          *          *          *
801 GCAGTCAGTGGGCCTCGGCGGGCCAAGCTTGGCAATCCGGTACTGTTGGTAAAGCCACCATACCCTGTCACCGGATGTGCTTTCCGGTCTGATGAGTCCGT 900
                                                                                 >>>>>>>>>>>>>>>>>>>>>>>>>>
                                                                                 Hammerhead ribozyme region 910        920        930        940        950        960        970        980        990       1000
         *          *          *          *          *          *          *          *          *          *
901 GAGGACGAAACAGGACTGTCAGGTGGCCGAAAGCCACCACGTAAACTAGTGGATCCAACAGGACTGTCAGCTAGTCAAGGCGTACCAGGTAATATACCAC 1000
    >>>>>>>>>>>>>>                              >>>>>>>                         >>>>>>>>>>>>>>>>>>>>>>>>>>>>
    Hammerhead ribozyme region                  Stuffer insertion site          Hairpin catalytic core complement
    >>>>>>>>>                                   >>>>>>>>
    D8 complement                               2nd D8 complement
         >>>>>                                        >>>>>
         P5 complement                                2nd P5 complement
```

*Fig. 14B*

```
       1010       1020       1030       1040       1050       1060       1070       1080       1090       1100
         *          *          *          *          *          *          *          *          *          *
1001 AACGTGTGTTTCTCTGGTTGACTTCTCTGTTTGTTGTGTCATTGGTTCCCGGATCTCGCATTAGCGGCGACGGGGTATCCTGCAGGAAGCTTGGATCCGT 1100
     >>>>>>>>>>>>>>>>>>>>>>>>>>                                                        >>>>>>>>>>>>>>>>>>>
     Hairpin catalytic core complement                                                 Multiple cloning site 1110       1120       1130       1140       1150       1160       1170       1180       1190       1200
         *          *          *          *          *          *          *          *          *          *
1101 CGACGCGGCCGCGATCGTCGGACTGTAGAACTCTGAACCCTGGCACCCTGGCGCGCCATACCCTGTCGGTCGGCATGGCATCT 1200
     >>>>>>>>>>>>>>>>>>>>>>>>>>>>>>>>>>>>>>>>>>>>>>>>>>         >>>>>>>>>>>>>>>>>>>>>>>>>>
     Multiple cloning site                                      HDV negative strand ribozyme
                        >>>>>>>>>>>>>>>>>>>>>>>>>
                        RT primer 1 complement
         >>>>>>>>>>>>>>>>>>>>>>>>>
         Primer 2 complement 1210       1220       1230       1240       1250       1260       1270       1280       1290       1300
         *          *          *          *          *          *          *          *          *          *
1201 CCACCCTCCTCGCGGTCCGACCTGGGCATCCGAAGGAGGACAGAGACGTCCACTCGGATGGCTAAGGGAGAGCCAAGGCCGGACTCTAGAGTCGGGGGCGGCCG 1300
     >>>>>>>>>>>>>>>>>>>>>>>>>>>>>>>>>>>>>>>>>>>>>>>>>>>>>>>>>>>>>>>>>>
     HDV negative strand ribozyme 1310       1320       1330       1340       1350       1360       1370       1380       1390       1400
         *          *          *          *          *          *          *          *          *          *
1301 GCCGCTTCGAGCAGACATGATAAGATACATTGATGAGTTTGGACAAACCACAACTAGAATGCAGTGAAAAAAATGCTTTATTTGTGAAATTTGTGATGCT 1400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     polyA signal sequence
```

*Fig. 14C*

```
      1410       1420       1430       1440       1450       1460       1470       1480       1490       1500
        *          *          *          *          *          *          *          *          *          *
1401 ATTGCTTTATTTGTAACCATTATAAGCTGCAATAAACAAGTTAACAACAATTGCATTCATTTTATGTTTCAGGTTCAGGGGGAGGTGTGGGAGGTTT 1500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     polyA signal sequence 1510       1520       1530       1540       1550       1560       1570       1580       1590       1600
        *          *          *          *          *          *          *          *          *          *
1501 TTTAAAGCAAGTAAAACCTCTACAAATGTGGTAAAATCGATAAGGATCCGTTTGCGTATTGGGCGCTCTTCCGCTGATCGTGCGCAGCACCATGGCCTGAA 1600
     >>>>>>>>>>>>>>>>>>>>>>>>>                             >>>>>>>>>>>>>>>>>>>>>>>>>>>>>>>>>>>>>>>>>>>>>>>
     polyA signal sequence                                 SV40 early enhancer/promoter 1610       1620       1630       1640       1650       1660       1670       1680       1690       1700
        *          *          *          *          *          *          *          *          *          *
1601 ATAACCCTCTGAAAGAGGAACTTGGTTAGCTACCTTCTGAGGCGGAAGAACCAGCTGTGGAAATGTGTCAGTTAGGGTGTGGAAAGTCCCCAGGCTCCC 1700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     SV40 early enhancer/promoter 1710       1720       1730       1740       1750       1760       1770       1780       1790       1800
        *          *          *          *          *          *          *          *          *          *
1701 CAGCAGGCAGAAGTATGCAAAGCATGCATCTCAATTAGTCAGCAACCAGGCTGTGGAAAGTCCCCAGGCTCCCCAGCAGGCAGAAGTATGCAAAGCATGCA 1800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     SV40 early enhancer/promoter 1810       1820       1830       1840       1850       1860       1870       1880       1890       1900
        *          *          *          *          *          *          *          *          *          *
1801 TCTCAATTAGTCAGCAACCATAGTCCCGCCCATCCGCCCCTAACTCCGCCCAGTTCCGCCCATTCTCCGCCCATGGCTGACTAATT 1900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>
     SV40 early enhancer/promoter
```

*Fig. 14D*

```
          1910       1920       1930       1940       1950       1960       1970       1980       1990       2000
            *          *          *          *          *          *          *          *          *          *
1901  TTTTTATTTATGCAGAGGCCGAGGCCGCCCTCTGCCTCTGAGCTATTCCAGAAGTAGTGAGGAGGCTTTTTTGGAGGCCTAGGCTTTTGCAAAAAGCTCG 2000
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      SV40 early enhancer/promoter 2010       2020       2030       2040       2050       2060       2070       2080       2090       2100
            *          *          *          *          *          *          *          *          *          *
2001  ATTCTTCTGACACTAGCGCCACCATGAAGAAGCCCGAACTCACCGCTACCAGCGTTGAAAAATTTCTCATCGAGAAGTTCGACAGTGTGAGCGACCTGAT 2100
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
                          hygR 2110       2120       2130       2140       2150       2160       2170       2180       2190       2200
            *          *          *          *          *          *          *          *          *          *
2101  GCAGTTGTCGGAGGGCGAAGAGAGCCGAGCCTTCAGCTTCGATGTCGGCGGACGCTATGTACTGCGGGTGAATAGCTGCGCTGATGGCTTCTACAAA 2200
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      hygR 2210       2220       2230       2240       2250       2260       2270       2280       2290       2300
            *          *          *          *          *          *          *          *          *          *
2201  GACCGGCTACGTGTACTACCGCTTCGCCAGCGCTGCACTACCCCATCCCCCGAAGTGTTGGACATGGCGAGTTCAGCGACATGCTGACATACTGCATCAGTA 2300
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      hygR 2310       2320       2330       2340       2350       2360       2370       2380       2390       2400
            *          *          *          *          *          *          *          *          *          *
2301  GACGCGCCAAGGCGTTACTCTCCAAGACCTCCCCGAAACAGAGCTGCCTGCTGTGTTACAGCCTGTCGCCCGAAGCTATGATGCTATTGCCGCCGCCGA 2400
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      hygR
```

*Fig. 14E*

```
      2410        2420        2430        2440        2450        2460        2470        2480        2490        2500
        *           *           *           *           *           *           *           *           *           *
2401 CCTCAGTCAAACCAGCGGCTTCGGCCCCATTCGGCCCCAAGGCTCATCGGCCAGTACACAACCTGGCGGGATTTCATTTGCCATTGCGCCATTGCTGATCCCCATGTC
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2510        2520        2530        2540        2550        2560        2570        2580        2590        2600
        *           *           *           *           *           *           *           *           *           *
2501 TACCACTGGCAGACCGTGATGGACGACACCGTGTCCGCCAGCGTAGCTCAAGCCCTGTCAAGCCCTGGACGAACTGATGCTGTGGGCCGAAGACTGTCCCGAGGTGCCGCC
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2610        2620        2630        2640        2650        2660        2670        2680        2690        2700
        *           *           *           *           *           *           *           *           *           *
2601 ACCTCGTCGTCCATGCCGACTTCGGCAGCAACAACGTCCTGACCGACAAGGCCGCATCACCGCCGTAATCGACTGGTCCGAAGCTAGTTCGGGGACAGTCA
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2710        2720        2730        2740        2750        2760        2770        2780        2790        2800
        *           *           *           *           *           *           *           *           *           *
2701 GTACGAGGTGGCCAACATCTTCTTCTGGCGGCCCCTGGCTTGCATGGAGCAGCAGCTCGCTACTTCGAGCGCATCCCGAGCTGGCCGGCAGC
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 2810        2820        2830        2840        2850        2860        2870        2880        2890        2900
        *           *           *           *           *           *           *           *           *           *
2801 CCTCGTCTCGCGAGCCTACATGCTGCGCATCGGCCTGGATCAGCTCTACCAGAGCCTGGTGGACGGCAACTTCGACGATGCTGCGCCCTCGTGGGCTCAAGGCCGCT
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR
```

*Fig. 14F*

```
        2910       2920       2930       2940       2950       2960       2970       2980       2990       3000
          *          *          *          *          *          *          *          *          *          *
2901 GCGATGCCATCGTCCGCAGCGGGCCGGCACCGTCGGTCGCACACAAATCGCTCGCCGAGCGCAGCCGTATGGACCGACGGCTGCGTCGAGGTGCTGGC 3000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     hygR 3010       3020       3030       3040       3050       3060       3070       3080       3090       3100
          *          *          *          *          *          *          *          *          *          *
3001 CGACAGCGGCAACCGCCGGCCCAGTACACGACCGCGCGCTAAGGAGGTAGTTCGAGTTTAAACTCTAGAACCGGTCATGGCCGTCAATAAAATATCTTTAT 3100
     >>>>>>>>>>>>>>>>>>>>>>>>>>>>>>>>>>>>>>>>>>>>>>>>>>>>>>>>>>>>>>>>>>>>>>>>>>>>>>>>>>>>^
     hygR 3110       3120       3130       3140       3150       3160       3170       3180       3190       3200
          *          *          *          *          *          *          *          *          *          *
3101 TTTCATTACATCGTGTGTTGGTTTTTTGTGTGTTCGAACTAGATGCTGTCGACCGATGCCCTTGAGAGCCTTCAACCAGTCAGCTCCTTCCGGTGGGC 3200

3210       3220       3230       3240       3250       3260       3270       3280       3290       3300
          *          *          *          *          *          *          *          *          *          *
3201 CGACAGCGGCCGCAACTAGATGCTGTCGACCGATGCCCTTGAGAGCCTTCAACCAGTCAGCTCCTTCCGCTCTTCCGCTTCCGCTCTTCCTCCGCTCACTGA 3300
                                                                              >>>>>>>>>>>>>>>>>>>>>>>>>>>>>>
                                                                              ColE1 origin from pBR322

3310       3320       3330       3340       3350       3360       3370       3380       3390       3400
          *          *          *          *          *          *          *          *          *          *
3301 CTCGCTGCGCTCGGTCGTTCGGCTGCGGCGAGCGGTATCAGCTCACTCAAAGGCGGTAATACGGTTATCCACAGAATCAGGGGATAACGCAGGAAAGAAC 3400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     ColE1 origin from pBR322
```

*Fig. 14G*

```
              3410       3420       3430       3440       3450       3460       3470       3480       3490       3500
                *          *          *          *          *          *          *          *          *          *
3401  ATGTGAGCAAGGGCCAGGAACCGTAAAAAGGCCGTTGCTGGCGTTTTTCCATAGGCTCCGCCCCCCTGACGAGCATCACAAAAATC
      >>>>>>>>>>>>>>>>>>>>>>>>>>>>>>>>>>>>>>>>>>>>>>>>>>>>>>>>>>>>>>>>>>>>>>>>>>>>>>>>>>>>>>
      ColE1 origin from pBR322

3510       3520       3530       3540       3550       3560       3570       3580       3590       3600
                *          *          *          *          *          *          *          *          *          *
3501  GACGCTCAAGTCAGAGGTGGCGAAACCCGACAGGACTATAAAGATACCAGGCGTTTCCCCCTGGAAGCTCCCTCGTGCGCTCTCCTGTTCCGACCCTGCC
      >>>>>>>>>>>>>>>>>>>>>>>>>>>>>>>>>>>>>>>>>>>>>>>>>>>>>>>>>>>>>>>>>>>>>>>>>>>>>>>>>>>>>>
      ColE1 origin from pBR322

3610       3620       3630       3640       3650       3660       3670       3680       3690       3700
                *          *          *          *          *          *          *          *          *          *
3601  GCTTACCGGATACCTGTCCGCCTTTCTCCCTTCGGGAAGCGTGGCGCTTTCTCATAGCTCACGCTGTAGGTATCTCAGTTCGGTGTAGGTCGTTCGCTCC
      >>>>>>>>>>>>>>>>>>>>>>>>>>>>>>>>>>>>>>>>>>>>>>>>>>>>>>>>>>>>>>>>>>>>>>>>>>>>>>>>>>>>>>
      ColE1 origin from pBR322

3710       3720       3730       3740       3750       3760       3770       3780       3790       3800
                *          *          *          *          *          *          *          *          *          *
3701  AAGCTGGGCTGTGTGCACGAACCCCCCGTTCAGCCCGACCGCTGCGCCTTATCCGGTAACTATCGTCTTGAGTCCAACCCGGTAAGACACGACTTATCGC
      >>>>>>>>>>>>>>>>>>>>>>>>>>>>>>>>>>>>>>>>>>>>>>>>>>>>>>>>>>>>>>>>>>>>>>>>>>>>>>>>>>>>>>
      ColE1 origin from pBR322

3810       3820       3830       3840       3850       3860       3870       3880       3890       3900
                *          *          *          *          *          *          *          *          *          *
3801  CACTGGCAGCAGCCACTGGTAACAGGATTAGCAGAGCGAGGTATGTAGGCGGTGCTACAGAGTTCTTGAAGTGGTGGCCTAACTACGGCTACACTAGAAG
      >>>>>>>>>>>>>>>>>>
      ColE1 origin from pBR322
```

*Fig. 14H*

```
              3910       3920       3930       3940       3950       3960       3970       3980       3990       4000
                *          *          *          *          *          *          *          *          *          *
3901  AACAGTATTTGGTATCTGCGCTCTGCTGAAGCCTAGTTACCTTCGGAAAAAGAGTTGGTAGCTCTTGATCCGGCAAACAACCACCGCTGGTAGCGGTGGT 4010       4020       4030       4040       4050       4060       4070       4080       4090       4100
                *          *          *          *          *          *          *          *          *          *
4001  TTTTTGTTTGCAAGCAGCAGATTACGCGCAGAGATTCAAGAAGATCTCAAGAAGATCTTTTCTACGGGGTCTGACGCTCAGTGGAACGAAAACT 4110       4120       4130       4140       4150       4160       4170       4180       4190       4200
                *          *          *          *          *          *          *          *          *          *
4101  CACGTTAAGGGATTTTGGTCATGAGATTATCAAAAAGGATCTTCACCTAGATCCTTTTAAATTAAAAATGAAGTTTTAAATCAATCTAAAGTATATATGA 4210       4220       4230       4240       4250       4260       4270       4280       4290       4300
                *          *          *          *          *          *          *          *          *          *
4201  GTAAACTTGGTCTGACAGTTAACCACTGCAGTGGTTACCAGTGCTAAACCACTGCAGTGGTTACCAGTGCTGATCAGTGAGGCACCGATCTCAGCGATCTGCCTATTTCGTT
                                                                                                  <<<<<<<<<<<<
                                                                                                     ampR 4310       4320       4330       4340       4350       4360       4370       4380       4390       4400
                *          *          *          *          *          *          *          *          *          *
4301  CGTCCATAGTTGGCCTGACTCCCCGTCGTGTAGATAATCACTACGATTCGTGAGGGCTTACCATCAGGCCCCAGCGCAGCAATGATGCCGGAGAGCCGCGTTC
      <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
       ampR 4410       4420       4430       4440       4450       4460       4470       4480       4490       4500
                *          *          *          *          *          *          *          *          *          *
4401  ACCGGGCCCCCGATTTGTCAGCAATGAACCAGCCAGCGAGGGAGCCCGAAGAAGTGGTCCGCTACTTTGTCCGCCTCCATCCAGTCTATGAGCTGC
      <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
       ampR
```

*Fig. 14I*

```
4501 TGTCGTGATGCTAGAGTAAGAAGTTGGCCAGTGAGTAGTTTCCGAAGAGTTGTGGCCATTGCTACTGGCATCGTGGTATCACGCTCGTCGTTCGGTATGG 4600
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 4601 CTTCGTTCAACTCTGGTTCCCAGCGGTCAAGCCGGTCACATGATCACCCATATTATTGAAGAATGCAGTCAGTCAGCTCCTTAGGGCCTCCGATCGTTGTCAG 4700
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 4701 AAGTAAGTTGGCCCGGCGTGTGTCGCTCATGGTAACTGGCAGCACTACACAATTCTCTTACCGTCATGCCATCCGTAAGATGCTTTTCCGTGACCGGCGAG 4800
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 4801 TACTCAACCAAGTCGTTTGTGAGTAGTGTATACGGGCGACCAAGCTGCTCTTGCCCGGCGTCTATACGGGACAACACCGCCACATAGCAGTACTTTGA 4900
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 4901 AAGTGCTCATCATCGGGAATCGTTCTTCGGGGCGGAAAGACTCAAGGATCTTGCCCGCTATTGAGATCCAGTTCGATATAGCCCACTCTTGCACCCAGTTG 5000
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR
```

*Fig. 14J*

```
            5010      5020      5030      5040      5050      5060      5070      5080      5090      5100
              *         *         *         *         *         *         *         *         *         *
5001 ATCTTCAGCATCTTTTACTTTCACCAGCGTTTCGGGGTGTGCAAAAACAGGCAAGCAAAATGCCGCAAAGAAGGAATGAGTGCGACACGAAAATGTTGG 5100
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     ampR 5110      5120      5130      5140      5150      5160      5170      5180      5190      5200
              *         *         *         *         *         *         *         *         *         *
5101 ATGCTCATACTCGTCCTTTTTCAATATTATTGAAGCATTTATCAGGGTTACTAGTACGTCTCTCAAGGATAAGTAATATTAAGGTACGGGAGGTAT 5200
     <<<<<<<<
     ampR 5210      5220      5230      5240      5250      5260      5270      5280      5290      5300
              *         *         *         *         *         *         *         *         *         *
5201 TGGACAGGCCGCAATAAAATATCTTTATTTTCATTACATCTCGTGTGTGGTTTTTGTGTGAATCGATAGTACTAACATACGCTCTCCATCAAAACAAAA 5300
                              ^^^^^^^^^^^^^^^^^^^^^^^^^^^^^^^^^^^^^^^^^^
                              polyA signal sequence 5310      5320      5330      5340      5350      5360
              *         *         *         *         *         *
5301 CGAAACAAAACAAACTAGCAAAATAGGCTGTCCCCAGTGCAAGTGCAGTGCCAGAACATTTCTCT 5366
```

*Fig. 14K*

SEQUENCE LISTING

<160> NUMBER OF SEQ ID NOS: 11

<210> SEQ ID NO 1
<211> LENGTH: 413
<212> TYPE: DNA
<213> ORGANISM: Artificial Sequence

```
<220> FEATURE:
<223> OTHER INFORMATION: Synthetic DNA
<220> FEATURE:
<221> NAME/KEY: misc_feature
<222> LOCATION: (8)..(55)
<223> OTHER INFORMATION: Hammerhead ribozyme region
<220> FEATURE:
<221> NAME/KEY: misc_feature
<222> LOCATION: (51)..(58)
<223> OTHER INFORMATION: D8 complement
<220> FEATURE:
<221> NAME/KEY: misc_feature
<222> LOCATION: (59)..(63)
<223> OTHER INFORMATION: P5 complement
<220> FEATURE:
<221> NAME/KEY: misc_feature
<222> LOCATION: (93)..(98)
<223> OTHER INFORMATION: Stuffer insertion site
<220> FEATURE:
<221> NAME/KEY: misc_feature
<222> LOCATION: (99)..(106)
<223> OTHER INFORMATION: 2nd D8 complement
<220> FEATURE:
<221> NAME/KEY: misc_feature
<222> LOCATION: (107)..(111)
<223> OTHER INFORMATION: 2nd P5 complement
<220> FEATURE:
<221> NAME/KEY: misc_feature
<222> LOCATION: (126)..(172)
<223> OTHER INFORMATION: Hairpin catalytic core complement
<220> FEATURE:
<221> NAME/KEY: misc_feature
<222> LOCATION: (221)..(315)
<223> OTHER INFORMATION: Multiple cloning site
<220> FEATURE:
<221> NAME/KEY: primer_bind
<222> LOCATION: (255)..(280)
<223> OTHER INFORMATION: Primer 2 complement
<220> FEATURE:
<221> NAME/KEY: primer_bind
<222> LOCATION: (281)..(301)
<223> OTHER INFORMATION: RT primer 1 complement
<220> FEATURE:
<221> NAME/KEY: misc_feature
<222> LOCATION: (326)..(413)
<223> OTHER INFORMATION: HDV negative strand ribozyme

<400> SEQUENCE: 1
ataccctgtc accggatgtg ctttccggtc tgatgagtcc gtgaggacga aacaggactg      60
tcaggtggcc gaaagccacc acgtaaacta gtggatccaa caggactgtc agctagtcaa     120
ggcgtaccag gtaatatacc acaacgtgtg tttctctggt tgacttctct gtttgttgtg     180
tcattggttc ccggatctcg cattagcggc gacggggtat cctgcaggaa gcttggatcc     240
gtcgacgcgg ccgcgatcgt cggactgtag aactctgaac ccttggcacc cgagaattcc     300
agaattcggc gcgccatacc ctgtcgggtc ggcatggcat ctccacctcc tcgcggtccg     360
acctgggcat ccgaaggagg acagacgtcc actcggatgg ctaagggaga gcc            413

<210> SEQ ID NO 2

<400> SEQUENCE: 2

000

<210> SEQ ID NO 3
<211> LENGTH: 48
<212> TYPE: DNA
<213> ORGANISM: Satellite tobacco ringspot virus

<400> SEQUENCE: 3
gacagagaag tcaaccagag aaacacacgt tgtggtatat tacctggt                   48
```

<210> SEQ ID NO 4
<211> LENGTH: 50
<212> TYPE: DNA
<213> ORGANISM: Satellite arabis mosaic virus

<400> SEQUENCE: 4
gacagcgaag tcaaacggcg aaacacacct tgtgtggtat attacccgtt 50

<210> SEQ ID NO 5
<211> LENGTH: 50
<212> TYPE: DNA
<213> ORGANISM: Satellite chicory yellow mottle virus

<400> SEQUENCE: 5
gacagcgaag tcagccaggg aaacacacca tgtgtggtat attatctggc 50

<210> SEQ ID NO 6
<211> LENGTH: 13
<212> TYPE: DNA
<213> ORGANISM: Artificial Sequence
<220> FEATURE:
<223> OTHER INFORMATION: Synthetic DNA

<400> SEQUENCE: 6
tgaccgtcct gtc 13

<210> SEQ ID NO 7
<211> LENGTH: 13
<212> TYPE: RNA
<213> ORGANISM: Artificial Sequence
<220> FEATURE:
<223> OTHER INFORMATION: Synthetic RNA
<220> FEATURE:
<221> NAME/KEY: misc_feature
<223> OTHER INFORMATION: n=A, C, G or U
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (9)..(13)
<223> OTHER INFORMATION: n is a, c, g, or u

<400> SEQUENCE: 7
nnnnngucnn nnn 13

<210> SEQ ID NO 8
<211> LENGTH: 50
<212> TYPE: RNA
<213> ORGANISM: Artificial Sequence
<220> FEATURE:
<223> OTHER INFORMATION: Synthetic RNA
<220> FEATURE:
<221> NAME/KEY: misc_feature
<223> OTHER INFORMATION: n=A, C, G, or U; m=A or C
<220> FEATURE:
<221> NAME/KEY: misc_feature
<222> LOCATION: (1)..(5)
<223> OTHER INFORMATION: n is a, c, g, or u
<220> FEATURE:
<221> NAME/KEY: misc_feature
<222> LOCATION: (10)..(18)
<223> OTHER INFORMATION: n is a, c, g, or u
<220> FEATURE:
<221> NAME/KEY: misc_feature
<222> LOCATION: (26)..(36)
<223> OTHER INFORMATION: n is a, c, g, or u
<220> FEATURE:

```
<221> NAME/KEY: misc_feature
<222> LOCATION: (46)..(50)
<223> OTHER INFORMATION: n is a, c, g, or u

<400> SEQUENCE: 8
nnnnnmgaan nnnnnnnnag aaacannnnn nnnnnnguau auuacnnnnn          50

<210> SEQ ID NO 9
<211> LENGTH: 2190
<212> TYPE: DNA
<213> ORGANISM: Artificial Sequence
<220> FEATURE:
<223> OTHER INFORMATION: Synthetic DNA
<220> FEATURE:
<221> NAME/KEY: promoter
<222> LOCATION: (6)..(23)
<223> OTHER INFORMATION: T7 RNA promoter
<220> FEATURE:
<221> NAME/KEY: misc_feature
<222> LOCATION: (38)..(85)
<223> OTHER INFORMATION: Hammerhead ribozyme region
<220> FEATURE:
<221> NAME/KEY: misc_feature
<222> LOCATION: (81)..(88)
<223> OTHER INFORMATION: D8 complement
<220> FEATURE:
<221> NAME/KEY: misc_feature
<222> LOCATION: (89)..(93)
<223> OTHER INFORMATION: P5 complement
<220> FEATURE:
<221> NAME/KEY: misc_feature
<222> LOCATION: (123)..(128)
<223> OTHER INFORMATION: Stuffer insertion site
<220> FEATURE:
<221> NAME/KEY: misc_feature
<222> LOCATION: (129)..(136)
<223> OTHER INFORMATION: 2nd D8 complement
<220> FEATURE:
<221> NAME/KEY: misc_feature
<222> LOCATION: (137)..(141)
<223> OTHER INFORMATION: 2nd P5 complement
<220> FEATURE:
<221> NAME/KEY: misc_feature
<222> LOCATION: (156)..(202)
<223> OTHER INFORMATION: Hairpin catalytic core complement
<220> FEATURE:
<221> NAME/KEY: misc_feature
<222> LOCATION: (252)..(345)
<223> OTHER INFORMATION: Multiple cloning site
<220> FEATURE:
<221> NAME/KEY: primer_bind
<222> LOCATION: (285)..(310)
<223> OTHER INFORMATION: Primer 2 complement
<220> FEATURE:
<221> NAME/KEY: primer_bind
<222> LOCATION: (311)..(330)
<223> OTHER INFORMATION: RT primer 1 complement
<220> FEATURE:
<221> NAME/KEY: misc_feature
<222> LOCATION: (357)..(442)
<223> OTHER INFORMATION: HDV negative strand ribozyme
<220> FEATURE:
<221> NAME/KEY: rep_origin
<222> LOCATION: (451)..(1065)
<223> OTHER INFORMATION: pMB1 origin of replication in the reverse
      orientation
<220> FEATURE:
<221> NAME/KEY: primer_bind
<222> LOCATION: (502)..(525)
<223> OTHER INFORMATION: Seq2 primer binding site in the reverse
      orientation
<220> FEATURE:
<221> NAME/KEY: gene
<222> LOCATION: (1225)..(2085)
<223> OTHER INFORMATION: beta-lactamase gene in the reverse orientation
<220> FEATURE:
<221> NAME/KEY: promoter
```

```
<222> LOCATION: (2086)..(2190)
<223> OTHER INFORMATION: beta-lactamase promoter in reverse orientation
<220> FEATURE:
<221> NAME/KEY: primer_bind
<222> LOCATION: (2092)..(2121)
<223> OTHER INFORMATION: Seq1 primer binding site

<400> SEQUENCE: 9
```

| | | | | |
|---|---|---|---|---|
| agatctaata | gcactcacta | tagggatct | ataccctgtc | accggatgtg ctttccggtc | 60 |
| tgatgagtcc | gtgaggacga | aacaggactg | tcaggtggcc | gaaagccacc acgtaaacta | 120 |
| gtggatccaa | caggactgtc | agctagtcaa | ggcgtaccag | gtaatatacc acaacgtgtg | 180 |
| tttctctggt | tgacttctct | gtttgttgtg | tcattggttc | ccggatctcg cattagcggc | 240 |
| gacgggtat | cctgcaggaa | gcttggatcc | gtcgacgcgg | ccgcgatcgt cggactgtag | 300 |
| aactctgaac | ccttggcacc | cgagaattcc | agaattcggc | gcgccatacc ctgtcgggtc | 360 |
| ggcatggcat | ctccacctcc | tcgcggtccg | acctgggcat | ccgaaggagg acagacgtcc | 420 |
| actcggatgg | ctaagggaga | gccatctaga | gcgttgctg | gcgttttttcc ataggctccg | 480 |
| cccccctgac | gagcatcaca | aaaatcgacg | ctcaagtcag | aggtggcgaa acccgacagg | 540 |
| actataaaga | taccaggcgt | ttccccctgg | aagctccctc | gtgcgctctc ctgttccgac | 600 |
| cctgccgctt | accggatacc | tgtccgcctt | tctcccttcg | ggaagcgtgg cgctttctca | 660 |
| tagctcacgc | tgtaggtatc | tcagttcggt | gtaggtcgtt | cgctccaagc tgggctgtgt | 720 |
| gcacgaaccc | cccgttcagc | ccgaccgctg | cgccttatcc | ggtaactatc gtcttgagtc | 780 |
| caacccggta | agacacgact | tatcgccact | ggcagcagcc | actggtaaca ggattagcag | 840 |
| agcgaggtat | gtaggcggtg | ctacagagtt | cttgaagtgg | tggcctaact acggctacac | 900 |
| tagaagaaca | gtatttggta | tctgcgctct | gctgaagcca | gttaccttcg gaaaagagt | 960 |
| tggtagctct | tgatccggca | aacaaaccac | cgctggtagc | ggtggttttt ttgtttgcaa | 1020 |
| gcagcagatt | acgcgcagaa | aaaaaggatc | tcaagaagat | cctttgatct tttctacggg | 1080 |
| gtctgacgct | cagtggaacg | aaaactcacg | ttaagggatt | ttggtcatga gattatcaaa | 1140 |
| aaggatcttc | acctagatcc | ttttaaatta | aaaatgaagt | tttaaatcaa tctaaagtat | 1200 |
| atatgagtaa | acttggtctg | acagttacca | atgcttaatc | agtgaggcac ctatctcagc | 1260 |
| gatctgtcta | tttcgttcat | ccatagttgc | ctgactcccc | gtcgtgtaga taactacgat | 1320 |
| acgggagggc | ttaccatctg | gccccagtgc | tgcaatgata | ccgcgagacc cacgctcacc | 1380 |
| ggctccagat | ttatcagcaa | taaaccagcc | agccggaagg | gccgagcgca gaagtggtcc | 1440 |
| tgcaacttta | tccgcctcca | tccagtctat | taattgttgc | cgggaagcta gagtaagtag | 1500 |
| ttcgccagtt | aatagtttgc | gcaacgttgt | tgccattgct | acaggcatcg tggtgtcacg | 1560 |
| ctcgtcgttt | ggtatggctt | cattcagctc | cggttcccaa | cgatcaaggc gagttacatg | 1620 |
| atcccccatg | ttgtgcaaaa | aagcggttag | ctccttcggt | cctccgatcg ttgtcagaag | 1680 |
| taagttggcc | gcagtgttat | cactcatggt | tatggcagca | ctgcataatt ctcttactgt | 1740 |
| catgccatcc | gtaagatgct | tttctgtgac | tggtgagtac | tcaaccaagt cattctgaga | 1800 |
| atagtgtatg | cggcgaccga | gttgctcttg | cccggcgtca | atacgggata taccgcgcc | 1860 |
| acatagcaga | actttaaaag | tgctcatcat | tggaaaacgt | tcttcgggc gaaaactctc | 1920 |
| aaggatctta | ccgctgttga | gatccagttc | gatgtaaccc | actcgtgcac ccaactgatc | 1980 |
| ttcagcatct | tttactttca | ccagcgtttc | tgggtgagca | aaaacaggaa ggcaaaatgc | 2040 |
| cgcaaaaaag | ggaataaggg | cgacacggaa | atgttgaata | ctcatactct tccttttca | 2100 |

```
atattattga agcatttatc agggttattg tctcatgagc ggatacatat ttgaatgtat      2160
ttagaaaaat aaacaaatag gggttccgcg                                      2190

<210> SEQ ID NO 10
<211> LENGTH: 8313
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(161)
<223> OTHER INFORMATION: T-DNA right border
<220> FEATURE:
<221> NAME/KEY: promoter
<222> LOCATION: (470)..(782)
<223> OTHER INFORMATION: CaMV 35S promoter
<220> FEATURE:
<221> NAME/KEY: misc_feature
<222> LOCATION: (793)..(840)
<223> OTHER INFORMATION: Hammerhead ribozyme region
<220> FEATURE:
<221> NAME/KEY: misc_feature
<222> LOCATION: (836)..(843)
<223> OTHER INFORMATION: D8 complement
<220> FEATURE:
<221> NAME/KEY: misc_feature
<222> LOCATION: (844)..(848)
<223> OTHER INFORMATION: P5 complement
<220> FEATURE:
<221> NAME/KEY: misc_feature
<222> LOCATION: (878)..(883)
<223> OTHER INFORMATION: Stuffer insertion site
<220> FEATURE:
<221> NAME/KEY: misc_feature
<222> LOCATION: (884)..(891)
<223> OTHER INFORMATION: 2nd D8 complement
<220> FEATURE:
<221> NAME/KEY: misc_feature
<222> LOCATION: (892)..(896)
<223> OTHER INFORMATION: 2nd P5 complement
<220> FEATURE:
<221> NAME/KEY: misc_feature
<222> LOCATION: (911)..(957)
<223> OTHER INFORMATION: Hairpin catalytic core complement
<220> FEATURE:
<221> NAME/KEY: misc_feature
<222> LOCATION: (1007)..(1100)
<223> OTHER INFORMATION: Multiple cloning site
<220> FEATURE:
<221> NAME/KEY: primer_bind
<222> LOCATION: (1040)..(1065)
<220> FEATURE:
<221> NAME/KEY: primer_bind
<222> LOCATION: (1066)..(1085)
<220> FEATURE:
<221> NAME/KEY: misc_feature
<222> LOCATION: (1066)..(1085)
<223> OTHER INFORMATION: HDV negative strand ribozyme
<220> FEATURE:
<221> NAME/KEY: terminator
<222> LOCATION: (1200)..(1897)
<223> OTHER INFORMATION: CaMV 35S terminator
<220> FEATURE:
<221> NAME/KEY: gene
<222> LOCATION: (2235)..(3029)
<223> OTHER INFORMATION: neomycin phosphotransferase II gene
<220> FEATURE:
<221> NAME/KEY: rep_origin
<222> LOCATION: (2235)..(3029)
<223> OTHER INFORMATION: ColE1 origin of replication from pBR322
<220> FEATURE:
<221> NAME/KEY: misc_feature
<222> LOCATION: (3711)..(3857)
<223> OTHER INFORMATION: T-DNA left border in the reverse orientation
<220> FEATURE:
<221> NAME/KEY: rep_origin
```

```
<222> LOCATION: (4164)..(4779)
<223> OTHER INFORMATION: OriV from pRK2 in the reverse orientation
<220> FEATURE:
<221> NAME/KEY: gene
<222> LOCATION: (4878)..(6026)
<223> OTHER INFORMATION: trfA gene in the reverse orientation
<220> FEATURE:
<221> NAME/KEY: gene
<222> LOCATION: (6325)..(7119)
<223> OTHER INFORMATION: neomycin phosphotransferase III gene in the
      reverse orientation

<400> SEQUENCE: 10
cctgtggttg gcatgcacat acaaatggac gaacggataa accttttcac gccctttttaa      60 atatccgatt attctaataa acgctctttt ctcttaggtt tacccgccaa tatatcctgt     120
caaacactga tagtttgtga accatcaccc aaatcaagtt ttttggggtc gaggtgccgt     180
aaagcactaa atcggaaccc taaagggagc cccgattta gagcttgacg gggaaagccg     240
gcgaacgtgg cgagaaagga agggaagaaa gcgaaaggag cgggcgccat tcaggctgcg     300
caactgttgg gaagggcgat cggtgcgggc ctcttcgcta ttacgccagc tggcgaaagg     360
gggatgtgct gcaaggcgat taagttgggt aacgccaggg ttttcccagt cacgacgttg     420
taaaacgacg gccagtgaat tgttaattaa gaattcgagc tccaccgcgg aaacctcctc     480
ggattccatt gcccagctat ctgtcacttt attgagaaga tagtggaaaa ggaaggtggc     540
tcctacaaat gccatcattg cgataaagga aaggccatcg ttgaagatgc ctctgccgac     600
agtggtccca agatggaccc cccacccacg aggagcatcg tggaaaaaga agacgttcca     660
accacgtctt caaagcaagt ggattgatgt gatatctcca ctgacgtaag ggatgacgca     720
caatcccact atccttcgca agacccttcc tctatataag gaagttcatt tcatttggag     780
agggtatacc ctgtcaccgg atgtgctttc cggtctgatg agtccgtgag gacgaaacag     840
gactgtcagg tggccgaaag ccaccacgta aactagtgga tccaacagga ctgtcagcta     900
gtcaaggcgt accaggtaat ataccacaac gtgtgtttct ctggttgact tctctgtttg     960
ttgtgtcatt ggttcccgga tctcgcatta gcggcgacgg ggtatcctgc aggaagcttg    1020
gatccgtcga cgcggccgcg atcgtcggac tgtagaactc tgaacccttg cacccgaga    1080 attccagaat tcggcgcgcc atccctgtc gggtcggcat ggcatctcca cctcctcgcg    1140
gtccgacctg gcatccgaa ggaggacaga cgtccactcg gatggctaag ggagagccat    1200
cgaattcgct gaaatcacca gtctctctct acaaatctat ctctctctat tttctccata    1260
aataatgtgt gagtagtttc ccgataaggg aaattagggt tcttataggg tttcgctcat    1320
gtgttgagca tataagaaac ccttagtatg tatttgtatt tgtaaaatac ttctatcaat    1380
aaaatttcta attcctaaaa ccaaaatcca gtactaaaat ccagatctcc taaagtccct    1440
atagatcttt gtcgtgaata taaaccagac acgagacgac taaacctgga gcccagacgc    1500
cgttcgaagc tagaagtacc gcttaggcag gaggccgtta gggaaaagat gctaaggcag    1560
ggttggttac gttgactccc ccgtaggttt ggtttaaata tgatgaagtg gacggaagga    1620
aggaggaaga caaggaagga taaggttgca ggccctgtgc aaggtaagaa gatggaaatt    1680
tgatagaggt acgctactat acttatacta tacgctaagg gaatgcttgt atttataccc    1740
tataccccct aataacccct tatcaattta agaaataatc cgcataagcc cccgcttaaa    1800
aattggtatc agagccatga ataggtctat gaccaaaact caagaggata aaacctcacc    1860
aaaatacgaa agagttctta actctaaaga taaaagatgg cgcgtggccg gcctacagta    1920
tgagcggaga attaagggag tcacgttatg accccgccg atgacgcggg acaagccgtt    1980
```

| | |
|---|---|
| ttacgtttgg aactgacaga accgcaacgt tgaaggagcc actcagccgc gggtttctgg | 2040 |
| agtttaatga gctaagcaca tacgtcagaa accattattg cgcgttcaaa agtcgcctaa | 2100 |
| ggtcactatc agctagcaaa tatttcttgt caaaaatgct ccactgacgt tccataaatt | 2160 |
| cccctcggta tccaattaga gtctcatatt cactctcaat ccaaataatc tgcaccggat | 2220 |
| ctggatcgtt tcgcatgatt gaacaagatg gattgcacgc aggttctccg gccgcttggg | 2280 |
| tggagaggct attcggctat gactgggcac aacagacaat cggctgctct gatgccgccg | 2340 |
| tgttccggct gtcagcgcag gggcgcccgg ttcttttttgt caagaccgac ctgtccggtg | 2400 |
| ccctgaatga actgcaggac gaggcagcgc ggctatcgtg gctggccacg acgggcgttc | 2460 |
| cttgcgcagc tgtgctcgac gttgtcactg aagcgggaag ggactggctg ctattgggcg | 2520 |
| aagtgccggg gcaggatctc ctgtcatctc accttgctcc tgccgagaaa gtatccatca | 2580 |
| tggctgatgc aatgcggcgg ctgcatacgc ttgatccggc tacctgccca ttcgaccacc | 2640 |
| aagcgaaaca tcgcatcgag cgagcacgta ctcggatgga agccggtctt gtcgatcagg | 2700 |
| atgatctgga cgaagagcat caggggctcg cgccagccga actgttcgcc aggctcaagg | 2760 |
| cgcgcatgcc cgacggcgat gatctcgtcg tgacccatgg cgatgcctgc ttgccgaata | 2820 |
| tcatggtgga aaatggccgc ttttctggat tcatcgactg tggccggctg ggtgtggcgg | 2880 |
| accgctatca ggacatagcg ttggctaccc gtgatattgc tgaagagctt ggcggcgaat | 2940 |
| gggctgaccg cttcctcgtg ctttacggta tcgccgctcc cgattcgcag cgcatcgcct | 3000 |
| tctatcgcct tcttgacgag ttcttctgag cgggactctg gggttcgaaa tgaccgacca | 3060 |
| agcgacgccc aacctgccat cacgagattt cgattccacc gccgccttct atgaaaggtt | 3120 |
| gggcttcgga atcgttttcc gggacgccgg ctggatgatc ctccagcgcg ggatctcat | 3180 |
| gctggagttc ttcgcccacg gatctctgc ggaacaggcg gtcgaaggtg ccgatatcat | 3240 |
| tacgacagca acggccgaca agcacaacgc cacgatcctg agcgacaata tgatcgcggc | 3300 |
| gtccacatca acggcgtcgg cggcgactgc ccaggcaaga ccgagatgca ccgcgatatc | 3360 |
| ttgctgcgtt cggatatttt cgtggagttc ccgccacaga cccggatgat ccccgatcgt | 3420 |
| tcaaacattt ggcaataaag tttcttaaga ttgaatcctg ttgccggtct tgcgatgatt | 3480 |
| atcatataat ttctgttgaa ttacgttaag catgtaataa ttaacatgta atgcatgacg | 3540 |
| ttatttatga gatgggtttt tatgattaga gtcccgcaat tatacattta atacgcgata | 3600 |
| gaaaacaaaa tatagcgcgc aaactaggat aaattatcgc gcgcggtgtc atctatgtta | 3660 |
| ctagatcggg actgtaggcc ggccctcact ggtgaaaaga aaaaccaccc cagtacatta | 3720 |
| aaaacgtccg caatgtgtta ttaagttgtc taagcgtcaa tttgtttaca ccacaatata | 3780 |
| tcctgccacc agccagccaa cagctccccg accggcagct cggcacaaaa tcaccactcg | 3840 |
| atacaggcag cccatcagtc cgggacggcg tcagcgggag agccgttgta aggcggcaga | 3900 |
| ctttgctcat gttaccgatg ctattcggaa gaacggcaac taagctgccg ggtttgaaac | 3960 |
| acggatgatc tcgcggaggg tagcatgttg attgtaacga tgacagagcg ttgctgcctg | 4020 |
| tgatcaaata tcatctccct cgcagagatc cgaattatca gccttcttat tcatttctcg | 4080 |
| cttaaccgtg acagagtaga caggctgtct cgcggccgag gggcgcagcc cctgggggg | 4140 |
| atgggaggcc cgcgttagcg ggccgggagg gttcgagaag gggggcacc cccttcggc | 4200 |
| gtgcgcggtc acgcgcacag ggcgcagccc tggttaaaaa caaggtttat aaatattggt | 4260 |
| ttaaaagcag gttaaaagac aggttagcgg tggccgaaaa acgggcggaa acccttgcaa | 4320 |

```
atgctggatt ttctgcctgt ggacagcccc tcaaatgtca ataggtgcgc ccctcatctg    4380
tcagcactct gccccctcaag tgtcaaggat cgcgcccctc atctgtcagt agtcgcgccc    4440
ctcaagtgtc aataccgcag ggcacttatc cccaggcttg tccacatcat ctgtgggaaa    4500
ctcgcgtaaa atcaggcgtt ttcgccgatt tgcgaggctg gccagctcca cgtcgccggc    4560
cgaaatcgag cctgccccctc atctgtcaac gccgcgccgg gtgagtcggc ccctcaagtg    4620
tcaacgtccg cccctcatct gtcagtgagg gccaagtttt ccgcgaggta tccacaacgc    4680
cggcggccgc ggtgtctcgc acacggcttc gacggcgttt ctggcgcgtt tgcagggcca    4740
tagacgccg ccagcccagc ggcgagggca accagcccgg tgagcgtcgg aaaggcgctc    4800
ggtcttgcct tgctcgtcgg tgatgtacac tagtcgctgg ctgctgaacc cccagccgga    4860
actgacccca caaggcccta gcgtttgcaa tgcaccaggt catcattgac ccaggcgtgt    4920
tccaccaggc cgctgcctcg caactcttcg caggcttcgc cgacctgctc gcgccacttc    4980
ttcacgcggg tggaatccga tccgcacatg aggcggaagg tttccagctt gagcgggtac    5040
ggctcccggt gcgagctgaa atagtcgaac atccgtcggg ccgtcggcga cagcttgcgg    5100
tacttctccc atatgaattt cgtgtagtgg tcgccagcaa acagcacgac gatttcctcg    5160
tcgatcagga cctggcaacg ggacgttttc ttgccacggt ccaggacgcg gaagcggtgc    5220
agcagcgaca ccgattccag gtgcccaacg cggtcggacg tgaagcccat cgccgtcgcc    5280
tgtaggcgcg acaggcattc ctcggccttc gtgtaatacc ggccattgat cgaccagccc    5340
aggtcctggc aaagctcgta gaacgtgaag gtgatcggct cgccgatagg ggtgcgcttc    5400
gcgtactcca acacctgctg ccacaccagt tcgtcatcgt cggcccgcag ctcgacgccg    5460
gtgtaggtga tcttcacgtc cttgttgacg tggaaaatga ccttgttttg cagcgcctcg    5520
cgcgggattt tcttgttgcg cgtggtgaac agggcagagc gggccgtgtc gtttggcatc    5580
gctcgcatcg tgtccggcca cggcgcaata tcgaacaagg aaagctgcat ttccttgatc    5640
tgctgcttcg tgtgtttcag caacgcgccc tgcttggcct cgctgacctg ttttgccagg    5700
tcctcgccgg cggttttttcg cttcttggtc gtcatagttc ctcgcgtgtc gatggtcatc    5760
gacttcgcca aacctgccgc ctcctgttcg agacgacgcg aacgtccac ggcggccgat    5820
ggcgcgggca gggcagggg agccagttgc acgctgtcgc gctcgatctt ggccgtagct    5880
tgctggacca tcgagccgac ggactggaag gtttcgcggg gcgcacgcat gacggtgcgg    5940
cttgcgatgg tttcggcatc ctcggcggaa accccgcgt cgatcagttc ttgcctgtat    6000
gccttccggt caaacgtccg attcattcac cctccttgcg ggattgcccc gactcacgcc    6060
ggggcaatgt gcccttattc ctgatttgac ccgcctggtg ccttggtgtc cagataatcc    6120
accttatcgg caatgaagtc ggtcccgtag accgtctggc cgtccttctc gtacttggta    6180
ttccgaatct tgccctgcac gaataccagc gacccccttgc ccaaatactt gccgtgggcc    6240
tcggcctgag agccaaaaca cttgatgcgg aagaagtcgg tgcgctcctg cttgtcgccg    6300
gcatcgttgc gccacatcta ggtactaaaa caattcatcc agtaaaatat aatatttttat    6360
tttctcccaa tcaggcttga tccccagtaa gtcaaaaaat agctcgacat actgttcttc    6420
cccgatatcc tccctgatcg accggacgca gaaggcaatg tcataccact tgtccgccct    6480
gccgcttctc ccaagatcaa taaagccact tactttgcca tctttcacaa agatgttgct    6540
gtctcccagg tcgccgtggg aaaagacaag ttcctcttcg ggcttttccg tctttaaaaa    6600
atcatacagc tcgcgcggat ctttaaatgg agtgtcttct tcccagtttt cgcaatccac    6660
atcggccaga tcgttattca gtaagtaatc caattcggct aagcggctgt ctaagctatt    6720
```

-continued

```
cgtataggga caatccgata tgtcgatgga gtgaaagagc ctgatgcact ccgcatacag    6780
ctcgataatc ttttcagggc tttgttcatc ttcatactct tccgagcaaa ggacgccatc    6840
ggcctcactc atgagcagat tgctccagcc atcatgccgt tcaaagtgca ggacctttgg    6900
aacaggcagc tttccttcca gccatagcat catgtccttt tcccgttcca catcataggt    6960
ggtcccttta taccggctgt ccgtcatttt taaatatagg ttttcatttt ctcccaccag    7020
cttatatacc ttagcaggag acattccttc cgtatctttt acgcagcggt attttcgat    7080 cagttttttc aattccggtg atattctcat tttagccatt tattatttcc ttcctctttt    7140
ctacagtatt taaagatacc ccaagaagct aattataaca agacgaactc caattcactg    7200
ttccttgcat tctaaaacct taaataccag aaaacagctt tttcaaagtt gttttcaaag    7260
ttggcgtata acatagtatc gacggagccg attttgaaac cacaattatg ggtgatgctg    7320
ccaacttact gatttagtgt atgatggtgt ttttgaggtg ctccagtggc ttctgtttct    7380
atcagctgtc cctcctgttc agctactgac ggggtggtgc gtaacggcaa aagcaccgcc    7440
ggacatcagc gctatctctg ctctcactgc cgtaaaacat ggcaactgca gttcacttac    7500
accgcttctc aacccggtac gcaccagaaa atcattgata tggccatgaa tggcgttgga    7560
tgccgggcaa cagcccgcat tatgggcgtt ggcctcaaca cgattttacg tcacttaaaa    7620
aactcaggcc gcagtcggta actatgcggt gtgaaatacc gcacagatgc gtaaggagaa    7680
aataccgcat caggcgctct ccgcttcct cgctcactga ctcgctgcgc tcggtcgttc    7740
ggctgcggcg agcggtatca gctcactcaa aggcggtaat acggttatcc acagaatcag    7800
gggataacgc aggaaagaac atgtgagcaa aaggccagca aaaggccagg aaccgtaaaa    7860
aggccgcgtt gctggcgttt ttccataggc tccgcccccc tgacgagcat cacaaaaatc    7920
gacgctcaag tcagaggtgg cgaaacccga caggactata aagataccag gcgtttcccc    7980
ctggaagctc cctcgtgcgc tctcctgttc cgaccctgcc gcttaccgga tacctgtccg    8040
cctttctccc ttcgggaagc gtggcgcttt ctcatagctc acgctgtagg tatctcagtt    8100
cggtgtaggt cgttcgctcc aagctgggct gtgtgcacga accccccgtt cagcccgacc    8160
gctgcgcctt atccggtaac tatcgtcttg agtccaaccc ggtaagacac gacttatcgc    8220
cactggcagc aggtaacctc gcgcatacag ccgggcagtg acgtcatcgt ctgcgcggaa    8280
atggacgggc ccccggcgcc agatctgggg aac                                 8313
```

<210> SEQ ID NO 11
<211> LENGTH: 5366
<212> TYPE: DNA
<213> ORGANISM: Artificial Sequence
<220> FEATURE:
<223> OTHER INFORMATION: Synthetic DNA
<220> FEATURE:
<221> NAME/KEY: promoter
<222> LOCATION: (15)..(754)
<223> OTHER INFORMATION: CMV promoter
<220> FEATURE:
<221> NAME/KEY: misc_feature
<222> LOCATION: (866)..(913)
<223> OTHER INFORMATION: Hammerhead ribozyme region
<220> FEATURE:
<221> NAME/KEY: misc_feature
<222> LOCATION: (909)..(916)
<223> OTHER INFORMATION: D8 complement
<220> FEATURE:
<221> NAME/KEY: misc_feature
<222> LOCATION: (917)..(921)
<223> OTHER INFORMATION: P5 complement
<220> FEATURE:

```
<221> NAME/KEY: misc_feature
<222> LOCATION: (951)..(956)
<223> OTHER INFORMATION: Stuffer insertion site
<220> FEATURE:
<221> NAME/KEY: misc_feature
<222> LOCATION: (957)..(964)
<223> OTHER INFORMATION: 2nd D8 complement
<220> FEATURE:
<221> NAME/KEY: misc_feature
<222> LOCATION: (965)..(969)
<223> OTHER INFORMATION: 2nd P5 complement
<220> FEATURE:
<221> NAME/KEY: misc_feature
<222> LOCATION: (984)..(1030)
<223> OTHER INFORMATION: Hairpin catalytic core complement
<220> FEATURE:
<221> NAME/KEY: misc_feature
<222> LOCATION: (1080)..(1173)
<223> OTHER INFORMATION: Multiple cloning site
<220> FEATURE:
<221> NAME/KEY: primer_bind
<222> LOCATION: (1113)..(1138)
<223> OTHER INFORMATION: Primer 2 complement
<220> FEATURE:
<221> NAME/KEY: primer_bind
<222> LOCATION: (1139)..(1158)
<223> OTHER INFORMATION: RT primer 1 complement
<220> FEATURE:
<221> NAME/KEY: misc_feature
<222> LOCATION: (1185)..(1270)
<223> OTHER INFORMATION: HDV negative strand ribozyme
<220> FEATURE:
<221> NAME/KEY: polyA_signal
<222> LOCATION: (1313)..(1532)
<223> OTHER INFORMATION: polyA signal sequence
<220> FEATURE:
<221> NAME/KEY: promoter
<222> LOCATION: (1582)..(1998)
<223> OTHER INFORMATION: SV40 early enhancer/promoter
<220> FEATURE:
<221> NAME/KEY: gene
<222> LOCATION: (2024)..(3061)
<223> OTHER INFORMATION: hygromycin resistance gene
<220> FEATURE:
<221> NAME/KEY: rep_origin
<222> LOCATION: (3274)..(3812)
<223> OTHER INFORMATION: ColE1 origin of replication from pBR322
<220> FEATURE:
<221> NAME/KEY: gene
<222> LOCATION: (4248)..(5108)
<223> OTHER INFORMATION: beta-lactamase gene in the reverse orientation
<220> FEATURE:
<221> NAME/KEY: polyA_signal
<222> LOCATION: (5213)..(5260)
<223> OTHER INFORMATION: polyA signal sequence

<400> SEQUENCE: 11
ggcctaactg gcctcaatat tggccattag ccatattatt cattggttat atagcataaa      60
tcaatattgg ctattggcca ttgcatacgt tgtatctata tcataatatg tacatttata     120
ttggctcatg tccaatatga ccgccatgtt ggcattgatt attgactagt tattaatagt     180
aatcaattac ggggtcatta gttcatagcc catatatgga gttccgcgtt acataactta     240
cggtaaatgg cccgcctggc tgaccgccca acgacccccg cccattgacg tcaataatga     300
cgtatgttcc catagtaacg ccaataggga ctttccattg acgtcaatgg gtggagtatt     360
tacggtaaac tgcccacttg gcagtacatc aagtgtatca tatgccaagt ccgcccccta     420
ttgacgtcaa tgacggtaaa tggcccgcct ggcattatgc ccagtacatg accttacggg     480
actttcctac ttggcagtac atctacgtat tagtcatcgc tattaccatg gtgatgcggt     540
tttggcagta caccaatggg cgtggatagc ggtttgactc acggggattt ccaagtctcc     600
accccattga cgtcaatggg agtttgtttt ggcaccaaaa tcaacgggac tttccaaaat     660
```

```
gtcgtaataa ccccgccccg ttgacgcaaa tgggcggtag gcgtgtacgg tgggaggtct    720
atataagcag agctcgttta gtgaaccgtc agatcactag aagctttatt gcggtagttt    780
atcacagtta aattgctaac gcagtcagtg ggcctcggcg gccaagcttg caatccggt     840 actgttggta aagccaccat accctgtcac cggatgtgct ttccggtctg atgagtccgt    900
gaggacgaaa caggactgtc aggtggccga aagccaccac gtaaactagt ggatccaaca    960
ggactgtcag ctagtcaagg cgtaccaggt aatataccac aacgtgtgtt tctctggttg   1020
acttctctgt ttgttgtgtc attggttccc ggatctcgca ttagcggcga cggggtatcc   1080
tgcaggaagc ttggatccgt cgacgcggcc gcgatcgtcg gactgtagaa ctctgaaccc   1140
ttggcacccg agaattccag aattcggcgc gccatacct gtcgggtcgg catggcatct    1200
ccacctcctc gcggtccgac ctgggcatcc gaaggaggac agacgtccac tcggatggct   1260
aagggagagc caggccgcga ctctagagtc ggggcggccg gccgcttcga gcagacatga   1320
taagatacat tgatgagttt ggacaaacca caactagaat gcagtgaaaa aaatgcttta   1380
tttgtgaaat ttgtgatgct attgctttat ttgtaaccat tataagctgc aataaacaag   1440
ttaacaacaa caattgcatt cattttatgt ttcaggttca gggggaggtg tgggaggttt   1500
tttaaagcaa gtaaacctc tacaaatgtg gtaaaatcga taaggatccg tttgcgtatt    1560
gggcgctctt ccgctgatct gcgcagcacc atggcctgaa ataacctctg aaagaggaac   1620
ttggttagct accttctgag gcggaaagaa ccagctgtgg aatgtgtgtc agttagggtg   1680
tggaaagtcc ccaggctccc cagcaggcag aagtatgcaa agcatgcatc tcaattagtc   1740
agcaaccagg tgtggaaagt ccccaggctc cccagcaggc agaagtatgc aaagcatgca   1800
tctcaattag tcagcaacca tagtcccgcc cctaactccg cccatcccgc cctaactcc    1860 gcccagttcc gcccattctc cgccccatgg ctgactaatt ttttttattt atgcagaggc   1920
cgaggccgcc tctgcctctg agctattcca agtagtga ggaggctttt ttggaggcct    1980
aggcttttgc aaaaagctcg attcttctga cactagcgcc accatgaaga agcccgaact   2040
caccgctacc agcgttgaaa aatttctcat cgagaagttc gacagtgtga gcgacctgat   2100
gcagttgtcg gagggcgaag agagccgagc cttcagcttc gatgtcggcg gacgcggcta   2160
tgtactgcgg gtgaatagct gcgctgatgg cttctacaaa gaccgctacg tgtaccgcca   2220
cttcgccagc gctgcactac ccatcccga agtgttggac atcggcgagt tcagcgagag   2280
cctgacatac tgcatcagta gacgcgccca aggcgttact ctccaagacc tccccgaaac   2340
agagctgcct gctgtgttac agcctgtcgc gaagctatg gatgctattg ccgccgccga    2400
cctcagtcaa accagcggct tcggcccatt cgggccccaa ggcatcggcc agtacacaac   2460
ctggcgggat ttcatttgcg ccattgctga tccccatgtc taccactggc agaccgtgat   2520
ggacgacacc gtgtccgcca gcgtagctca agccctggac gaactgatgc tgtgggccga   2580
agactgtccc gaggtgcgcc acctcgtcca tgccgacttc ggcagcaaca acgtcctgac   2640
cgacaacggc cgcatcaccg ccgtaatcga ctggtccgaa gctatgttcg gggacagtca   2700
gtacgaggtg gccaacatct tcttctggcg ccctggctg gcttgcatgg agcagcagac    2760
tcgctacttc gagcgccggc atcccgagct ggccggcagc cctcgtctgc gagcctacat   2820
gctgcgcatc ggcctggatc agctctacca gagcctcgtg gacggcaact tcgacgatgc   2880
tgcctgggct caaggccgct gcgatgccat cgtccgcagc ggggccggca ccgtcggtcg   2940
cacacaaatc gctcgccgga gcgcagccgt atggaccgac ggctgcgtcg aggtgctggc   3000
```

```
cgacagcggc aaccgccggc ccagtacacg accgcgcgct aaggaggtag gtcgagttta   3060
aactctagaa ccggtcatgg ccgcaataaa atatctttat tttcattaca tctgtgtgtt   3120
ggttttttgt gtgttcgaac tagatgctgt cgaccgatgc ccttgagagc cttcaaccca   3180
gtcagctcct tccggtgggc gcggggcatg actatcgtcg ccgcacttat gactgtcttc   3240
tttatcatgc aactcgtagg acaggtgccg gcagcgctct tccgcttcct cgctcactga   3300
ctcgctgcgc tcggtcgttc ggctgcggcg agcggtatca gctcactcaa aggcggtaat   3360
acggttatcc acagaatcag gggataacgc aggaaagaac atgtgagcaa aaggccagca   3420
aaaggccagg aaccgtaaaa aggccgcgtt gctggcgttt ttccataggc tccgcccccc   3480
tgacgagcat cacaaaaatc gacgctcaag tcagaggtgg cgaaacccga caggactata   3540
aagataccag gcgtttcccc ctggaagctc cctcgtgcgc tctcctgttc cgaccctgcc   3600
gcttaccgga tacctgtccg cctttctccc ttcgggaagc gtggcgcttt ctcatagctc   3660
acgctgtagg tatctcagtt cggtgtaggt cgttcgctcc aagctgggct gtgtgcacga   3720
accccccgtt cagcccgacc gctgcgcctt atccggtaac tatcgtcttg agtccaaccc   3780
ggtaagacac gacttatcgc cactggcagc agccactggt aacaggatta gcagagcgag   3840
gtatgtaggc ggtgctacag agttcttgaa gtggtggcct aactacggct acactagaag   3900
aacagtattt ggtatctgcg ctctgctgaa gccagttacc ttcggaaaaa gagttggtag   3960
ctcttgatcc ggcaaacaaa ccaccgctgg tagcggtggt ttttttgttt gcaagcagca   4020
gattacgcgc agaaaaaaag gatctcaaga agatcctttg atcttttcta cggggtctga   4080
cgctcagtgg aacgaaaact cacgttaagg gattttggtc atgagattat caaaaaggat   4140
cttcacctag atccttttaa attaaaaatg aagttttaaa tcaatctaaa gtatatatga   4200
gtaaacttgg tctgacagcg gccgcaaatg ctaaaccact gcagtggtta ccagtgcttg   4260
atcagtgagg caccgatctc agcgatctgc ctatttcgtt cgtccatagt ggcctgactc   4320
cccgtcgtgt agatcactac gattcgtgag ggcttaccat caggccccag cgcagcaatg   4380
atgccgcgag agccgcgttc accggccccc gatttgtcag caatgaacca gccagcaggg   4440
agggccgagc gaagaagtgg tcctgctact ttgtccgcct ccatccagtc tatgagctgc   4500
tgtcgtgatg ctagagtaag aagttcgcca gtgagtagtt tccgaagagt tgtggccatt   4560
gctactggca tcgtggtatc acgctcgtcg ttcggtatgg cttcgttcaa ctctggttcc   4620
cagcggtcaa gccgggtcac atgatcaccc atattatgaa gaaatgcagt cagctcctta   4680
gggcctccga tcgttgtcag aagtaagttg gccgcggtgt tgtcgctcat ggtaatggca   4740
gcactacaca attctcttac cgtcatgcca tccgtaagat gcttttccgt gaccggcgag   4800
tactcaacca gtcgttttg tgagtagtgt atacggcgac caagctgctc ttgcccggcg   4860
tctatacggg acaacaccgc gccacatagc agtactttga aagtgctcat catcgggaat   4920
cgttcttcgg ggcggaaaga ctcaaggatc ttgccgctat tgagatccag ttcgatatag   4980
cccactcttg cacccagttg atcttcagca tcttttactt tcaccagcgt ttcggggtgt   5040
gcaaaaacag gcaagcaaaa tgccgcaaag aagggaatga gtgcgacacg aaaatgttgg   5100
atgctcatac tcgtcctttt tcaatattat tgaagcattt atcagggtta ctagtacgtc   5160
tctcaaggat aagtaagtaa tattaaggta cgggaggtat tggacaggcc gcaataaaat   5220
```

```
atctttatttt tcattacatc tgtgtgttgg tttttttgtgt gaatcgatag tactaacata    5280
cgctctccat caaaacaaaa cgaaacaaaa caaactagca aaataggctg tccccagtgc      5340
aagtgcaggt gccagaacat ttctct                                           5366
```

METHODS FOR RNA PROMOTER IDENTIFICATION

CROSS-REFERENCE TO RELATED APPLICATIONS

This application is a division of U.S. patent application Ser. No. 15/737,303 filed on Dec. 17, 2017, incorporated herein by reference in its entirety, which claims priority to, and the benefit of, PCT international application number PCT/US2016/038802, filed on Jun. 22, 2016, incorporated herein by reference in its entirety, which in turns claims priority to and the benefit of U.S. provisional application Ser. No. 62/185,060 filed on Jun. 26, 2015, incorporated herein by reference in its entirety.

INCORPORATION-BY-REFERENCE OF SEQUENCE LISTING

This application includes a sequence listing in a text file entitled "UC-2015-541-3-US-sequencelisting.txt" created on Jul. 10, 2019 and having a 29 kb file size. The sequence listing is submitted through EFS-Web and is incorporated herein by reference in its entirety.

FIELD

Provided are constructs and methods for RNA promoter identification.

BACKGROUND

Currently available technologies for identifying RNA promoters consist of individual research into viral genomic and subgenomic promoters with unknown promoters being identified by bioinformatics analysis of sequenced viral genomes to find similar regions. Generally, the sequence flanking the 5'end of an expressed subgenomic sequence is "identified" as the promoter. These methods do not yield the cloned promoter or allow promoter mutations to be evaluated.

SUMMARY

In one aspect, provided is a DNA construct. In some embodiments, DNA construct comprises the following operably linked polynucleotide elements in the 5' to 3' direction:
  i) a promoter;
  ii) a hammerhead ribozyme cleavage site;
  iii) a hammerhead ribozyme catalytic core;
  iv) a first hairpin ribozyme cleavage site in the antisense orientation;
  v) a non-functional or stuffer polynucleotide;
  vi) a second hairpin ribozyme cleavage site in the antisense orientation;
  vii) a hairpin ribozyme catalytic core in the antisense orientation;
  viii) reverse and forward primer annealing sites in the antisense orientation;
  ix) an inserted polynucleotide suspected of comprising a RNA promoter; and
  x) a third ribozyme catalytic core, wherein the third ribozyme catalytic core is in the sense orientation, is not a hairpin ribozyme catalytic core and does not comprise a hairpin ribozyme cleavage site. In some embodiments, the promoter is functional in a prokaryotic cell. In varying embodiments, the promoter functional in a prokaryotic cell comprises a bacteriophage promoter selected from the group consisting of T7, T3 and SP6. In some embodiments, the promoter is functional in a eukaryotic cell. In some embodiments, the third ribozyme catalytic core comprises a hammerhead ribozyme catalytic core without a hairpin cleavage site at its 3' end. In some embodiments, the third ribozyme catalytic core comprises a positive or negative strand hepatitis delta virus (HDV) ribozyme catalytic core. In some embodiments, the DNA construct has a length of from about 600 bp to about 1600 bp. In varying embodiments, the DNA construct has a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:1. In varying embodiments, the DNA construct has a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:9. In varying embodiments, the DNA construct has a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:10. In varying embodiments, the DNA construct has a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:11.

In a further aspect, provided is a RNA construct. In some embodiments, RNA construct comprises the following operably linked polynucleotide elements in the 5' to 3' direction:
  i) a hammerhead ribozyme catalytic core;
  ii) a first hairpin ribozyme cleavage site in the antisense orientation;
  iii) a non-functional or stuffer polynucleotide;
  iv) a second hairpin ribozyme cleavage site in the antisense orientation;
  v) a hairpin ribozyme catalytic core in the antisense orientation;
  vi) reverse and forward primer annealing sites in the antisense orientation; and
  vii) an inserted polynucleotide suspected of comprising a RNA promoter.

With respect to embodiments of the DNA and RNA constructs, in some embodiments, the hammerhead ribozyme catalytic core is from a hammerhead ribozyme selected from the group consisting of Type I, Type II, Type III, HH9 and HH10. In varying embodiments, the hammerhead ribozyme catalytic core is from a Type III hammerhead ribozyme. In varying embodiments, the first and/or second hairpin ribozyme cleavage sites have a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:7. In varying embodiments, the first and/or second hairpin ribozyme cleavage sites have a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:6. In varying embodiments, the non-functional or stuffer polynucleotide does not comprise any one of a functional RNA promoter, a primer annealing site, or a transcription modifying sequence. In varying embodiments, wherein non-functional or stuffer polynucleotide comprises from about 200 base pairs (bp) to 1000 base pairs. In varying embodiments, the hairpin ribozyme catalytic core is or is derived from (e.g., is a variant of) the negative strand self-cleavage domain of a plant virus satellite RNA selected from the group consisting of the satellite RNA of tobacco ringspot virus (sTRSV), the satellite RNA of arabis mosaic virus (sArMV), and the satellite RNA of chicory yellow mottle virus (sCYMV). In varying embodiments, the hairpin ribozyme catalytic core is derived from the negative strand self-cleavage domain of the satellite RNA of tobacco ringspot virus (sTRSV). In varying embodiments, the hairpin ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:8. In varying embodiments, the hairpin ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:3. In varying embodiments, the hairpin ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:4. In varying embodiments, the hairpin ribozyme catalytic core comprises a polynucleotide having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:5. In varying embodiments, the inserted polynucleotide suspected of comprising a RNA promoter is from a library of randomized chemically synthesized DNA sequences. In varying embodiments, the inserted polynucleotide suspected of comprising a RNA promoter is from cDNA of a RNA virus genome. In varying embodiments, the inserted polynucleotide suspected of comprising a RNA promoter is fragmented genomic DNA, e.g., from an organism. In some embodiments, the inserted polynucleotide suspected of comprising a RNA promoter comprises a mutagenized RNA promoter. In varying embodiments, the inserted polynucleotide suspected of comprising a RNA promoter is from about 50 bp to about 200 bp.

In a further aspect, provided is a DNA plasmid comprising the DNA construct as described above and herein. In some embodiments, the plasmid has a size of from about 3000 bp to about 15000 bp.

In a further aspect, provided is a polynucleotide library comprising a population of the DNA or RNA constructs described above and herein, wherein each member of the population comprises a unique insert suspected of comprising a RNA promoter.

In a further aspect, provided is a host cell comprising the DNA or RNA construct or the DNA plasmid as described above and herein. In some embodiments, the host cell expresses a RNA dependent RNA polymerase. In varying embodiments, the host cell is transfected with a polynucleotide that encodes an exogenous RNA-dependent RNA polymerase. In some embodiments, the host cell is infected with a RNA virus. In some embodiments, the host cell is infected with a RNA virus from a virus taxonomic Order selected from the group consisting of Mononegavirales, Nidovirales, Picornavirales, and Tymovirales. In varying embodiments, the host cell is infected with a RNA virus from a virus taxonomic Group selected from the group of arenaviridae, astroviridae, barnaviridae, benyviridae, bromoviridae, bunyaviridae, caliciviridae, carmotetraviridae, closteroviridae, flaviviridae, hepeviridae, leviviridae, luteoviridae, narnaviridae, nodaviridae, ophioviridae, orthomyxoviridae, permutotetraviridae, potyviridae, togaviridae, tombusviridae, virgaviridae. In varying embodiments, the host cell is infected with a RNA virus from a virus taxonomic Family selected from a group of celivirus, deltavirus, emaravirus, higrevirus, idaeovirus, ourmiavirus, polemovirus, sobemovirus, tenuivirus, umbravirus, or varicosavirus. In varying embodiments, the host cell is a prokaryotic cell or a eukaryotic cell. In varying embodiments, the host cell is selected from the group consisting of an archaeal cell, a bacterial cell, an animal cell (e.g., a mammalian cell or an insect cell), a plant cell or a fungal cell.

In a further aspect, provided is a method of identifying a RNA promoter. In some embodiments, the methods comprise the steps of:

a) transfecting a host cell with the DNA or RNA construct as described above and herein, wherein the 5' promoter is capable of promoting transcription in the host cell; wherein the host cell expresses a RNA-dependent RNA polymerase and rolling circle transcription of the RNA construct or RNA transcribed from the DNA construct within the host cell when the inserted polynucleotide comprises a functional RNA promoter yields a circularized RNA comprising:
   i) a hammerhead ribozyme catalytic core in the antisense orientation;
   ii) a hairpin ribozyme cleavage site;
   iii) a hairpin ribozyme catalytic core;
   iv) reverse and forward primer annealing sites; and
   v) the inserted polynucleotide comprising a functional RNA promoter;

b) isolating the circularized RNA;

c) amplifying the inserted polynucleotide comprising a functional RNA promoter; and d) sequencing the inserted polynucleotide comprising a functional RNA promoter, thereby identifying the RNA promoter.

In another aspect, provided is a method of identifying a RNA promoter. In some embodiments, the method comprises the steps of:

a) transcribing in vitro into RNA the DNA construct as described above and herein, thereby producing a RNA transcript of the DNA construct;

b) transfecting a host cell with the RNA transcript, wherein the host cell expresses a RNA-dependent RNA polymerase and rolling circle transcription of the RNA construct within the host cell when the inserted polynucleotide comprises a functional RNA promoter yields a circularized RNA comprising:
   i) a hammerhead ribozyme catalytic core in the antisense orientation;
   ii) a ribozyme cleavage site;
   iii) a hairpin ribozyme catalytic core;
   iv) reverse and forward primer annealing sites; and
   v) the inserted polynucleotide comprising a functional RNA promoter;

c) isolating the circularized RNA;

d) amplifying the inserted polynucleotide comprising a functional RNA promoter; and e) sequencing the inserted polynucleotide comprising a functional RNA promoter, thereby identifying the RNA promoter.

With respect to embodiments of the methods, in some embodiments, the host cell is infected with a RNA virus. In some embodiments, the host cell is infected with a RNA virus from a virus taxonomic Order selected from the group consisting of Mononegavirales, Nidovirales, Picornavirales, and Tymovirales. In varying embodiments, the host cell is transfected with a polynucleotide that encodes an exogenous RNA-dependent RNA polymerase. In varying embodiments, the host cell is infected with a RNA virus from a virus taxonomic Group selected from the group of arenaviridae, astroviridae, barnaviridae, benyviridae, bromoviridae, bunyaviridae, caliciviridae, carmotetraviridae, closteroviridae, flaviviridae, hepeviridae, leviviridae, luteoviridae, narnaviridae, nodaviridae, ophioviridae, orthomyxoviridae, permutotetraviridae, potyviridae, togaviridae, tombusviridae, virgaviridae. In varying embodiments, the host cell is infected with a RNA virus from a virus taxonomic Family selected from a group of celivirus, deltavirus, emaravirus, higrevirus, idaeovirus, ourmiavirus, polemovirus, sobemovirus, tenuivirus, umbravirus, or varicosavirus. In varying embodiments, the host cell is a prokaryotic cell or a eukaryotic cell. In varying embodiments, the host cell is selected from the group consisting of an archaeal cell, a bacterial cell, an animal cell (e.g., a mammalian cell or an insect cell), a plant cell or a fungal cell. In some embodiments, the sequencing comprises deep sequencing.

Definitions

The term "RNA promoter" refers to a promoter in a polyribonucleotide that binds to a RNA dependent RNA polymerase and leads to production of a complementary RNA transcript.

The term "ribozyme catalytic core" refers to the subsequence of a ribozyme capable of carrying out cleavage of a RNA molecule.

The term "ribozyme cleavage site" refers to the sequences recognized and cleaved by a ribozyme catalytic core.

The term "mini-monomer cassette" refers to a polynucleotide sequence comprising a ribozyme catalytic core and upstream and downstream ribozyme cleavage sites, such that when transcribed into RNA, the ribozyme catalytic core self-cleaves the mini-monomer cassette at the upstream and downstream ribozyme cleavage sites out of the context of a longer polynucleotide. The 5' and 3' ends of the excised polynucleotide ligate to form a circularized polynucleotide.

The terms "identical" or percent "identity," and variants thereof in the context of two or more polynucleotide or two or more amino acid sequences, refer to two or more sequences or subsequences that are the same. Sequences are "substantially identical" if they have a specified percentage of nucleic acid residues or amino acid residues that are the same (i.e., at least 60% identity, optionally at least 65%, 70%, 75%, 80%, 85%, 90%, 95%, 96%, 97%, 98%, or 99% identity to a reference sequence (e.g., SEQ ID NOs: 1-8) over a specified region (or the whole reference sequence when not specified)), when compared and aligned for maximum correspondence over a comparison window, or designated region as measured using any sequence comparison algorithm known in the art (GAP, BESTFIT, BLAST, Align, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990) set to default settings, or by manual alignment and visual inspection (see, e.g., Ausubel et al., Current Protocols in Molecular Biology (1995-2014). Optionally, the identity exists over a region that is at least about 100, 200, 300, 400, 500, 600, 800, 1000, or more, nucleic acids in length, or over the full-length of the sequence.

BRIEF DESCRIPTION OF THE DRAWINGS

FIG. 1A depicts a secondary structure of a sTRSV. The filled box represents the region of the RNA encoding the hammerhead ribozyme. The unfilled box represents the region of the RNA, which in the negative strand encodes the hairpin ribozyme. FIG. 1B illustrates a 126 nucleotide minimal sTRSV construct that is still capable of hammerhead ribozyme cleavage and which can be circularized by enzymatic action within cells. FIG. 1C depicts the proposed secondary structure of the Stem II region of a related satellite RNA from arabis mosaic virus (sArMV).

FIG. 4A through FIG. 4D illustrates schematically the processing steps of a construct and production of molecule for selection of RNA promoters from any source, e.g., from viral cDNA, viral genomic, organismal genomic or random sequences. The uppermost line is an insert into a plasmid appropriate for either in vitro or in vivo production of RNA. Appropriate sequences for the plasmid necessary for either in vitro or in vivo use are included as appropriate or desired, for example, T-DNA borders for use in plants. DNA molecules are shown as solid lines while RNA sequences are shown as dotted lines. The promoter (Pro) could be for in vitro production, for example, the T7 RNA polymerase promoter, or for in vivo production, for example, a plant promoter for production of the desired molecules inside plant cells. The HDV ribozyme (HDV) would be substituted for what would normally be another hammerhead ribozyme (HH). The sequences that are shaded are not functional as they are the complements of the active sequences.

FIGS. 8A-B illustrate a text map of a mini-monomer cassette sequence for RNA promoter selection.

Figure 10B:
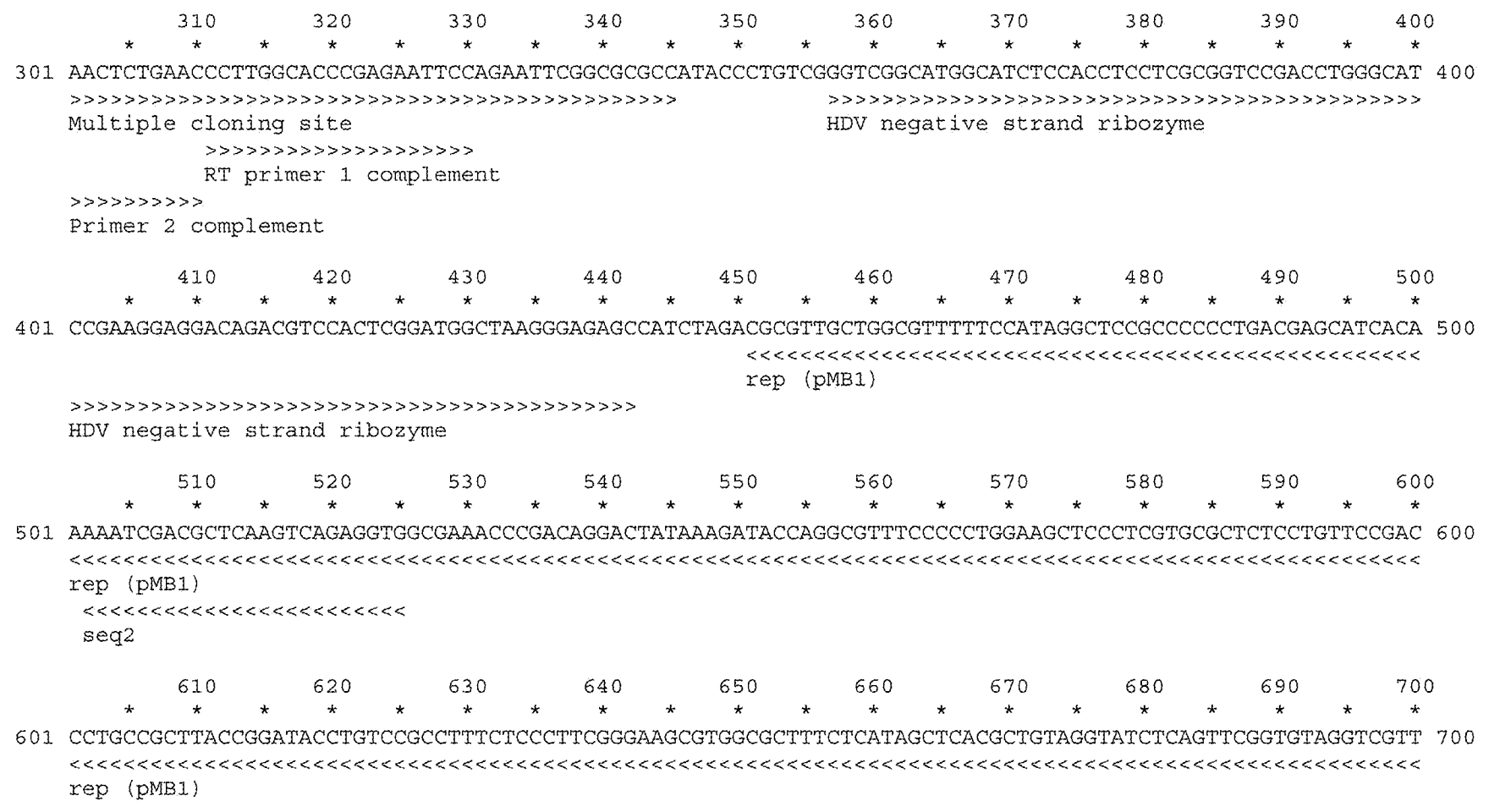

FIGS. 10A-E illustrate a text map of an in vitro production construct for MiniM cassette production for RNA promoter selection.

FIGS. 12A-P illustrate a text map of an in planta production construct for MiniM cassette production for RNA promoter selection.

FIGS. 14A-K illustrate a text map of an animal cell production construct for MiniM cassette production for RNA promoter selection.

DETAILED DESCRIPTION

1. Introduction

Provided are constructs and methods that employ hairpin ribozyme catalytic cores, e.g., such as the satellite RNA of tobacco ringspot virus (sTRSV) for identification of RNA promoters. sTRSV is a linear, 359 nucleotide, single stranded RNA which parasitizes the virus infections of its helper virus tobacco ringspot virus (TRSV). When present, it ameliorates the symptoms caused by the virus infection. It is encapsidated as a linear molecule in the virus capsid protein and uses the virus-encoded replication machinery to replicate. It has a complex secondary structure, shown in FIG. 1A that has a high degree of secondary structure.

Figure 2:
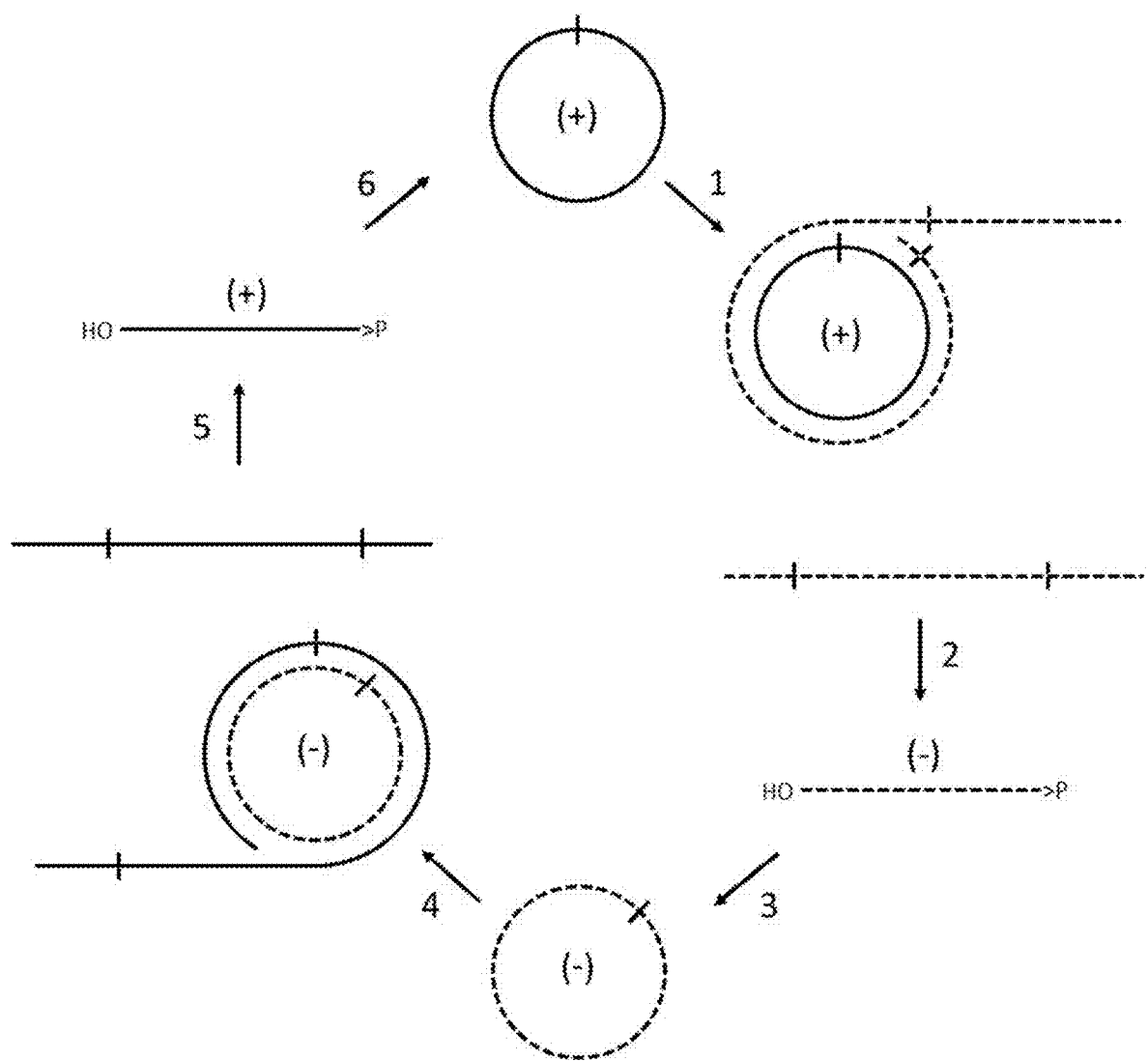
FIG. 2 illustrates the symmetrical rolling circle scheme for sTRSV replication. All sequences are RNA. The solid lines are the positive (+) strand and the dotted lines are the negative (−) strand. The positive strand is defined as that which is predominantly found in encapsidated in the viral capsids.

Within the secondary structure are two of the known ribozyme motifs—a hammerhead ribozyme (the filled box in FIG. 1A) in the positive (+) strand and a hairpin ribozyme (the unfilled boxes in FIG. 1A) in the negative (−) strand. Each is inactive when found in the complementary strand. One should also notice two things about these ribozymes, one, that while the hammerhead ribozyme is a contiguous region, the hairpin ribozyme is in two regions—the P and D regions, which function as the substrate for the more distant E region, which is the ribozyme core, and two, that the hammerhead and D region overlap by 5 nucleotides. These ribozymes play essential roles in sTRSV replication.

sTRSV replicates via a symmetrical rolling circle replication scheme as shown in FIG. 2. Linear (+) monomer sTRSV RNAs are found in the viral capsids. Inside cells this linear RNA is converted to a circular template by the action of a cellular enzyme (see, Chay, Guan and Bruening, *Virology.* (1997) 239(2):413-25) (step 6 in FIG. 2). This circular (+) sTRSV RNA is used by the TRSV helper virus RNA replication machinery as a template for rolling circle replication. Multimeric (−) sTRSV RNAs are produced (step 1 in FIG. 2). The hairpin ribozyme then cleaves these multimeric (−) sTRSV RNAs into linear (−) sTRSV monomers (step 2 in FIG. 2). Again, through the reversible action of the hairpin ribozyme, the linear (−) sTRSV monomers are circularized (step 3 in FIG. 2). The circular (−) sTRSV RNAs are then used by the viral RNA replication machinery are then used for rolling circle replication producing multimeric (+) sTRSV RNA (step 4 in FIG. 2). The hammerhead ribozyme in the (+) sTRSV RNA then cleaves the multimeric (+) sTRSV RNA into monomers (step 5 in FIG. 2), completing the cycle.

Figure 3:
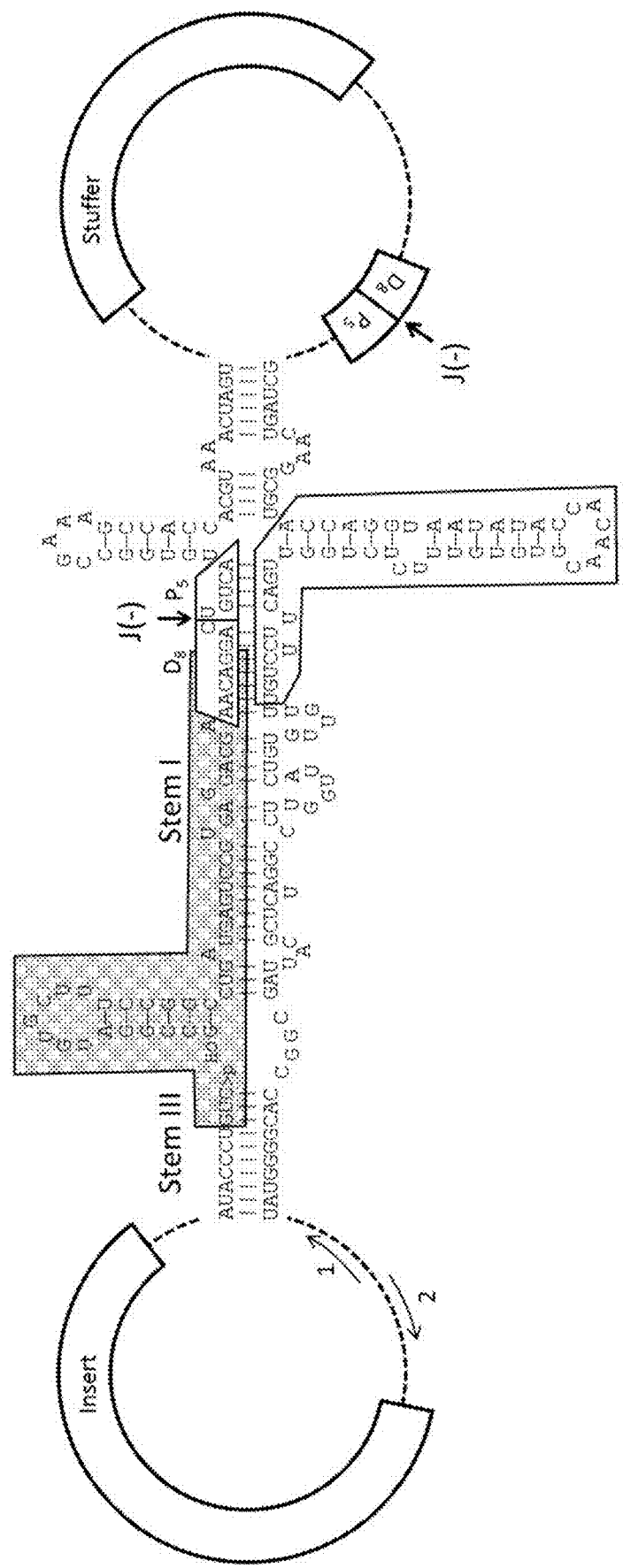
FIG. 3 illustrates a molecule for selecting RNA promoters from either viral or random sequences.

Chay, Guan and Bruening found that a much smaller construct containing the entire hammerhead region, but little else was capable of being efficiently circularized when produced inside cells (FIG. 1B). One should notice that the hairpin ribozyme core has been entirely deleted from this minimal circularizable (+) sTRSV RNA. Using this information and the smaller structure of Stem II from another related satellite RNA from arabis mosaic virus (sArMV) as shown in FIG. 1C, a molecule with the structure shown in FIG. 3 is constructed.

This molecule contains sequences for both ribozymes to function as well as the entire sequence of Stem III compared to the truncated Stem III sequence in the minimal circularizable (+) sTRSV RNA (FIG. 1B) and a truncated Stem II consistent with the structure of the sArMV sTRSV Stem II. New structures are attached to these Stem II and Stem III to form enlarged loops. The loop of the truncated Stem II contains a stuffer RNA sequence, which increases the overall size of the RNA, but provides no other function, and a second copy of the P and D regions of the hairpin ribozyme, the regions that are acted on by the ribozyme core. The loop of Stem III contains an insert sequence, which can either be fragments of viral RNA, organismal genomic or random sequences, for example 50 random nucleotides (50 Ns, where N could be any nucleotide) and primer binding sites for reverse transcriptase-polymerase chain reaction.

This molecule is produced from the construct shown in FIG. 4D. This construct can be used for in vitro production of the linear molecule shown after cleavage or the in vivo production of the circular molecule shown after enzymatic ligation. In vitro produced linear molecules are circularized by introduction into cells. Another known ribozyme, one of the two found in the hepatitis delta virus (HDV) sequence would substitute for a second hammerhead ribozyme to produce the 3' termini of the molecule. This embodiment removes the D region that is found overlapping with the hammerhead ribozyme sequence to prevent accidental formation of negative circular RNAs from spurious transcription in the opposite direction of the promoter shown (Pro) by sequences outside those shown. Transcription produces the unprocessed primary transcript followed by hammerhead and HDV ribozyme cleavage to generate the appropriate 5' and 3' termini respectively.

Production of the circular RNA or introduction of the linear RNA followed by circularization would take place in virus infected material (plants, animal cells culture, etc.). In this way, viral replication machinery is already present within the cells. In most cases, the inserted sequences within the left terminal loop do not contain a sequence that can interact with the viral replication machinery so no complementary RNA is generated. In some cases, the viral replication machinery interacts with the insert sequence and complementary sequences are generated as shown in FIG. 5. Processing of this newly synthesized primary transcript is shown in FIG. 6. The newly synthesized stuffer-containing fragments are not circularized because they do not contain a ribozyme core. The stuffer sequences also do not contain the primer binding sites and so are not recovered after RT-PCR. The newly synthesized insert-containing fragments do contain a ribozyme core and therefore are circularized and recoverable by RT-PCR with reverse and forward primers (e.g., primers 1 and 2). Deep sequencing of the insert-containing fragments identifies the sequences that are recognizable by the viral replication machinery. Subsequent rounds of selection after mutagenesis can improve the RNA promoter function.

Once selected, these viral RNA promoter molecules can be used directly as antiviral agents as they compete for viral RNA replication machinery, or the viral RNA promoters can be combined with an anti-RNA virus gene, like RNase to make a novel anti-viral gene, which is only be expressed when the virus is present. These novel anti-viral genes can be used directly as RNAs by introduction into virus-infected cells by liposome or other means, or can be used to make transgenic organisms resistant to virus infection.

2. Constructs

The constructs described herein are generally synthetic and/or recombinant. The constructs can be comprised wholly of naturally occurring nucleic acids, or in certain embodiments can contain one or more nucleic acid analogues or derivatives. The nucleic acid analogues can include backbone analogues and/or nucleic acid base analogues and/or utilize non-naturally occurring base pairs. Illustrative artificial nucleic acids that can be used in the present constructs include, without limitation, nucleic backbone analogs peptide nucleic acids (PNA), morpholino and locked nucleic acids (LNA), bridged nucleic acids (BNA), glycol nucleic acids (GNA) and threose nucleic acids (TNA). Nucleic acid base analogues that can be used in the present constructs include, without limitation, fluorescent analogs (e.g., 2-aminopurine (2-AP), 3-Methylindole (3-MI), 6-methyl isoxanthopterin (6-MI), 6-MAP, pyrrolo-dC and derivatives thereof, furan-modified bases, 1,3-Diaza-2-oxophenothiazine (tC), 1,3-diaza-2-oxophenoxazine); non-canonical bases (e.g., : inosine, thiouridine, pseudouridine, dihydrouridine, queuosine and wyosine), 2-aminoadenine, thymine analogue 2,4-difluorotoluene (F), adenine analogue 4-methylbenzimidazole (Z), isoguanine, isocytosine; diaminopyrimidine, xanthine, isoquinoline, pyrrolo[2,3-b]pyridine; 2-amino-6-(2-thienyl)purine, pyrrole-2-carbaldehyde, and universal bases (e.g., 2' deoxyinosine (hypoxanthine deoxynucleotide) derivatives, nitroazole analogues). Non-naturally occurring base pairs that can be used in the present constructs include, without limitation, isoguanine and isocytosine; diaminopyrimidine and xanthine; 2-aminoadenine and thymine; isoquinoline and pyrrolo[2,3-b]pyridine; 2-amino-6-(2-thienyl)purine and pyrrole-2-carbaldehyde; two 2,6-bis(ethylthiomethyl)pyridine (SPy) with a silver ion; pyridine-2,6-dicarboxamide (Dipam) and a mondentate pyridine (Py) with a copper ion.

Provided are constructs useful for the identification of RNA promoters, e.g., from sequences suspected of encoding a RNA promoter. The constructs can be DNA or RNA and generally comprise following operably linked polynucleotide elements in the 5' to 3' direction:

i) a hammerhead ribozyme catalytic core;
ii) a first hairpin ribozyme cleavage site in the antisense orientation;
iii) a non-functional or stuffer polynucleotide;
iv) a second hairpin ribozyme cleavage site in the antisense orientation;
v) a hairpin ribozyme catalytic core in the antisense orientation;
vi) reverse and forward primer annealing sites in the antisense orientation; and
vii) an inserted polynucleotide suspected of comprising a RNA promoter. See, FIG. 4. In varying embodiments, the DNA and/or RNA constructs have a length of about 600 bp to about 1600 bp.

a. DNA Constructs

The DNA constructs generally comprise the following operably linked polynucleotide elements in the 5' to 3' direction:

i) a promoter;
ii) a hammerhead ribozyme cleavage site;
iii) a hammerhead ribozyme catalytic core;
iv) a first hairpin ribozyme cleavage site in the antisense orientation;
v) a non-functional or stuffer polynucleotide;
vi) a second hairpin ribozyme cleavage site in the antisense orientation;
vii) a hairpin ribozyme catalytic core in the antisense orientation;
viii) reverse and forward primer annealing sites in the antisense orientation;
ix) an inserted polynucleotide suspected of comprising a RNA promoter; and
x) a third ribozyme catalytic core, wherein the third ribozyme catalytic core is in the sense orientation, is not a hairpin ribozyme catalytic core and does not comprise a hairpin ribozyme cleavage site.

i. Promoter

The 5' or upstream promoter allows transcription of the entire or full length of the construct into RNA. The ribozyme cleavage sites within the first and third ribozyme catalytic core sequences can then be cleaved by the first and third ribozyme catalytic cores, respectively.

For in vivo transcription of the full length of the construct, the selected promoter is active in a selected host cell. For example, if the DNA construct is introduced into a eukaryotic cell, the selected 5' or upstream promoter is biologically active in the eukaryotic cell. As appropriate, the 5' or upstream promoter can be a mammalian promoter that actively promotes transcription in a mammalian host cell. In some embodiments, the 5' or upstream promoter can be a plant promoter that actively promotes transcription in a plant host cell.

For in vitro transcription of the full length of the construct, the 5' or upstream promoter is any RNA polymerase promoter suitable for in vitro transcription. In varying embodiments, the 5' or upstream promoter is a bacteriophage promoter, e.g., a T7, a T3 or SP6 bacteriophage promoter.

In vivo and in vitro transcription of the DNA construct produces a RNA construct as described herein. The RNA construct may or may not be cleaved at the ribozyme cleavage sites within the first and third ribozyme cleavage sites.

ii. 5' Hammerhead Ribozyme Catalytic Core

The first and 5'-most ribozyme catalytic core is a hammerhead ribozyme catalytic core. This first and 5'-most hammerhead ribozyme catalytic core is in the positive strand orientation and includes a hammerhead ribozyme cleavage site at or near its 5'-end. The first and 5'-most hammerhead ribozyme catalytic core is positioned or located 5' to the first hairpin ribozyme cleavage site, as depicted in FIG. 4.

The minimal hammerhead sequence required for the self-cleavage reaction includes approximately 13 conserved or invariant "core" nucleotides, most of which are not involved in forming canonical Watson-Crick base-pairs. The core region is flanked by Stems I, II and III, which are in general made of canonical Watson-Crick base-pairs but are otherwise not constrained with respect to sequence. Functionally, a hammerhead ribozyme performs a chemical reaction that results in the breakage of the substrate strand of RNA, specifically at C17, the cleavage-site nucleotide.

Structurally, the hammerhead ribozyme is composed of three base paired helices, separated by short linkers of conserved sequences. These helices are called I, II and III. Hammerhead ribozymes can be classified into three types based on which helix the 5' and 3' ends are found in. If the 5' and 3' ends of the sequence contribute to stem I then it is a type I hammerhead ribozyme, to stem II is a type II and to stem III then it is a type III hammerhead ribozyme. In varying embodiments, the first and 5'-most hammerhead ribozyme catalytic core can be a Type I, Type II, Type III, HH9 and HH10 hammerhead ribozyme catalytic core.

The structure and function of hammerhead ribozymes is well-characterized in the art, and has been reviewed in, e.g., Scott, et al., *Prog Mol Biol Transl Sci*. (2013) 120:1-23; Lee, et al., *Prog Mol Biol Transl Sci*. (2013) 120:25-91; and Hammann, et al., RNA. (2012) 18(5):871-85.

iii. 5' Hammerhead Ribozyme Cleavage Site

A hammerhead ribozyme cleavage site is located or positioned within and near the 5'-end of the first and 5'-most hammerhead ribozyme catalytic core.

The hammerhead ribozyme becomes active to cleave at the hammerhead ribozyme cleavage site when the construct is RNA. As a result of cleavage at the hammerhead ribozyme cleavage site within the hammerhead ribozyme catalytic core, the 5'-product possesses a 2',3'-cyclic phosphate terminus, and the 3'-product possesses a 5'-OH terminus.

The hammerhead ribozyme is capable of cleaving immediately after a NHH sequence, where N is any nucleotide and H is an A, C or U nucleotide. There is also a structural requirement for the N and first H nucleotide to be base paired, reviewed in Kore, et al., *Nucl. Acid Res.*, (1998), 26, 4116-20.

iv. Hairpin Ribozyme Cleavage Sites

The DNA and RNA constructs comprise first (upstream) and second (downstream) antisense hairpin ribozyme cleavage sites. The first or upstream antisense ribozyme cleavage site is located 3' to or downstream of the first or upstream hammerhead ribozyme catalytic core and 5' to or upstream of the non-functional stuffer polynucleotide. The second or downstream antisense ribozyme cleavage site is located 3' to or downstream of the non-functional stuffer polynucleotide and 5' to or upstream of the antisense hairpin ribozyme catalytic core. See, FIG. 4, which depicts the primary DNA construct and primary RNA transcript.

Figure 7:
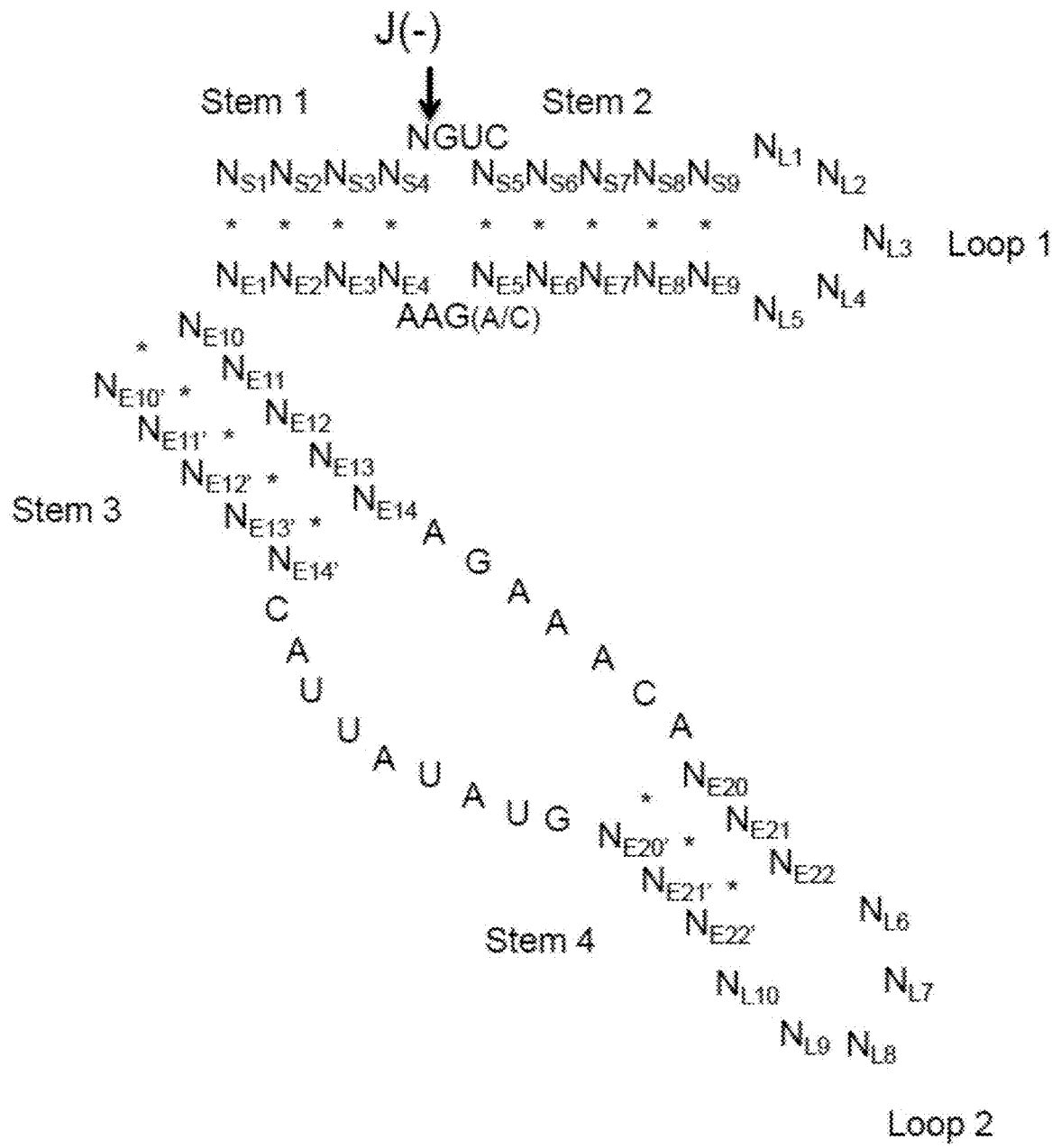
FIG. 7 illustrates a depiction of a generalized structure of the P-D regions and ribozyme core regions and their interactions.
Figure 9:
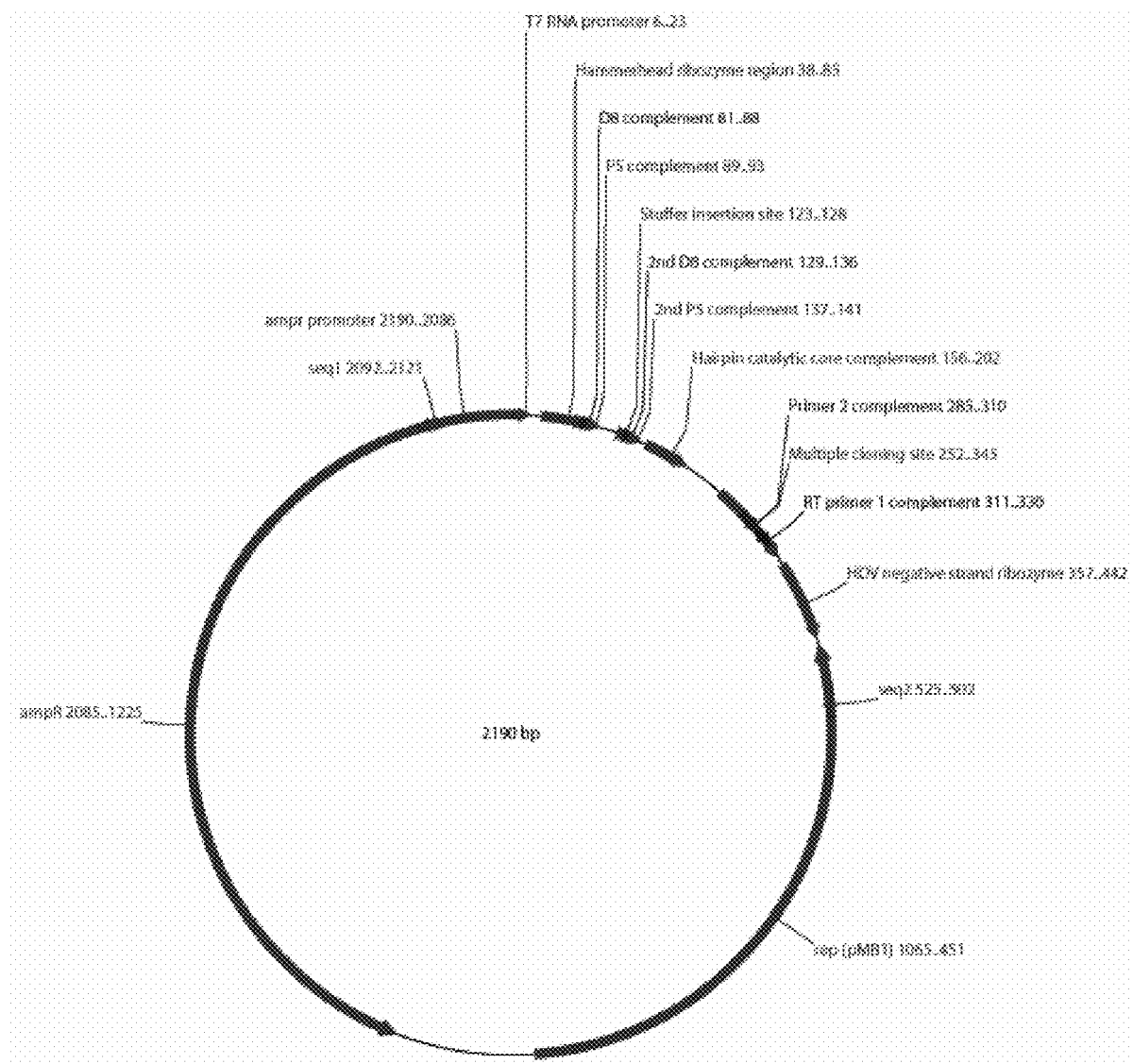
FIG. 9 illustrates a plasmid schematic of an in vitro production construct for MiniM cassette production for RNA promoter selection.
Figure 11:
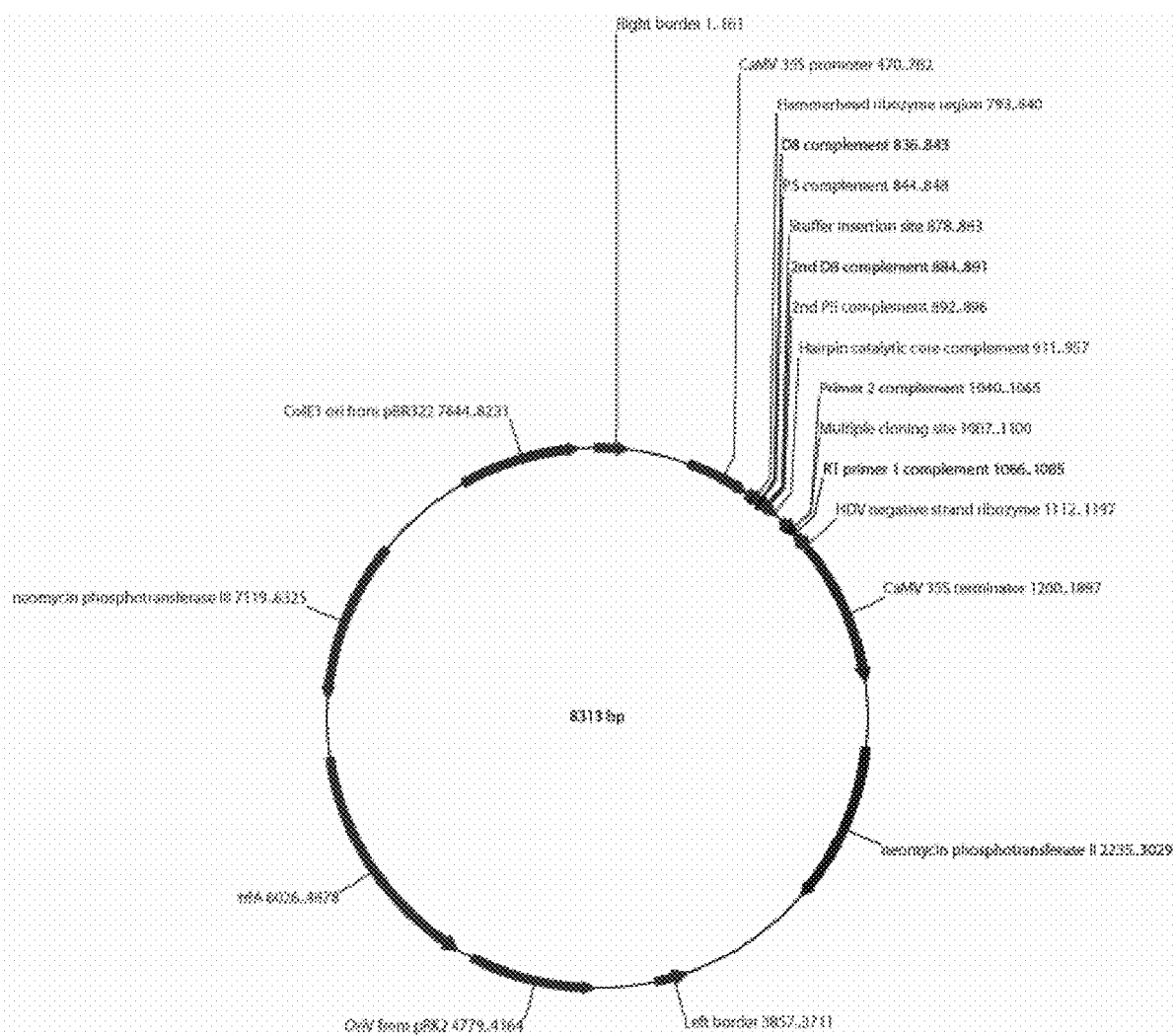
FIG. 11 illustrates a plasmid schematic of an in planta production construct for MiniM cassette production for RNA promoter selection. The illustrated in planta construct is a derivative of pEAQ-HT, a known plasmid for plant expression. See, e.g., Peyret, et al., *Plant Mol Biol.* (2013) 83(1-2):51-8.
Figure 13:
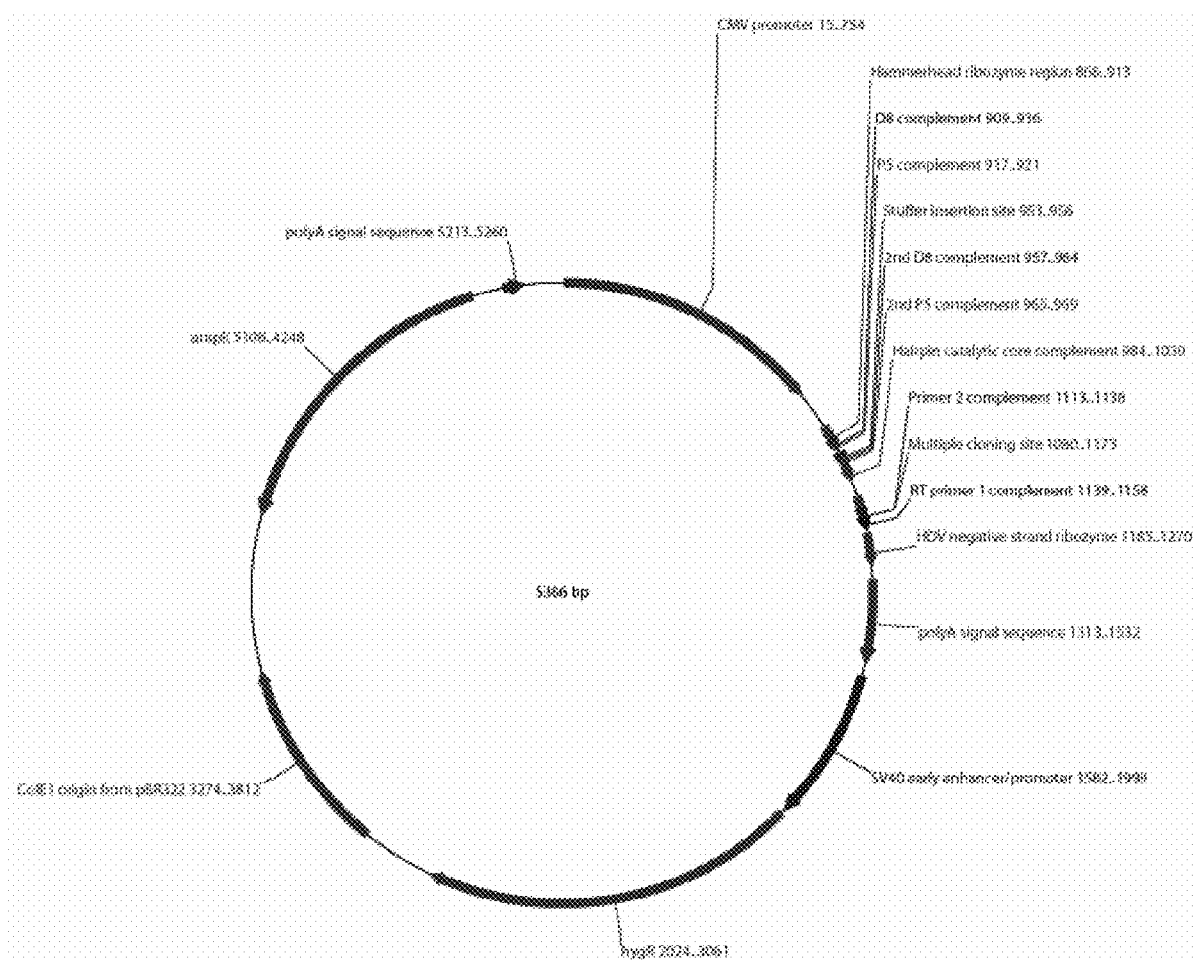
FIG. 13 illustrates a plasmid schematic of an animal cell production construct for MiniM cassette production for RNA promoter selection. The illustrated animal cell construct is a derivative of pNL 3.2, a known cytomegalovirus promoter-containing expression vector (commercially available from Promega; promega.com).

The hairpin ribozyme cleavage sites in the DNA and RNA constructs can be any polynucleotide sequence capable of being cleaved by a hairpin ribozyme. A generalized or consensus ribozyme is provided in SEQ ID NO:7. As depicted in FIG. 7, the sequence and structure of the ribozyme cleavage sites are guided by the polynucleotide sequence of the hairpin ribozyme catalytic core. Interactions between the ribozyme cleavage site (as generalized in SEQ ID NO:7) and the negative strand self-cleavage domain (as generalized in SEQ ID NO:8) are via hydrogen bonds forming two stems—1 and 2 (as depicted in FIG. 7).

Stem 1 is formed by hydrogen bonds between NS1 and NE1, NS2 and NE2, NS3 and NE3, NS4 and NE4

Stem 2 is formed by hydrogen bonds between NS5 and NE5, NS6 and NE6, NS7 and NE7, NS8 and NE8, NS9 and NE9

Interactions within the generalized negative strand self-cleavage and ligation domain form 2 stems—3 and 4

Stem 3 is formed by hydrogen bonds between NE10 and NE10', NE11 and NE11', NE12 and NE12', NE13 and NE13', NE14 and NE14'

Stem 4 is formed by hydrogen bonds between NE20 and NE20', NE21 and NE21', and NE22 and NE22'

Stem 1 is essentially universally 4 base pairs long

Stem 2 can be as short as 4 base pairs, but can be longer

Stem 3 is essentially universally 5 base pairs long

Stem 4 is from 2 to 4 base pairs long depending on the source

Loop 1 can be as small as 4 nucleotides, if it is a special sequence called a tetra-loop, but can be longer, e.g., 100's of nucleotides up to 1000 nucleotides Loop 2 varies from 4 to 6 bases long in natural sequences The polynucleotide sequences of an illustrative hairpin ribozyme cleavage site is provided herein as SEQ ID NO:6. In varying embodiments, the hairpin ribozyme cleavage site comprises a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to SEQ ID NO:6.

Generally, the polynucleotide sequences of the first and second hairpin ribozyme cleavage sites are the same.

v. Hairpin Ribozyme Catalytic Core

The DNA and RNA constructs and DNA plasmids described herein can comprise the antisense of any functional hairpin ribozyme catalytic core known in the art. The antisense hairpin ribozyme catalytic core is positioned or located 3' to or downstream of the second antisense hairpin ribozyme cleavage site and 5' to or upstream of the forward and reverse primer annealing polynucleotides. This hairpin ribozyme catalytic core is in the negative strand orientation (e.g., antisense orientation to the hammerhead ribozyme catalytic core).

The hairpin ribozyme catalytic core polynucleotides of use, when in the sense orientation, are capable of self-cleaving itself and flanking sequences within ribozyme cleavage sites out of the context of a longer polynucleotide sequence and then ligating the excised polynucleotide into a circularized polynucleotide. The hairpin ribozyme catalytic core polynucleotides are in the inactive, antisense form in the primary RNA transcript. In varying embodiments, the hairpin ribozyme catalytic core can be derived from a naturally occurring source. For example, Rubino, et al, *J Gen Virol* (1990) 71:1897-1903 describes examples of naturally-derived and consensus sequences of hairpin ribozyme catalytic core polynucleotides. In varying embodiments, the hairpin ribozyme catalytic core is or is derived from the negative strand self-cleavage domain of a satellite RNA of a plant virus, e.g., the satellite RNA of tobacco ringspot virus (sTRSV), the satellite RNA of arabis mosaic virus (sArMV), and the satellite RNA of chicory yellow mottle virus (sCYMV). In varying embodiments, the hairpin ribozyme catalytic core is or is derived from the negative strand self-cleavage domain of a satellite RNA of the plant virus tobacco ringspot virus (sTRSV). In some embodiments, the hairpin ribozyme catalytic core polynucleotide is a synthetic sequence, e.g., based on naturally occurring or consensus hairpin ribozyme catalytic core sequences. The general structure for a hairpin ribozyme catalytic core is provided in FIG. 7. The structure of hairpin ribozyme catalytic cores are well known in the art, and described, e.g., in Müller, et al., *IUBMB Life*. (2012) 64(1):36-47; Fedor, *J Mol Biol*. (2000) 297(2):269-91; and Ferré-D'Amaré, *Biopolymers*. (2004) 73(1):71-8.

In varying embodiments, the hairpin ribozyme catalytic core can be or can be derived from (e.g., can be a variant of) a circularizing ribozyme. Examples include the *Neurospora* Varkud Satellite ribozyme ("VS ribozyme") and circularizing group I intron ribozyme (e.g., circularizing introns from Tetrahymena. The structure and sequence of the VS ribozyme is known in the art, and described, e.g., in Bonneau, et al., *Biochemistry* (2014) 53(39):6264-75; Bouchard, et al., *RNA*. (2014) 20(9):1451-64; and Desjardins, et al, *Nucleic Acids Res*. (2011) 39(10):4427-37. The structure and sequence of circularizing group I intron ribozymes, including circularizing introns from *Tetrahymena* are known in the art and described, e.g., in Puttaraju and Been, *Nucl. Acid Res.* (1992), 20:5357-64; Puttaraju and Been, *J Biol Chem* (1996), 271:26081-7, Ford and Ares, *PNAS* (1994), 91:3117-21. Ribozyme structures and mechanisms are also reviewed in Doherty, et al., *Annu Rev Biochem.* (2000) 69:597-615.

A generalized or consensus negative strand self-cleavage domain of a hairpin ribozyme catalytic core is provided in SEQ ID NO:8. The polynucleotide sequences of illustrative hairpin ribozyme catalytic core molecules are provided herein as SEQ ID NOs: 3, 4 and 5. In varying embodiments, the hairpin ribozyme catalytic core comprises a polynucleotide sequence having at least about 60% sequence identity, e.g., at least about 65%, 70%, 75%, 80%, 85%, 90%, 91%, 92%, 93%, 94%, 95%, 96%, 97%, 98%, 99% or 100% sequence identity to any one of SEQ ID NOs: 3, 4 or 5.

vi. Non-Functional or Stuffer Polynucleotide

The DNA and RNA constructs comprise a non-functional or stuffer polynucleotide. Generally, the non-functional or stuffer polynucleotide does not comprise any one of a functional RNA promoter, a primer annealing site, or a transcription modifying sequence. Accordingly, the non-functional or stuffer polynucleotide does not circularize and is not amplified. Generally, the non-functional or stuffer polynucleotide is located or positioned 3' to or downstream of the first hairpin ribozyme cleavage site and 5' to or upstream of the second ribozyme cleavage site. See, e.g., FIG. 4.

In varying embodiments, the non-functional or stuffer polynucleotide comprises from about 200 base pairs (bp) to 1000 base pairs. The non-functional or stuffer polynucleotide can be any size or length such that when it is cleaved out after rolling circle replication, it is of a distinguishable size (e.g., by electrophoresis) from the cleaved out polynucleotide comprising the hammerhead ribozyme catalytic core, insert containing a RNA promoter, primer annealing polynucleotides and hairpin ribozyme catalytic core. See, FIG. 6.

vii. Forward and Reverse RT-PCR Primer Annealing Polynucleotides

The DNA and RNA constructs comprise forward and reverse RT-PCR primer annealing polynucleotides. The forward and reverse RT-PCR primer annealing polynucleotides are each unique sequences in the constructs or DNA plasmids and generally abut each other or are located proximally to each other (e.g., within about 500, 400, 300, 200 or 100 nucleotides from one another) with the reverse RT-PCR primer annealing polynucleotide positioned 5' to the forward RT-PCR primer annealing polynucleotide. The forward and reverse RT-PCR primer annealing polynucleotides are positioned or located such that they are between the two ribozyme cleavage sites (e.g., the P-D regions) so they are excised as part of the mini-monomer cassette, and they face each other across the P-D region formed from the first and second P-D regions by ribozyme cleavage and ligation. The PCR product they make contains the insert region. In varying embodiments, the forward and reverse RT-PCR primer annealing polynucleotides are positioned or located such that they are 5' to or upstream of the insert suspected of containing a RNA promoter and 3' to or downstream of the hairpin ribozyme catalytic core. See, e.g., FIG. 4.

viii. Inserted Polynucleotide Suspected of Comprising a RNA Promoter

The DNA and RNA constructs comprise an inserted polynucleotide suspected of comprising a RNA promoter. The inserted polynucleotide suspected of comprising a RNA promoter is positioned or located 3' to or downstream of the forward and reverse primer annealing polynucleotides and 5' to or upstream of the third ribozyme catalytic core.

The inserted polynucleotide suspected of comprising a RNA promoter can be from any source, for example, a randomly generated library, a naturally occurring source (e.g., a genomic library), a chemically synthesized source, a mutated or mutagenized known RNA promoter, random polynucleotides, restriction fragments of eukaryotic DNA, or randomized PCR fragments of eukaryotic DNA. In varying embodiments, the inserted polynucleotide suspected of comprising a RNA promoter is variously fragmented genomic DNA from an organism, e.g., there may be RNA promoters present in genomic DNA. Generally, the polynucleotide suspected of comprising a promoter has from about 50 bp to about 200 bp. In varying embodiments, the polynucleotide suspected of comprising a promoter contains an entire promoter or a partial promoter. Within the inserted or captured polynucleotide suspected of comprising a promoter, the promoter may be centered or located more proximal to the 3' or 5' end. The methods of employing the DNA constructs described herein identify functional promoters, e.g., promoters capable of inducing, directing or promoting transcription, regardless of whether the entire promoter or a partial promoter is captured, or the location of the RNA promoter within the captured insert.

ix. Third Ribozyme Catalytic Core

The third ribozyme catalytic core is located or positioned 3' to or downstream of the inserted polynucleotide suspected of comprising a RNA promoter. The third or 3' ribozyme catalytic core is not a hairpin ribozyme catalytic core but can be in varying embodiments a hammerhead ribozyme catalytic core so long as the hammerhead ribozyme catalytic core does not comprise a hairpin cleavage site at its 3' end. Generally, the third ribozyme catalytic core is in the positive strand orientation (e.g., same or sense orientation to the hammerhead ribozyme catalytic core). In varying embodiments, the third ribozyme catalytic core comprises a positive or negative strand hepatitis delta virus (HDV) ribozyme catalytic core or a ribozyme catalytic core from a member of the HDV family. The structure of hepatitis delta virus (HDV) and HDV family members are known in the art. See, e.g., Riccitelli, et al., *Prog Mol Biol Transl Sci.* (2013) 120:123-71; Kapral, et al., *Nucleic Acids Res.* (2014) 42(20):12833-46.

Consensus sequences for the HDV negative strand (antigenomic) ribozyme has been examined by Nehdi and Perreault, *Nucl. Acid Res.* (2006) 34:584-92, and for the HDV positive strand (genomic) ribozyme has been examined by Chadalavada et al., *RNA* (2007) 13:2189-2201. General aspects of the HDV ribozyme structures and mechanisms of action are reviewed in Doherty and Doudna, *Ann. Rev. Biochem.* (2000) 69:597-615.

b. RNA Constructs

The DNA constructs generally comprise the following operably linked polynucleotide elements in the 5' to 3' direction:

i) a hammerhead ribozyme catalytic core;

ii) a first hairpin ribozyme cleavage site in the antisense orientation;

iii) a non-functional or stuffer polynucleotide;

iv) a second hairpin ribozyme cleavage site in the antisense orientation;

v) a hairpin ribozyme catalytic core in the antisense orientation;

vi) reverse and forward primer annealing sites in the antisense orientation; and vii) an inserted polynucleotide suspected of comprising a RNA promoter. Embodiments of the hammerhead ribozyme catalytic core, the hairpin ribozyme cleavage sites, the non-functional or stuffer polynucleotide, the hairpin ribozyme catalytic core, the reverse and forward primer annealing sites and inserted polynucleotide suspected of comprising a RNA promoter are as described above for the DNA constructs. In addition, the RNA constructs comprise a hydroxyl group at the 5'-end and a 2':3' cyclic phosphodiester at the 3'-end in order to get cyclization of the RNA inside a host cell.

3. Plasmids and Viral Replicating Vectors

Further provided are DNA plasmids and viral replicating vectors comprising the DNA constructs described above and herein. In varying embodiments, the entire size of the DNA plasmids that are designed for screening and identifying functional RNA promoter sequences is from about 3000 bp to about 15,000 bp. Generally, the plasmid backbone comprises an origin of replication and an expression cassette for expressing a selection gene. In varying embodiments, the expression cassette for expressing a selection gene is in the antisense orientation from the 5' hammerhead ribozyme catalytic core. The selection gene can be any marker known in the art for selection of a host cell that has been transformed with a desired plasmid. In varying embodiments, the selection marker comprises a polynucleotide encoding a gene or protein conferring antibiotic resistance, heat tolerance, fluorescence, or luminescence.

Viral replicating vectors can be used to express the DNA or RNA constructs as described. Due to the presence of ribozymes in both strands of the RNA constructs, RNA virus vectors can be used by implementing adjustments to the RNA constructs. In planta, geminiviruses are a representative DNA virus that can be used as an expression system. Reviewed in, e.g., Hefferon, *Vaccines* (2014) 2:642-53. In animal cells, there are more choices. Plasmid expression constructs containing viral origins of replication, while not truly viral replicating systems, are stably maintained in cells. Truly replicating viral systems of use include without limitation, e.g., adenovirus, adeno-associated virus, baculovirus, and Vaccinia virus vectors, which are known in the art.

4. Host Cells

Further provided are host cells comprising the DNA or RNA constructs as described above and herein.

In varying embodiments, the host cell expresses a RNA dependent RNA polymerase. For example, in some embodiments, the host cell is transfected with a polynucleotide that encodes an exogenous RNA-dependent RNA polymerase. In some embodiments, the host cell is infected with a RNA virus. Illustrative RNA viruses include a virus of the taxonomic Orders Mononegavirales, Nidovirales, Picornavirales, and Tymovirales. Further illustrative RNA viruses include a virus of the taxonomic Groups arenaviridae, astroviridae, barnaviridae, benyviridae, bromoviridae, bunyaviridae, caliciviridae, carmotetraviridae, closteroviridae, flaviviridae, hepeviridae, leviviridae, luteoviridae, narnaviridae, nodaviridae, ophioviridae, orthomyxoviridae, permutotetraviridae, potyviridae, togaviridae, tombusviridae, and virgaviridae. Further illustrative RNA viruses include a virus of the taxonomic Family celivirus, deltavirus, emaravirus, higrevirus, idaeovirus, ourmiavirus, polemovirus, sobemovirus, tenuivirus, umbravirus, or varicosavirus.

In varying embodiments, the host cell is a prokaryotic cell, e.g, a bacterial cell, an archaeal cell, or an archaebacterial cell. In varying embodiments, the host cell is a eukaryotic cell, e.g., an animal cell (e.g., a mammalian cell or an insect cell), a plant cell or a fungal cell.

Illustrative plant cells include without limitation, e.g., Brassicaceae, Solanaceae, Phaseoleae, Zea and Oryzeae.

5. Methods of Identifying RNA Promoters

Further provided are methods of identifying RNA Promoters. In the first instance, the methods employ one or more of the DNA or RNA constructs and one or more host cells, the embodiments of which are described above and herein.

In varying embodiments, the methods entail the following steps:

a) transfecting a host cell with the DNA or RNA construct as described above and herein, wherein the 5' promoter is capable of promoting transcription in the host cell; wherein the host cell expresses a RNA-dependent RNA polymerase and rolling circle transcription of the RNA construct or RNA transcribed from the DNA construct within the host cell when the inserted polynucleotide comprises a functional RNA promoter yields a circularized RNA comprising:
  i) a hammerhead ribozyme catalytic core in the antisense orientation;
  ii) a hairpin ribozyme cleavage site;
  iii) a hairpin ribozyme catalytic core;
  iv) reverse and forward primer annealing sites; and
  v) the inserted polynucleotide comprising a functional RNA promoter;

b) isolating the circularized RNA;

c) amplifying the inserted polynucleotide comprising a functional RNA promoter; and d) sequencing the inserted polynucleotide comprising a functional RNA promoter, thereby identifying the RNA promoter.

In varying embodiments, the methods entail the following steps:

a) transcribing in vitro into RNA the DNA construct as described above and herein, thereby producing a RNA transcript of the DNA construct;

b) transfecting a host cell with the RNA transcript, wherein the host cell expresses a RNA-dependent RNA polymerase and rolling circle transcription of the RNA construct within the host cell when the inserted polynucleotide comprises a functional RNA promoter yields a circularized RNA comprising:
  i) a hammerhead ribozyme catalytic core in the antisense orientation;
  ii) a ribozyme cleavage site;
  iii) a hairpin ribozyme catalytic core;
  iv) reverse and forward primer annealing sites; and
  v) the inserted polynucleotide comprising a functional RNA promoter;

c) isolating the circularized RNA;

d) amplifying the inserted polynucleotide comprising a functional RNA promoter; and e) sequencing the inserted polynucleotide comprising a functional RNA promoter, thereby identifying the RNA promoter.

a. Transcribing In Vitro into RNA the DNA Construct

In varying embodiments, the one or more DNA constructs, as described above and herein, are first transcribed in vitro into RNA and then the RNA transcript is transfected into a host cell. The step of transcribing the one or more DNA constructs into RNA in vitro can be performed using any methodologies known in the art. In vitro transcription of one or more (e.g., a population of) DNA constructs comprising a library of inserts suspected of comprising a functional RNA promoter sequence can be achieved using purified RNA polymerases, e.g. T7 RNA polymerase. Such methodologies are described, e.g., in Green and Sambrook, Molecular Cloning, A Laboratory Manual, 4th Ed., Cold Spring Harbor Press, (2012). A schematic of the starting material DNA construct is depicted in FIG. 4A. The transcribed RNA construct is depicted in FIG. 4B. Cleavage will take place producing the RNA depicted in FIG. 4C. The in vitro transcribed and cleaved RNA construct remains linear. The final construct may be circularized as depicted in FIG. 4D after enzymatic ligation of the processed construct shown in FIG. 4C.

b. Transfecting a Host Cell with the DNA or RNA Construct

In varying embodiments, the DNA construct or the in vitro transcribed RNA construct is transfected into a suitable host cell of closed circular DNA plasmid using any method known in the art, e.g., by electroporation of protoplasts, fusion of liposomes to cell membranes, cell transfection methods using calcium ions or PEG, use of gold or tungsten microparticles coated with plasmid with the gene gun. Such methodologies are described, e.g., in Green and Sambrook, Molecular Cloning, A Laboratory Manual, 4th Ed., Cold Spring Harbor Press, (2012). As discussed above, the cells of all eukaryotic organisms (plants, animals, fungi, etc.) can be used. In varying embodiments, the host cell is a prokaryotic cell, e.g, a bacterial cell, an archaeal cell, or an archaebacterial cell.

Figure 5:
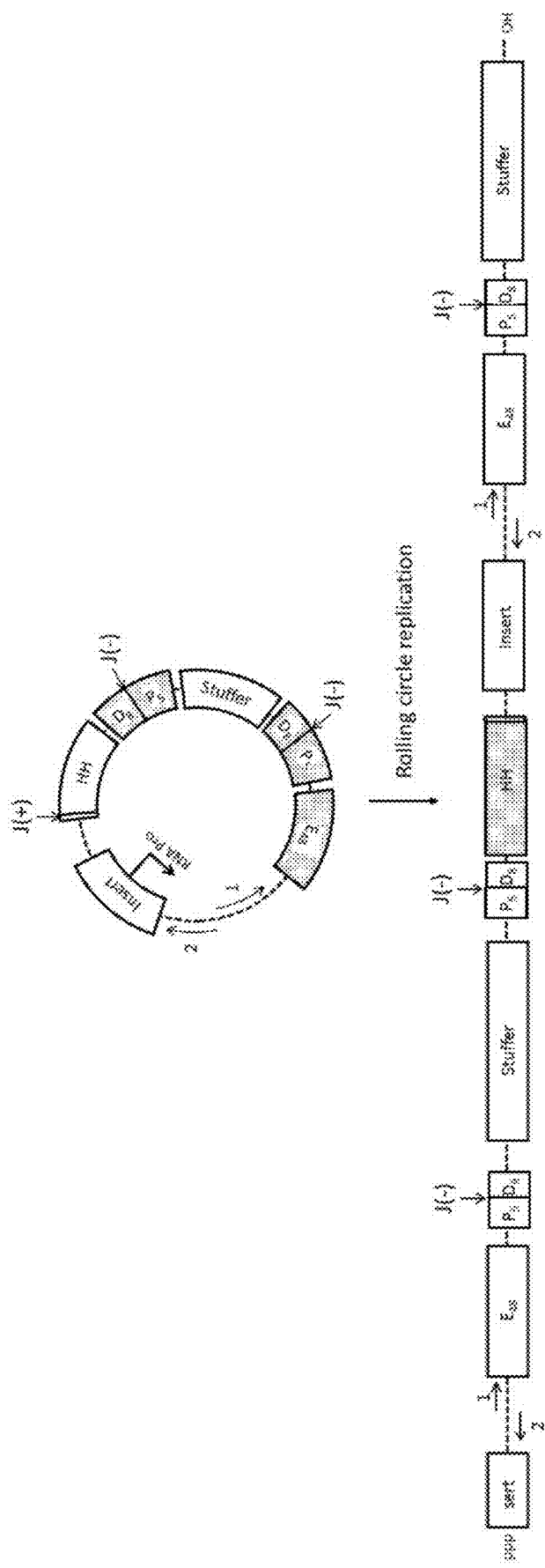
FIG. 5 illustrates rolling circle replication of the molecule for selection of RNA promoters. In the circular molecule, the 5' to 3' direction is clockwise on the circle. In the linear multimer produced by replication of the circular molecule the 5' to 3' direction is from left to right. The 5' most sequence of the new RNA synthesized is a fragment of the insert sequence. While the newly synthesized RNA is shown only through the second stuffer sequence, it is shown this way for convenience only and should be longer than this depending on the ability of the viral replication machinery to synthesize longer RNAs. Notice that in the newly synthesized RNA the hammerhead sequences (HH) are shaded (non-functional due to being the complementary sequence) and the E, P and D sequences are not shaded (functional).
Figure 6:
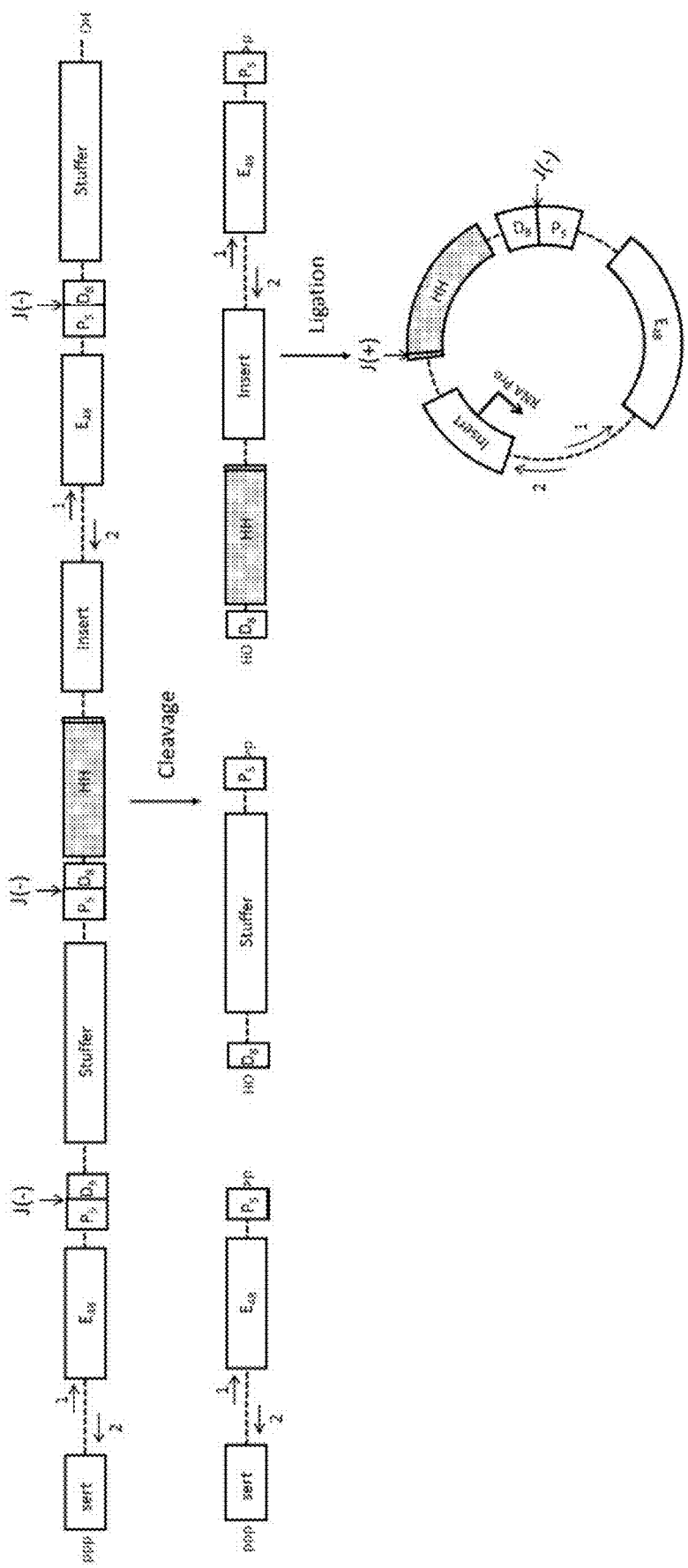
FIG. 6 illustrates processing of the newly synthesized primary transcript. The primary transcript is shown at the top with the fully processed products are below it. For every one of the 5' most fragment, there should be multiple stuffer and insert fragments.

In vitro produced linear molecules are circularized by introduction into cells. Production of the circular RNA or introduction of the linear RNA followed by circularization occurs in a host cell that expresses a RNA dependent RNA promoter. In varying embodiments, the host cell is infected with a RNA virus, as described above. In this way, viral replication machinery is already present within the transfected host cells. In most cases, the insert sequences suspected of comprising a RNA promoter (e.g., within the left terminal loop) do not contain a sequence that can interact with the viral replication machinery so no complementary RNA is generated. In some cases, the viral replication machinery will interact with the insert sequence suspected of comprising a RNA promoter and complementary sequences will be generated as shown in FIG. 5. Constructs having inserts that actually contain a RNA promoter construct undergo rolling circle replication. The mini-monomer cassette polynucleotide subsequences containing the hairpin ribozyme catalytic core, the insert containing a RNA promoter and the RT-PCR primer annealing sites are cleaved by the hairpin ribozyme catalytic core and circularize. Processing of this newly synthesized primary transcript is shown in FIG. 6. In contrast, the newly synthesized stuffer-containing fragments are not circularized because they do not contain a hairpin ribozyme catalytic core. Further the stuffer-containing fragments do not contain the primer binding sites and so are not recovered after RT-PCR.

c. Isolating the Circularized RNA

The step of isolating the circularized RNA molecules can be performed using one of many methodologies known in the art. Such methodologies are described, e.g., in Green and Sambrook, Molecular Cloning, A Laboratory Manual, 4th Ed., Cold Spring Harbor Press, (2012).

d. Amplifying the Inserted Polynucleotide Comprising a Functional RNA Promoter

The inserts containing a RNA promoter sequence in the circularized RNA molecules are amplified by RT-PCR, usually from the forward and reverse RT-PCR primer annealing polynucleotides. The step of reverse-transcribing the inserts containing a RNA promoter sequence in the circularized RNA molecules into cDNA can be performed using any methodologies known in the art. Such methodologies are described, e.g., in Green and Sambrook, Molecular Cloning, A Laboratory Manual, 4th Ed., Cold Spring Harbor Press, (2012).

cDNA can be synthesized from reverse transcription of the RNA of circularized and self-cleaved mini-monomer carrying a functional promoter (e.g., eukaryotic or prokaryotic) using a primer that binds at the reverse RT-PCR primer annealing sequence. Reverse transcription can be followed by PCR with the forward and reverse primers, thereby yielding a PCR product containing the mini-monomer sequence with the RNA promoter-containing insert if the RNA template for reverse transcription is circular. Because production and processing of the circularized RNA molecules requires initiation of transcription from a RNA promoter in the original linear construct, RT-PCR-derived cDNAs can only be produced if a cloned DNA insert contains a functional RNA promoter.

e. Sequencing the Inserted Polynucleotide Comprising a Functional RNA Promoter

The step of sequencing the inserted polynucleotides comprising a functional RNA promoter in the DNA polynucleotides amplified from the isolated circularized RNA can be performed using any methodologies known in the art. Such methodologies are described, e.g., in Green and Sambrook, Molecular Cloning, A Laboratory Manual, 4th Ed., Cold Spring Harbor Press, (2012). In varying embodiments, next generation sequencing, deep sequencing or ultra deep sequencing methodologies are applied. Deep sequencing data analysis is described, e.g., in "Deep Sequencing Data Analysis (Methods in Molecular Biology)," Noam Shomron (Editor), Humana Press; 2013 edition. Next generation sequencing is described, e.g., in "Next-Generation DNA Sequencing Informatics," Stuart M. Brown (Editor), Cold Spring Harbor Laboratory Press; 1st edition (2013); and "Next-generation Sequencing: Current Technologies and Applications," Jianping Xu (Editor), Caister Academic Press (2014); Wilhelm, et al., *Nature*. (2008) 453:1239-1243; Nagalakshmi, et al., *Science*. (2008) 320:1344-1349; and Mortazavi, et al., *Nat. Methods*. (2008) 5:621-628.

f. Exposure to External Influences

In varying embodiments, de novo selection and subsequent evolution of externally influenced RNA promoter sequences is performed. Using a library containing inserted polynucleotides suspected of comprising a RNA promoter sequence, as described above, insertion of this library into cells with or without some external factor $Ca^{++}$ ions, salt, temperature stress, hormones, etc.), followed by analysis as described previously will allow detection of sequences that are increased preferentially in the presence of the external factor. Analysis of these sequences allows determination of common features that can make the significant structural features more obvious. Reconstruction of a library of mutagenized sequences related to these initial sequences followed by reanalysis, again in the presence or absence of the external factor, will allow an evolutionary optimization of said RNA promoter sequences, ultimately leading to the selection of a de novo optimized RNA promoter sequence that can be used in the construction of novel promoters or modified genes that are responsive to the external factor in question.

g. Methods of Identifying Modifying RNA Promoter Sequences

The methods described herein can be used to identify functional RNA promoter sequences derived from known RNA promoter sequences, but having increased or decreased RNA transcriptional efficiencies or strengths. In varying embodiments, the insert suspected of comprising a RNA promoter sequence comprises a known RNA promoter sequence that has been mutated or mutagenized. The methods of RNA promoter sequence identification described above and herein allow one to take a known RNA promoter sequence, mutagenize it, then run the mutagenized sequences through the RNA promoter sequences selection procedure, thereby generating a quasispecies of new RNA promoter sequences with a range of RNA promoter sequences strengths (ability to increase or decrease RNA transcriptional efficiencies or strengths). This procedure can be done iteratively or generationally (e.g., providing a population of polynucleotides comprising mutagenized promoters, selecting for RNA promoter sequences having increased or decreased transcription efficiency (as desired), recovering RT-PCR products, performing one or more further rounds of mutagenesis and then performing the steps of the methods again, as many iterations as necessary or desired).

6. Kits

Further provided are kits containing one or more of the DNA and/or RNA constructs described herein. In varying embodiments, the kits can further comprise in one or more containers or vessels buffers, reagents, nucleotides, enzymes, control polynucleotides, host cells as described herein, and instructions for use. In varying embodiments, the kits comprise a library of DNA and/or RNA constructs for use in screening for RNA promoters, wherein each member of the library is pre-loaded with an inserted polynucleotide suspected of comprising a RNA promoter.

EXAMPLES

The following examples are offered to illustrate, but not to limit the claimed invention.

Example 1

Selection of an RNA Promoter from a Randomized DNA Library

This example illustrates the selection of a RNA promoter from a library of randomized DNA.

Two oligonucleotides are synthesized—one oligonucleotide containing a restriction endonuclease cleavage site, 50 N residues, where N can be any nucleotide, a specific sequence 3' to the 50 N residues and a second restriction endonuclease cleavage sites and a second oligonucleotide containing the complement of the specific sequence and second restriction endonuclease cleavage site. The two oligonucleotides are hybridized, made double stranded and cloned into a plasmid forming a construct of as shown in FIG. 4A using methods known to someone skilled in the art. If in vitro production of the RNA is to be performed, the plasmid may contain a T7 or other bacteriophage RNA polymerase promoter. If in vivo production of the RNA is to be performed, the plasmid can contain an appropriate promoter as well as any other necessary sequences appropriate for the in vivo environment being used, e.g. Left and Right T-DNA borders for *Agrobacterium*-mediated transient expression in plant cells.

In vitro produced RNA is purified, e.g., using phenol/chloroform/iso-amyl alcohol extraction and ethanol precipitation. The in vitro produced RNA may be introduced into cells already infected with the RNA virus for which the RNA promoter is being sought. If in vivo production is done, a construct using a eukaryotic promoter appropriate for a particular cell or organism type may be used. Alternatively, intracellular production of the viral RNA dependent RNA polymerase in the cells may be done. At various times after introduction, e.g. at 12 hours, 24 hours, 48 hours and 72 hours, total RNA are extracted from the cells into which the in vitro produced RNAs were introduced, e.g., using such methods as a Trizol reagent protocol or a commercial RNA extraction kit. This RNA is used directly for further steps. Alternatively, any circular RNAs is purified, e.g., using 2-D polyacrylamide gel electrophoresis. Complementary DNA (cDNA) is synthesized, e.g., by hybridizing an oligonucleotide to the RNA followed by reverse transcription, e.g., using an enzyme such as SuperScript II or Superscript III. PCR is performed to amplify any synthesized cDNA using a set of oligonucleotide primers that only amplifies the complementary RNA that was circularized by hairpin ribozyme ligation. To ensure that any newly synthesized complementary RNA is generated by the virus replication machinery, a control experiment can be performed in uninfected cells. Sequencing of the amplified cDNA sequences from both virus-infected and uninfected cells followed by a comparison of any sequences recovered from said cells identifies those sequences that are uniquely present in the virus-infect cells. These unique sequences can be recognized by the viral RNA dependent RNA polymerase.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A DNA construct comprising the following operably linked polynucleotide elements in the 5' to 3' direction:
   i) a promoter;
   ii) a hammerhead ribozyme cleavage site;
   iii) a hammerhead ribozyme catalytic core;
   iv) a first hairpin ribozyme cleavage site in the antisense orientation;
   v) a non-functional or stuffer polynucleotide;
   vi) a second hairpin ribozyme cleavage site in the antisense orientation;
   vii) a hairpin ribozyme catalytic core in the antisense orientation;
   viii) reverse and forward primer annealing sites in the antisense orientation;
   ix) an inserted polynucleotide suspected of comprising a RNA promoter; and
   x) a third ribozyme catalytic core, wherein the third ribozyme catalytic core is in the sense orientation, is not a hairpin ribozyme catalytic core and does not comprise a hairpin ribozyme cleavage site.

2. The DNA construct of claim 1, wherein the promoter is functional in a prokaryotic cell, said promotor comprising a bacteriophage promoter selected from the group consisting of T7, T3 and SP6.

3. The DNA construct of claim 1 having at least about 60% sequence identity to a polynucleotide selected from the group of polynucleotides consisting of SEQ ID NO:1, SEQ ID NO:9, SEQ ID NO:10 and SEQ ID NO:11.

4. A method of identifying a RNA promoter comprising the steps of:
   a) transfecting a host cell with the DNA construct of claim 1, wherein the 5' promoter is capable of promoting transcription in the host cell; wherein the host cell expresses a RNA-dependent RNA polymerase and rolling circle transcription of the RNA construct or RNA transcribed from the DNA construct within the host cell when the inserted polynucleotide comprises a functional RNA promoter yields a circularized RNA comprising:
      i) a hammerhead ribozyme catalytic core in the antisense orientation;
      ii) a hairpin ribozyme cleavage site;
      iii) a hairpin ribozyme catalytic core;
      iv) reverse and forward primer annealing sites; and
      v) the inserted polynucleotide comprising a functional RNA promoter;
   b) isolating the circularized RNA;
   c) amplifying the inserted polynucleotide comprising a functional RNA promoter; and
   d) sequencing the inserted polynucleotide comprising a functional RNA promoter, thereby identifying the RNA promoter.

5. The method of claim 4, wherein the host cell is transfected with a polynucleotide that encodes an exogenous RNA-dependent RNA polymerase.

6. The method of claim 4, wherein the host cell is infected with an RNA virus.

7. The method of claim 6, wherein the host cell is infected with an RNA virus from a virus taxonomic Order selected from the group consisting of Mononegavirales, Nidovirales, Picornavirales, and Tymovirales.

8. The method of claim 6, wherein the host cell is infected with an RNA virus from a virus taxonomic Family selected from a group of celivirus, deltavirus, emaravirus, higrevirus, idaeovirus, ourmiavirus, polemovirus, sobemovirus, tenuivirus, umbravirus, and varicosavirus.

9. The method of claim 4, wherein the host cell is selected from the group consisting of an archaeal cell, a bacterial cell, an animal cell, a plant cell and a fungal cell.

10. The method of claim 4, wherein the sequencing comprises deep sequencing.

11. The DNA construct of claim 1, wherein the hammerhead ribozyme catalytic core is from a hammerhead ribozyme selected from the group consisting of Type I, Type II, Type III, HH9 and HH10.

12. The DNA construct of claim 1, wherein said first and/or second hairpin ribozyme cleavage sites have a polynucleotide selected from the group of SEQ ID NO:6 and SEQ ID NO:7.

13. The DNA construct of claim 1, wherein the non-functional or stuffer polynucleotide does not comprise any one of a functional RNA promoter, a primer annealing site, and a transcription modifying sequence.

14. The DNA construct of claim 1, wherein the non-functional or stuffer polynucleotide comprises from about 200 base pairs (bp) to 1000 base pairs.

15. The DNA construct of claim 1, wherein the hairpin ribozyme catalytic core is derived from the negative strand self-cleavage domain of a plant virus satellite RNA selected from the group consisting of the satellite RNA of tobacco ringspot virus (sTRSV), the satellite RNA of arabis mosaic virus (sArMV), and the satellite RNA of chicory yellow mottle virus (sCYMV).

16. The DNA construct of claim 1, wherein the hairpin ribozyme catalytic core is derived from the negative strand self-cleavage domain of the satellite RNA of tobacco ringspot virus (sTRSV).

17. The DNA construct of claim 1, wherein the hairpin ribozyme catalytic core comprises a polynucleotide selected from the group of polynucleotides consisting of SEQ ID NO: 3, SEQ ID NO: 4, SEQ ID NO:5 and SEQ ID NO:8.

18. The DNA construct of claim 1, wherein the inserted polynucleotide suspected of comprising an RNA promoter is a promoter selected from the group consisting of cDNA of a RNA virus genome, a promotor from genomic DNA, a mutagenized RNA promoter and a library of randomized chemically synthesized DNA sequences.

19. The DNA construct of claim 1, wherein the third ribozyme catalytic core comprises a hammerhead ribozyme catalytic core without a hairpin cleavage site at its 3' end.

20. The DNA construct of claim 1, wherein the third ribozyme catalytic core comprises a positive or negative strand hepatitis delta virus (HDV) ribozyme catalytic core.

* * * * *